US006177450B1

(12) United States Patent
Garret et al.

(10) Patent No.: US 6,177,450 B1
(45) Date of Patent: Jan. 23, 2001

(54) SYNERGIZING COMBINATION HAVING AN ANTAGONIST EFFECT ON NKI AND NK2 RECEPTORS

(75) Inventors: Claude Garret, Fontenay sous Bois; Francois Montier, Paris, both of (FR)

(73) Assignee: Aventis Pharma S.A.

( * ) Notice: Under 35 U.S.C. 154(b), the term of this patent shall be extended for 0 days.

(21) Appl. No.: 08/448,403

(22) PCT Filed: Jan. 18, 1994

(86) PCT No.: PCT/FR94/00055

§ 371 Date: Jun. 7, 1995

§ 102(e) Date: Jun. 7, 1995

(87) PCT Pub. No.: WO94/16697

PCT Pub. Date: Aug. 4, 1994

(30) Foreign Application Priority Data

Jan. 19, 1993 (FR) .................................... 93 00451

(51) Int. Cl.[7] ........................ A61K 31/445; A61K 31/40
(52) U.S. Cl. ........................ 514/323; 514/412; 514/416
(58) Field of Search .................... 514/323, 412, 514/416

(56) References Cited

U.S. PATENT DOCUMENTS 5,236,921   8/1993   Emonds-Ai et al. .

FOREIGN PATENT DOCUMENTS

| 0 474 561 | 3/1992 | (EP) . |
| 92/19254 | 11/1992 | (WO) . |
| 93/14084 | 7/1993 | (WO) . |

OTHER PUBLICATIONS

Martin et al, Chemical Abstracts, vol. 118, abstract No. 53102, 1992.*
Martin et al., "Influence of (±)–CP–96,345 and SR 48968 on electrical field stimulation of the isolated guinea–pig main bronchus," *European Journal of Pharmacology*, 224 (1992) pp. 137–143.
J. Pharmacol. Exp. Ther., vol. 262, No. 2, pp. 646–653, J.L. Ellis, 1992.
Br. J. Pharmacol., vol. 103, No. 2, pp. 1535–1541, C.A. Maggi, 1991.
Trends Pharmacol. Sci., vol. 13, No. 7, pp. 266–269, K.J. Watling, 1992.
J. Pharmacol. Exp. Ther., vol. 264, No. 3, pp. 1327–1332, A. Lecci, 1993.

* cited by examiner

Primary Examiner—William R. A. Jarvis
(74) Attorney, Agent, or Firm—Finnegan, Henderson, Farabow, Garrett & Dunner

(57) ABSTRACT

Synergising associations characterized in that they are comprised of at least one product having an antagonist activity on NK1 receptors and at least one product having an antagonist activity on NK2 receptors. Said associations are useful in the treatment of diseases involving the substance P and/or neurokinine A.

17 Claims, No Drawings

SYNERGIZING COMBINATION HAVING AN ANTAGONIST EFFECT ON NK1 AND NK2 RECEPTORS

This application is a 371 of PCT/FR94/00055, filed Jan. 18, 1994.

The present invention relates to the synergistic combination consisting of at least one antagonist of NK1 receptors and of at least one antagonist of NK2 receptors.

Substance P and neurokinin A are neuropeptides belonging to the tachykinin family. Tachykinins are endogenous ligands known for their ability to stimulate 3 types of receptors known as NK1, NK2 and NK3.

The effects of Substance P are mainly mediated by NK1 receptors. The effects of neurokinin A are mainly mediated by NK2 receptors.

Substance P is an undecapeptide which is implicated in many pathologies such as, for example, transmission of pain, disorders of the central nervous system, inflammatory or respiratory phenomena, and the like.

Neurokinin A is also implicated in numerous pathologies such as transmission of pain, arthritis, asthma, inflammatory phenomena, psychoses, tensional disorders, vesical disorders, cystites, and the like.

Until recently, despite research carried out and despite the abovementioned interest [M. R. Hanley, TINS, (5) 139 (1982)], no product acting specifically on Substance P or on neurokinin A and having a non-peptide structure had, in practice, been discovered.

Antagonists of NK1 receptors (antagonists of the effects of Substance P) are now known and described, especially in Patent Applications EP 429,366, EP 514,273, EP 514,275, WO 90/05525, WP 90/05729, WO 91/18899, WO 91/09844, WO 92/01688, WO 92/06079, WO 92/15585, WO 92/12151, WO 92/20661, WO 92/20676, WO 92/21677, WO 93/00330, WO 93/00331, WO 93/01159, WO 93/01169, WO 93/01165, WO 93/01170, WO 93/06099, WO 93/09116, WO 93/10073, WO 93/18023, WO 93/19064, WO 93/21155, WO 93/21181, WO 93/23380, EP 499,313, EP 394,989, EP 443,132, EP 482,539, EP 512,902, EP 517,589, EP 520,555, EP 522,808, EP 528,495, EP 532,456, EP 533,280, EP 536,817, EP 545,478, EP 559,538, XIIth Int. Symp. on Med. Chem., Basle, Sep. 13–17, 1992 or 3rd Meeting of the European Neuropeptide Club (Cambridge, Apr. 5–7, 1993).

Antagonists of NK2 receptors (antagonists of the effects of neurokinin A) are also known and described, especially in Patent Applications EP 428,434, EP 474,561, EP 512,901, EP 515,240, FR 2,678,267, WO 92/19254 or WO 93/14084.

J. L. Ellis et al., J. Pharmacol. Exp. Ther., 262(2), 646 (1992) mentions the combination of an antagonist of $NK_1$ receptors: CP 96345 and a peptide antagonist of $NK_2$ receptors (MEN 10376) but no study of the separate and then combined products was carried out and no synergy of action discovered.

C. A. Maggi, Br. J. Pharmacol., 103(2), 1535 (1991) describes the study of spantide and L-659,877 alone or in combination but, in as much as spantide is antagonist both of $NK_1$ and $NK_2$ receptors, this study could not make it possible to discover the advantage of a combination of an antagonist of $NK_1$ receptors and an antagonist of $NK_2$ receptors.

It has also been revealed that certain products are endowed with antagonist activity towards NK1 receptors and antagonist activity towards NK2 receptors: M. Murai et al., J. Pharm. Exp. Ther., 262(1), 403 (1992). However, none of these products has, until now, displayed a very high activity.

Until now, it had been supposed that the effects of antagonists of NK1 and NK2 receptors could act similarly and additively on certain functional groups. It has now been found that the effects of antagonists of NK1 receptors in combination with antagonists of NK2 receptors are potentiated, which opens a particularly advantageous route into therapeutic fields where Substance P and/or neurokinin A are involved.

As non-limiting examples, antagonists of NK1 receptors can be especially derivatives of the perhydroisoindole class, derivatives of the 2-substituted-3-aminoquinuclidine class, derivatives of the aminoazabicycloalkane class, derivatives of the 2-substituted-3-aminopiperidine class, derivatives of the 1-azabicyclo[3.2.2]nonan-3-amine class, derivatives of the N-alkylquinuclidinium salt class, derivatives of the pseudopeptide class, derivatives of the N,N-diacylpiperazine class, substituted aromatic derivatives, dialkylenepiperidino derivatives, quaternary salts of substituted piperidines, and the like.

By way of example, products of the class of perhydroisoindole derivatives can have the structure:

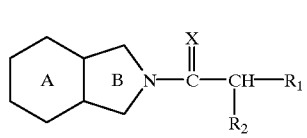

(I)

and their salts, when they exist, in which:

the $R_1$ symbol represents a phenyl radical optionally substituted by one or a number of halogen atoms or hydroxyl radicals, alkyl radicals which can optionally be substituted (by halogen atoms or amino, alkylamino or dialkylamino radicals), alkyloxy or alkylthio radicals which can optionally be substituted [by optionally substituted (by phenyl, hydroxyl or amino radicals) dialkylamino, alkylamino, amino or hydroxyl radicals, or dialkylamino radicals in which the alkyl parts form, with the nitrogen atom to which they are attached, a 5- to 6-membered heterocycle which can contain another heteroatom chosen from oxygen, sulphur or nitrogen, optionally substituted by an alkyl, hydroxyl or hydroxyalkyl radical)], or substituted by amino, alkylamino or dialkylamino radicals in which the alkyl parts can form, with the nitrogen atom to which they are attached, a heterocycle as defined above, or represents a cyclohexadienyl radical, a naphthyl radical or a saturated or unsaturated, mono- or polycyclic heterocyclyl radical (5 to 9 carbon atoms) and one or a number of heteroatoms chosen from oxygen, nitrogen or sulphur, and optionally substituted by a halogen atom or by an alkyl or alkyloxy radical, the $R_2$ symbol represents a hydrogen or halogen atom or a hydroxyl, alkyl, aminoalkyl, alkylaminoalkyl, dialkylaminoalkyl, alkyloxy, alkylthio, acyloxy, carboxyl, alkyloxycarbonyl, dialkylaminoalkyloxycarbonyl, benzyloxycarbonyl, amino or acylamino radical, the bicycle:

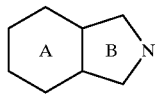

represents a perhydroisoindole or thiapyranopyrrole ring of general formula:

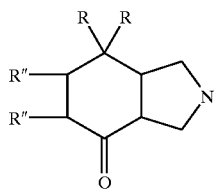

(Ia)

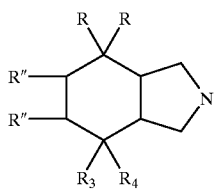

(Ib)

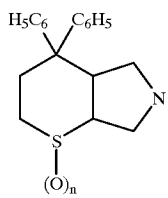

(Ic)

and the symbol X represents an oxygen or sulphur atom or a radical $NR_6$ in which $R_6$ is a hydrogen atom, an alkyl radical containing 1 to 12 carbon atoms and optionally substituted [by one or a number of carboxyl, dialkylamino, acylamino, alkyloxycarbonyl, alkyloxycarbonylamino, carbamoyl, alkylcarbamoyl or dialkylcarbamoyl radicals (it being possible for the alkyl portions of these substituents to themselves be substituted by dialkylamino or phenyl) or substituted by phenyl, substituted phenyl (substituted by halogen, alkyl, alkyloxy or dialkylamino), naphthyl, thienyl, furyl, pyridyl or imidazolyl radicals] or a dialkylamino radical, or else, if the ring is of formula (Ib) or (Ic), the symbol X represents an oxygen atom, or an NH radical, or else the bicycle:

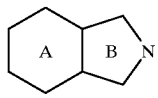

represents a perhydroisoindole or thiapyranopyrrole ring of general formula:

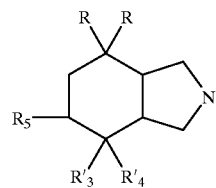

(Id)

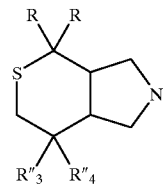

(Ie)

and the symbol X represents an oxygen atom.

In the general formulae (Ia) to (Ie):

the R symbols are identical and represent phenyl radicals optionally substituted by a halogen atom or by a methyl radical in the 2- or 3-position, the R" symbols are identical and represent hydrogen atoms or together form a bond, the $R_3$ symbol represents a halogen atom or a hydroxyl radical and the $R_4$ symbol represents a hydrogen atom or, simultaneously with $R_3$, represents a halogen atom, the $R'_3$ symbol represents a phenyl radical optionally substituted in the 2-position by an alkyl or alkyloxy radical (1 or 2 carbon atoms), and the $R'_4$ symbol represents a fluorine atom or a hydroxyl radical, and the $R_5$ symbol represents a hydrogen atom or else the $R'_4$ and $R_5$ symbols represent hydroxyl radicals, or else the $R'_4$ symbol forms a bond with $R_5$, the $R''_3$ symbol represents a hydrogen atom and the $R''_4$ symbol represents a fluorine atom or a hydroxyl radical, or else the $R''_3$ symbol represents a phenyl radical optionally substituted in the 2-position by an alkyl or alkyloxy radical (1 or 2 carbon atoms), and the $R''_4$ symbol is a hydroxyl radical, or else the $R''_3$ and the $R''_4$ symbols together form an oxo radical, the n symbol is an integer from 0 to 2; it being understood that the products of general formula (Ia) to (Id) can have stereoisomeric forms which are described in more detail in European Patent Applications EP 429,366, EP 514,273 and EP 514,275 or in International Application WO 93/21155, and that the products of general formula (Ie) exist in the (3aS,7R,7aR), (3aR,7S,7aS) or (3aRS,7SR,7aSR) form, if $R_4$ is hydroxyl and $R_3$ is a phenyl radical, or exist in the (3aR,7S,7aS), (3aS,7R,7aR) or (3aRS,7SR,7aSR) form or their mixtures, if $R_3$ is hydrogen and $R_4$ is hydroxyl, or exist in the (3aR,7R,7aS), (3aS,7S,7aR) or (3aRS,7RS,7aSR) form or their mixtures, if $R_3$ is hydrogen and $R_4$ is fluorine, or exist in the (3aS,7aR), (3aR,7aS) or (3aRS,7aSR) form or their mixtures if $R_3$ forms an oxo radical with $R_4$.

By way of example, products of the 2-substituted-3-aminoquinuclidine class, derivatives of the aminoazabicycloalkane class, derivatives of the 2-substituted-3-aminopiperidine class, derivatives of the 1-azabicyclo[3.2.2]nonan-3-amine class and derivatives of the N-alkylquinuclidinium salt class can be products of general formula:

(II)

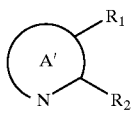

in their stereoisomeric forms or their mixtures, in which the ring:

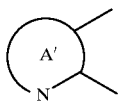

represents a monocyclic nitrogenous heterocycle or a condensed polycyclic of structure:

(IIa)

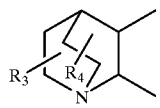

(IIb)

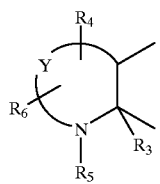

(IIc)

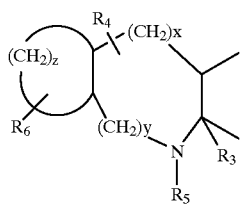

(IIc')

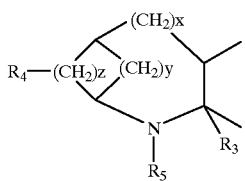

(IId)

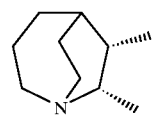

(IIe)

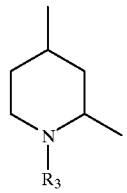

(IIf)

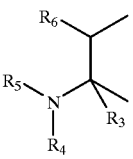

(IIg)

When the A' ring corresponds to the general formula (IIa):

1) $R_4$ is a hydrogen atom, $a_1$) $R_1$ is a radical =N—$CH_2$—R or —N=CH—R, in which R is cycloalkyl (5 to 7 carbon atoms), norbornyl, pyrrolyl, thienyl, pyridyl, indolyl, biphenyl or phenyl which can be substituted by 1 or 2 substituents chosen from fluorine, chlorine, bromine, trifluoromethyl, alkyl or alkyloxy (1 to 3 carbon atoms), carboxyl, alkyloxycarbonyl, in which the alkyl part contains 1 to 3 carbon atoms, or benzyloxycarbonyl, and $R_2$ is a radical Ar—CHR'— in which R' is a branched alkyl radical (3 or 4 carbon atoms), a branched alkylene radical (5 or 6 carbon atoms), a cycloalkyl radical (3 to 7 carbon atoms) or furyl, thienyl, pyridyl, indolyl, biphenyl or phenyl which can be substituted by 1 or 2 substituents chosen from fluorine, chlorine, bromine, trifluoromethyl, alkyl or alkyloxy (1 to 3 carbon atoms), carboxyl, alkyloxycarbonyl, in which the alkyl part contains 1 to 3 carbon atoms, or benzyloxycarbonyl, and Ar is a phenyl radical or else $a_{2.1}$) $R_1$ is a radical —NH—$CH_2$—R in which R is defined as above and $R_2$ is defined as above, or $a_{2.2}$) R represents a phenyl radical disubstituted by a methoxy radical and a branched butyl radical, if $R_2$ is a benzhydryl radical, or else $a_{2.3}$) R represents a phenyl radical trisubstituted by radicals $X_1$ to $X_3$ in which $X_1$ is H, alkyl or alkyloxy (1 to 10 carbon atoms), optionally substituted by 1 to 3 fluorine atoms, and $X_2$ and $X_3$ are H, halogen, $NO_2$, alkyl or alkyloxy (1 to 10 carbon atoms), optionally substitued by 1 to 3 fluorine atoms, OH, CN, phenyl, $NH_2$, alkylamino, dialkylamino, alkylcarbamoyl, alkylcarbamoylalkyl or acylamino (in which the alkyl or acyl parts contain 1 to 6 carbons), or alkyloxyalkyl (in which the alkyl parts contain 1 to 4 carbon atoms) if $R_2$ is either Ar—CHR'— in which R' is defined as above or represents alkyl or alkyloxy (1 to 10 carbon atoms) optionally substituted by 1 to 3 fluorine atoms, and Ar is a phenyl radical, or a phenyl, biphenyl, naphthyl, pyridyl, thienyl or furyl radical which can be mono- to trisubstituted by halogen or alkyl or alkyloxy (1 to 10 carbon atoms) optionally substituted by 1 to 3 fluorine atoms, and $R_3$ is a hydrogen atom, or else $a_3$) $R_1$ is —NH—(C=Y)—R in which R is a benzopyran derivative optionally containing another heteroatom (O, S or NR' in which R' is H, alkyl or aralkyl) or a benzofuran derivative optionally substituted in the position α to the oxygen by methyl radicals, and/or substituted by an oxo or thioxo radical and/or substituted on the phenyl ring by halogen, alkyl, haloalkyl, aralkyl, alkyloxy, aralkyloxy, acyl, acyloxy, OH, $NH_2$, CN, $NO_2$, —NH—CO—R″, s(O)n—R″, —NH—$SO_2$R″, COOR″, CONR″R‴, OCONR″R‴, CSNR″R‴ or $SO_2$NR″R‴, in which R″ and R‴ are H, alkyl, phenyl or aralkyl, and Y is O, S or 2H, $R_2$ is —$CHR_5R_6$ in which $R_5$ is thienyl or phenyl and $R_6$ is alkyl, alkenyl, cycloalkyl, furyl, thienyl, pyridyl, indolyl, biphenyl or phenyl, and $R_3$ is H or alkyl;

$b_1$) $R_1$ is defined as in $a_1$) or in $a_{2.1}$) and R is defined as in $a_1$) or represents 2,3-dihydrobenzofuranyl, alkyloxythienyl, in which the alkyl part contains 1 to 3 carbon atoms, hydroxypyridyl, quinolyl, naphthyl, alkyloxynaphthyl, in which the alkyl part contains 1 to 3 carbon atoms, 2,3-methylenedioxyphenyl, or phenyl substituted by 1 or 2 radicals chosen from the radicals mentioned above or cyano, nitro, amino, N-monoalkylamino (1 to 3 carbon atoms), allyl, hydroxyl, carboxybenzyloxy, alkyloxycarbonylbenzyloxy, in which the alkyl part contains 1 to 3 carbon atoms, carboxamido or N,N-dialkylcarboxamido, in which the alkyl parts contain 1 to 3 carbon atoms, and R' is defined as above or represents phenyl substituted by 1 or 2 radicals chosen from the radicals mentioned above or phenylalkyl, in which the alkyl part contains 1 to 3 carbon atoms, allyloxy or hydroxyl, and $R_3$ is a hydrogen atom or an alkyl radical (1 to 4 carbon atoms) situated in the 5-position, or else $b_2$) $R_1$ is defined as in $a_{2.3}$) and $R_2$ is phenyl, biphenyl, naphthyl, pyridyl, thienyl or furyl which can be mono- to trisubstituted by halogen or alkyl or alkyloxy (1 to 10 carbon atoms) optionally substituted by 1 to 3 fluorine atoms, and $R_3$ is an alkyl radical (1 to 6 carbon atoms), or else c) $R_1$ is a radical —NH—$CH_2$—R in which R is phenyl, thienyl, pyridyl or furyl optionally substituted by 1 to 3 substituents chosen from fluorine, chlorine, bromine, iodine, trifluoromethyl, alkyl or alkyloxy (1 to 4 carbon atoms), $R_2$ is a phenyl, naphthyl, thienyl, pyridyl or furyl radical optionally substituted as defined above for R, and $R_3$ is a hydrogen atom or an alkyl radical (1 to 6 carbon atoms) situated in the 5- or 6-position, or else d) $R_1$ is a radical —NH—$CH_2$—R in which R is phenyl, naphthyl, pyridyl, quinolyl, thienyl, furyl, phenoxyphenyl, oxazolyl, tetrazolyl, thiazolyl, imidazolyl or pyrazolyl optionally substituted by alkyl or alkyloxy substituents, optionally carrying 1 to 3 halogens, alkylthio, alkylsulphinyl, alkylsulphonyl, alkylsulphonylamino, dialkylamino, in which the alkyl parts can be substituted by alkylsulphinyl or alkylsulphonyl (in which the alkyl parts contain 1 to 6 carbons), sulphonamido or alkenyl (2 to 6 carbons) substituents, or in which R is phenyl substituted by halogen, alkynyl, alkylamino, N-alkyl-N-(alkylsulphonyl) amino or N-alkyl-N-alkanoylamino (which can be substituted by halogen on the alkylsulphonyl or alkanoyl part), alkylsulphonylamino or alkanoylamino, in which the alkyl parts can be substituted by halogen, $R_2$ is a radical Ar—CH(Ar')— in which Ar and Ar' are cyclic radicals such as R above, which can be substituted by alkyl, alkyloxy, alkylthio, alkylsulphinyl, alkylamino (in which the alkyl parts contain 1 to 4 carbons), trifluoromethyl or trifluoromethoxy and $R_3$ is optionally substituted (by alkyloxy, carbamoyl, —$CONR_aR_b$, —COOH, —$COOR_a$, —$CHR_aOR_b$, $CHR_aNR_bR_c$, —$COR_a$, —$CONR_aOR_b$, or aryl as defined for optionally substituted R, the alkyl radicals having 1 to 6 carbons and Ra, Rb and Rc being optionally substituted aryl, cycloalkyl, alkyloxy, alkyl or H) alkyl, alkenyl (2 to 6 carbons), cycloalkyl (3 to 8 carbons), or a radical as defined above for the substituents of the alkyl radical, or a radical Y—$(CH_2)_m$—$CHR_d$—$(CH_2)_n$—$NR'_d$—CO— in which Y is —CN, —$CH_2$Z or —COZ (in which Z is OH, $NH_2$, —Oalkyl, —NHalkyl or —N(alkyl)$_2$), $R_d$ is H, alkyl, benzyl or —$(CH_2)_p$—Y and $R'_d$ is defined as Rd or substituted (by OH, $NH_2$, —$SCH_3$ or SH) alkyl or 4-hydroxybenzyl or 3-indolylmethyl.

2) $R_3$ in the 5-position forms, with $R_4$, an alkylene chain containing 3 to 5 carbon atoms if $R_4$ is in the 6-position, or containing 2 or 3 carbon atoms if $R_4$ is in the 7-position, or containing 2 to 4 carbon atoms if $R_4$ is in the 8-position, or else, when $R_3$ is in the 5-position and $R_4$ is in the 6-position, $R_3$ and $R_4$ can form a chain:

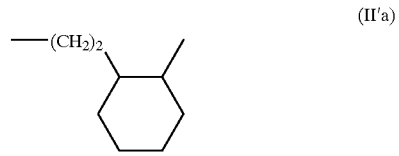

(II'a)

or else, when $R_4$ is in the 8-position and $R_3$ is in the 5-position, $R_3$ and $R_4$ can form a chain: —CH2—X—CH2— in which X is O, S, NH or >N(alkylamino), in which the alkyl part contains 1 to 3 carbon atoms.

$R_1$ has the structure defined in $1a_{2.1}$) and R is defined as in $1a_{2.3}$) or represents cycloalkyl (5 to 7 carbon atoms), pyrrolyl, thienyl, pyridyl or phenyl which can be substituted by 1 to 3 substituents chosen from fluorine, chlorine, bromine, trifluoromethyl, alkyl or alkyloxy (1 to 3 carbon atoms), carboxyl, alkyloxycarbonyl, in which the alkyl part contains 1 to 3 carbon atoms, or benzyloxycarbonyl, and $R_2$ is a radical —CHR'R″ in which R' is a furyl, thienyl, pyridyl, indolyl, biphenyl or phenyl radical which can be substituted by 1 or 2 substituents chosen from halogen, alkyl or alkyloxy (1 to 10 carbon atoms), which can be substituted by 1 to 3 fluorine, carboxyl, alkyloxycarbonyl (the alkyl part containing 1 to 3 carbons) or benzyloxycarbonyl, and R″ is thienyl, phenyl, halophenyl or phenyl substituted by alkyl or alkyloxy (1 to 10 carbon atoms), which can be substituted by 1 to 3 fluorine.

When the A' ring corresponds to the general formula (IIb):

1) Y is $(CH_2)_n$ in which n is equal to 1 to 6 and can represent an unsaturated chain, $R_1$ is a radical —NR'—$CH_2$—R in which R is aryl chosen from phenyl, naphthyl, indanyl, thienyl, pyridyl, furyl, thiazolyl, isothiazolyl, oxazolyl, isoxazolyl, triazolyl, tetrazolyl and quinolyl optionally substituted by 1 or more substituents chosen from halo, nitro, alkyl, alkyloxy, trifluoromethyl, amino, phenyl, alkylamino, formamido, acylamido, acylamidoalkyl, alkylcarbamoyl or cycloalkyl (3 to 7 carbon atoms) optionally substituted by 1 or 2 substituents as mentioned above and in which one of the carbon atoms can be replaced by N, O or S, and R' is a hydrogen atom or an alkyl radical, or $R_1$ is defined as in $1a_{2.3}$), $R_2$ is a hydrogen atom, a phenylalkyl, benzhydryl or straight or branched alkyl radical or an aryl or cycloalkyl radical as defined above for R or an aryl radical such as thiazolyl, isothiazolyl, oxazolyl, isoxazolyl, triazolyl or tetrazolyl, it being possible for these various rings to be substituted by 1 or more substituents chosen from the substituents mentioned above for R, or chosen from dialkylamino, alkyloxycarbonyl, alkyloxycarbonylalkyl, acyloxy, acylalkyloxy, acyl or acylalkyl, $R_3$ is a hydrogen atom or, when $R_1$ is defined as in 1a2.3), can be a phenyl or alkyl (1 to 6 carbons) radical, or else $R_2$ and $R_3$ form, together with the carbon to which they are attached, a saturated, 3- to 7-membered carbocycle in which the carbon atoms can optionally be replaced by O, N or S, $R_5$ is a radical —(CHR")$_m$—R''' in which m is an integer from 0 to 6, it being possible for each of the CHR" units to form a double bond with the adjacent unit, and not all the R" radicals necessarily being identical, $R_4$ and $R_6$ can be hydrogen atoms or hydroxyl, halo, amino, alkylamino, dialkylamino, alkyloxy, alkyloxycarbonyl, alkyloxycarbonylalkyl, acyloxy, acylalkyloxy, acyl or acylalkyl radicals or radicals as mentioned above for the definition of $R_2$, with the proviso of not being able to form a ring with $R_5$, or, if $R_1$ is defined as in 1a$_{2,3}$), $R_4$ and $R_6$ can also be oxo, hydroxyalkyl or alkyloxyalkyl, and R" and R''' are defined as $R_4$ and $R_6$, or, if $R_1$ is a radical defined as in 1a2.3), R" can also be =N—OH and R''' a radical —NHCOR$_d$, —NHCH$_2$R$_d$, SO$_2$R$_d$ or NHSO$_2$R$_d$, and R$_d$ is H, alkyl, phenylalkyl or phenyl substituted by alkyl (the alkyl parts having 1 to 6 carbons), or else 2) —Y—N(R$_5$)— is the residue of an azabicyclic system (for example, quinuclidinyl, azabicycloheptyl or azabicyclooctyl), a) $R_1$ is a radical —X—CH$_2$—R in which X is an oxygen or sulphur atom and R is a phenyl radical optionally substituted by 1 to 3 identical or different radicals chosen from alkyl, alkenyl or alkynyl (2 to 6 carbon atoms), halogen, cyano, nitro, trifluoromethyl, trimethylsilyl, —OR', —SCH$_3$, —SOCH$_3$, —SO$_2$CH$_3$, —NR'R", —NR'COR", —NR'CO$_2$R", —CO$_2$R' or —CONR'R" in which R' and R", which are identical or different, represent hydrogen, alkyl, phenyl or trifluoromethyl, $R_2$ represents a radical —CR$_a$R$_b$R$_c$ in which R$_a$ and R$_b$, which are identical or different, represent phenyl or thienyl optionally substituted by halo or trifluoromethyl, or cycloalkyl, or Ra can also represent phenyl or thienyl substituted by alkyloxy or Rb can also represent benzyl, which can be substituted as defined above, and R$_c$ is hydrogen or hydroxyl, and $R_3$, $R_4$ and $R_6$ are H, or else b) $R_1$ is a radical —CH$_2$—CHX—Ar or =CH—CHX—Ar in which Ar is a phenyl radical which can be substituted as defined above in a), X is H, OH, =O or halogen, $R_2$ is a radical —CR$_a$R$_b$ in which R$_a$ and R$_b$, which are identical or different, represent phenyl, thienyl or benzyl optionally substituted by halo or trifluromethyl, and $R_3$, $R_4$ and $R_6$ are H, or else c) $R_1$ is a radical —NR"—CH$_2$—R in which R is defined as in IIb 1) [for R' is H or alk] or represents alkyloxycarbonyl, formyl, hydroxymethyl, phenoxymethyl or alkyloxymethyl, $R_2$ is defined as in IIb 1), $R_3$, $R_4$, $R_6$ and R" are H, alkyl or phenyl, or else d) —Y— substituted by $R_4$ and $R_6$ radicals is a —CHRa-CRb(CRcRd)-chain in which one of Ra is H, hydroxymethyl, alkyl, acyloxyalkyl, alkyloxymethyl or benzyloxymethyl, Rb and Rc are H, alkyl or phenyl and Rd is methyl or hydroxymethyl, $R_1$, $R_2$ and $R_3$ are defined as above in c) and $R_5$ is H, benzyl or a radical [(CH$_2$)$_m$Re]—Rf in which Re and Rf are defined as R' and R" below in IIg);

3) $R_1$ is defined as for the formula (IIb)-2a), it being understood that R in —X—CH$_2$—R can also carry an SR', SOR' or SO$_2$R' substituent, $R_2$ is a phenyl, naphthyl, indazolyl, thienyl, furyl, pyridyl, thiazolyl, tetrazolyl or quinolyl radical which can be substituted by alkyl, alkyloxy, halogen or trifluoromethyl, or a benzhydryl or benzyl radical, it being possible for these radicals to be substituted by alkyl or alkyloxy (1 to 6 carbons), halogen or CF$_3$, Y is —(CH$_2$)$_n$— in which n is equal to 1 to 3, $R_3$ is H, $R_4$ and $R_6$ are H, halogen, —CH$_2$OR°, alkyl, oxo, COOR° or CONR°R° in which R° is H, CF$_3$, alkyl or phenyl, and $R_5$ is H or optionally substituted alkyl [substituted by COOR°°, CONR°°R°°, OH, CN, COR°, —NR°°R°°, C(NOH)NR°°R°°, CONHphenylalkyl, COCOOR°°, COCONR°°R°°, optionally substituted phenyl (substituted by 1 or more alkyl, alkyloxy, halogen or CF$_3$ substituents), or by an aromatic heterocycle which can itself be substituted], R° is defined as above and R°° is H or alkyl; it being understood, except when especially mentioned, that the alkyl radicals and parts mentioned above contain from 1 to 6 carbon atoms), When the A' ring corresponds to the general formula (IIc):

x and y are integers from 0 to 4 and z is an integer from 0 to 6, it being understood that the ring containing (CH$_2$)$_z$ can contain up to 3 double bonds and one of the (CH$_2$)$_z$ can be replaced by O, S or N, $R_1$ is defined as in the case where A' is of formula (IIb)-1), R is defined as in the case where A' is of formula (IIb)-1) or represents thiazolyl, isothiazolyl, oxazolyl, isoxazolyl, triazolyl or tetrazolyl, optionally substituted by 1 or more substituents, the substituents being chosen from the radicals mentioned above for the general formula (IIb)-1) or phenyl, alkylcarbamoyl or alkylcarbamoylalkyl and R' is defined as in the case where A' is of formula (IIb)-1) or represents an alkyl radical substituted by hydroxyl, alkyloxy or fluoro, $R_2$ and $R_3$ are defined as for (IIb)-1), $R_5$ is a radical —(CHR")$_m$—R''' in which m is an integer from 0 to 12, it being possible for each of the CHR" units to form a double or a triple bond with the adjacent unit, and not all the R" necessarily being identical, or else $R_5$ is defined as above for the formula (IIb)-1) and $R_4$, $R_6$, R" and R''' are defined as for the formula (IIb)-1) or can be carboxyl or carboxyalkyl radicals, it being understood, except when especially mentioned, that the alkyl radicals and parts mentioned above contain from 1 to 6 carbon atoms.

When the A' ring corresponds to the general formula (IIc'):

$R_1$ is defined as above in (IIc), it being possible for the R radical of —NR'—CH$_2$—R also to carry a dialkylamino substituent, $R_2$ is defined as above in (IIc), it being understood that the phenyl radicals of the benzhydryl can optionally be replaced by naphthyl, thienyl, furyl or pyridyl, R₃ is defined as above in (IIc), or represents phenyl, R₄ is defined as above in (IIc) with the exception of carrying a COOH or carboxyalkyl substituent, or can be substituted by an oxo or nitrile radical, or groups as defined for R₂, R₅ is defined as above in (IIc) in which R''' is hydroxyimino, or one of the groups mentioned above for R₂ and R₄, and R'' is —NHCO—R°, —NHCH₂R°, —NHSO₂R° or one of the groups mentioned above for R₂ and R₄, and R° is H, alkyl, phenyl or phenylalkyl, and m is 0 to 8, x is 0 to 2, y and z are 1 to 4 and any of the carbon atoms of (CH₂)_z can be substituted by the R₄ radical.

When the A' ring corresponds to the general formula (IId):

R₁ is a radical —NH—CH₂—R in which R is a phenyl radical optionally substituted by 1 or 2 identical or different radicals chosen from fluorine, chlorine or bromine atoms or trifluoromethyl, alkyl, alkyloxy, carboxyl, alkyloxycarbonyl or benzoyloxy radicals, the alkyl radicals and parts (1 to 3 carbon atoms);

R₂ is a benzhydryl radical in which the phenyl rings can be substituted by 1 or 2 radicals as mentioned above.

When the A' ring corresponds to the general formula (IIe):

R₁ is defined as above when the A' ring corresponds to the general formula (IId) and R is phenyl, thienyl, furyl or pyridyl optionally substituted by 1 to 3 substituents chosen from cyano, nitro, amino, N-alkylamino, fluorine, chlorine, bromine, trifluoromethyl, alkyl, alkyloxy, allyloxy, alkyloxycarbonyl, carboxamido or N,N-dialkylcarboxamido, the alkyl radicals and parts (1 to 3 carbon atoms);

R₂ is a benzhydryl radical and

R₃ is an alkyl (1 to 4 carbon atoms), allyl, phenylalkyl, in which the alkyl part contains 1 to 6 carbon atoms, carboxyalkyl, in which the alkyl part contains 1 to 10 carbon atoms, or alkyloxycarbonylalkyl, in which the alkyloxy part contains 1 to 4 carbon atoms and the alkyl part contains 1 to 10 carbon atoms, radical, and X is a pharmaceutically acceptable counterion, chosen from chloride, fluoride, bromide, iodide, mesylate, tosylate or trifluoromethanesulphonate.

When the A' ring corresponds to the general formula (IIf):

R₁ is a radical —X—NR'—X'—R in which X is alkyl, CO or a bond, X' is CO, oxoalkyl, oxo(aza)alkyl or alkyl optionally substituted by phenyl, hydroxymethyl or COOH, which can be esterified or in the amide form, or substituted in the α-position by OH, R' is H, alkyl, carbamoyl or alkanoyl or alkenoyl optionally substituted by COOH, which can be esterified or in the amide form, and R is optionally substituted aryl or optionally partially hydrogenated heterocyclyl, R₂ is a radical —X''—R'' in which X'' is methylene, ethylene, a bond, carbonyl, optionally in the ketal or optionally etherified hydroxymethylene form, and R'' is cycloalkyl or optionally substituted heterocyclyl or aryl, and R₃ is aralkyl, aralkyloxyalkyl, heteroaralkyl, aroyl, heteroaroyl, cycloalkylcarbonyl, aralkanoyl, heteroaralkanoyl, aralkyloxycarbonyl or arylcarbamoyl, which can be substituted, or the acyl residue of an amino acid optionally N-substituted by alkyl or carbamoylalkanoyl, and their stereoisomeric forms.

When the A' ring is replaced by the general formula (IIg):

R₁ is —NH—CH₂—R in which R is defined as above in IIb-1) (when R' is H), or represents alkyloxycarbonyl, formyl, hydroxymethyl, phenoxymethyl or alkyloxymethyl, R₂ is H, alkyl or phenyl optionally substituted by 1 or more substituents chosen from halogen or alkyl or alkyloxy, optionally substituted (by 1 to 3 fluorines), R₃ is defined as above R [in IIb-1)], with the exception of representing aminoalkyl or alkylcarbamoyl, or represents alkyl or phenylalkyl or benzhydryl, which can be substituted on the phenyl by a substituent as in the definition above, R₄ is —[(CH₂)_m R']—R'' in which R' and R'' are defined as R₃ or represent OH, halogen, COOH, carboxyalkyl, alkylamino, dialkylamino, alkyloxy, alkyloxycarbonyl, alkyloxycarbonylalkyloxy, acyloxy, acylalkyloxy or acyl and m is 0 to 12, R₅ is H, alkyl, cycloalkyl (6 to 10 carbons) containing 2 condensed or bridged rings or benzyl, in which the phenyl part can be substituted by 1 or more substituents chosen from halogen or alkyl or alkyloxy, optionally substituted (by 1 to 3 fluorines), R₆ is H, cycloalkyl (3 to 8 carbons), alkyl or phenyl optionally substituted by 1 or more substituents chosen from halogen or alkyl or alkyloxy, optionally substituted (by 1 to 3 fluorines), it being understood that, except when especially mentioned, the alkyl portions contain 1 to 6 carbons; and, among these products, more especially 1-N-cyclohexyl-1-phenyl-2-N'-[(2-methoxyphenyl)methyl]-1,2-ethanediamine.

By way of example, products of the pseudopeptide class can be especially:

A) Products of General Formula

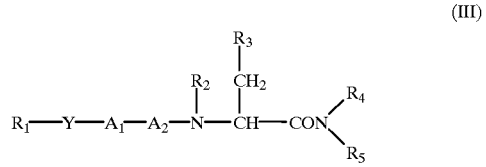

(III)

in which:

1) A₁ is a carbonyl radical,

A₂ is the residue of an amino acid, with the exception of D-Trp, which can be substituted, R₁ is an alkyl, aryl, arylamino, pyridyl, pyrrolyl, pyrazolopyridyl or quinolyl radical or a radical of general formula:

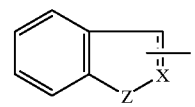

(III')

in which Z is O, S or NH and X is —CH— or N, which can optionally be substituted (especially by alkyl), and ===== is a single or double bond, Y is a bond or an alkylene or alkenylene radical, R₂ is H or alkyl, R₃ is a phenyl radical optionally substituted by hydroxyl in the 4-position or by 1 or 2 substituents chosen from alkyl, which can carry up to 3 halogens, amino, acylamino, optionally esterified carboxyalkyloxy, halogen, alkyloxy or nitro, and R₄ is optionally substituted alkyl, and $R_5$ is pyridylalkyl or optionally substituted aralkyl, or else $R_4$ and $R_5$ are bonded together to form a condensed benzo alkylene chain, it being understood that the nature of the substituents and of the amino acid residues and the length of the carbon chains are as defined in European Patent Application EP 394,989 or EP 482,539, or else 2) $A_1$ is a carbonyl or sulphonyl radical,
   $A_2$ is a residue

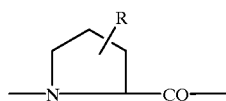
(III″)

in which R is a hydroxyl or alkyloxy radical,
Y is a bond or an alkenylene radical,
$R_1$ is an aryl radical or a radical of formula (III′) in which Z is O or $NR_6$, $R_6$ being H or alkyl, and ═══ is a double bond,
$R_2$ is a hydrogen atom,
$R_3$ is a naphthyl radical,
$R_4$ is a hydrogen atom or an optionally substituted alkyl radical, and
$R_5$ is optionally substituted aralkyl, it being understood that the nature of the substituents and the length of the carbon chains are as defined in European Patent Application EP 443,132.

B) Products of General Formula

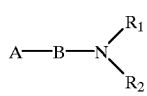
(IIIa)

in which:
$R_1$ and $R_2$ are H, alkyl (1 to 6 carbons), cycloalkyl (3 to 7 carbons) or benzyl,
B is the residue of an aromatic amino acid, and
A is either a radical of structure:

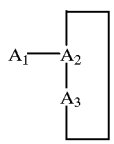

in which $A_1$ is a bond or an optionally protected tryptophan, β-naphthylalanine, leucine or 2-azabicyclo[2.2.2]octane-3-carbonyl residue, $A_2$ is an aspartic or glutamic residue and $A_3$ is a 1,2,3,4-tetrahydroisoquinoline-3-carbonyl, 2-azabicyclo[2.2.2.]octane-3-carbonyl, methylphenylalanine, arginine, protected arginine, 6,7-dihydroxy-1,2,3,4-tetrahydroisoquinoline, spinacine, 4-hydroxyproline, β-naphthylalanine or proline residue, it being understood that the —CO—NH— bond between $A_1$ and $A_2$ or between $A_2$ and B can be replaced by —CH$_2$—NH— or —CH$_2$—S— when $A_1$ is a bond,
or A is a peptide residue of structure:

—$A_4$—$A_5$—$A_6$—P in which $A_4$ and $A_5$ are 2-azabicyclo[2.2.2]octane-3-carbonyl or β-naphthylalanine or $A_5$ is a bond or a pheny-lalanine residue, $A_6$ is a bond or tryptophan optionally protected by formyl or methyl or 2-azabicyclo[2.2.2]octane-3-carbonyl, it being understood that when $A_5$ and $A_6$ are not bonds, the CO—NH bond which separates them can be replaced by —CH$_2$—NH— or —CH$_2$—S—, and P is H or an amine protective group such as benzyloxycarbonyl, t-butoxycarbonyl, 3-indolylcarbonyl, benzhydrylcarbonyl or fluorenylmethyloxycarbonylcarbonyl, and their stereoisomeric forms.

By way of example, products of the diacylpiperazine class can be especially products of general formula:

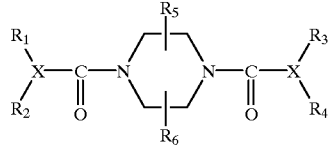
(IV)

in which
X is —CH< or —N<,
$R_1$ is H, alkyl (1 to 8 carbons), phenyl or phenylalkyl substituted (on the ring) by alkyl, halogen, OH, CF$_3$, NH$_2$, NHalkyl, N(alkyl)$_2$, —COOH or COOalkyl,
$R_2$ is defined as $R_1$ or —CH$_2$—$R_1$ or represents cycloalkyl (3 to 7 carbons),
$R_3$ and $R_4$ are independently phenyl as defined for $R_1$, alkyl (1 to 6 carbons), which can be substituted as phenyl above or substituted by SOX-alkyl, in which x is 0 to 2, or cycloalkyl (3 to 7 carbons), or else the phenyls formed by $R_3$ and $R_4$ can be combined at the ortho position to form a tricyclic group with X, or else $XR_1R_2$ can be —OR$_2$,
$R_5$ and $R_6$ are alkyl, COOR′, —CH$_2$OCOR′, —CH$_2$OH, —CH$_2$OR″, —CH$_2$S(O)$_x$R″, —CH$_2$OCONR′R″, —CH$_2$CONR′R″, —CONR′R″, —COOR°, —CH$_2$COOR′, —CH$_2$COOR°, —CONHSO$_2$R°°, —CH$_2$NR′CONR′R″, or methyl substituted by amino, alkylamino or dialkylamino and R′ is H or alkyl, R″ is defined as $R_3$ above with the exception of carrying an SO$_x$-alkyl or alkyloxy substituent, or else R′ and R″ can, if appropriate, be joined to form a 5- or 6-membered ring which can carry another heteroatom such as O, S(O)$_x$ or N optionally substituted by alkyl, aryl or arylmethyl, R° is H, acyloxymethyl optionally substituted on the methyl as N above or arylmethyl and R°° is optionally substituted alkyl, polyfluoroalklyl, cycloalkyl, heteroaryl or aryl; or else
$R_6$ is H.

By way of example, substituted aromatic derivatives can be especially

1) Products of General Formula

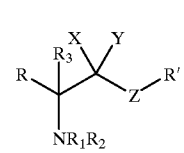
(V)

in which $R_1$ and $R_2$ are independently H, alkyl, which can be substituted (by OH, CN, CORa, COORa, CONRaRb, or NRaRb), CORa, COORa or CONRaRb in which Ra and Rb can be H, alkyl, phenyl or phenylalkyl (1 to 4 carbons) (optionally substituted on the ring by alkyl, alkyloxy, halogen or trifluoromethyl), $R_3$ is H or alkyl, X and Y are H or together form =O, Z is O, S or NR" in which R" is H or alkyl, R' is a radical —CHR°R°° in which R° is —(CH$_2$)$_n$-phenyl which can be substituted on the ring by 1 or more alkyl, alkenyl or alkynyl (2 to 6 carbons), halogen, CN, NO$_2$, CF$_3$, trimethylsilyl, ORa, SRa, SORa, SO$_2$Ra, NRaRb, NRaCORb, NRaCOORb, COORa or CONRaRb in which Ra and Rb are defined as above with the exception of being substituted phenyl, a) or else $R_1$ and $R_2$ can also be CONRaCOORb or SO$_2$Ra, R°° is H, alkyl or optionally substituted phenyl as defined for R°, and n in R° equals 0, and R is Q—CH$_2$— in which Q is optionally substituted phenyl, naphthyl, benzothiophenyl, benzofuranyl, benzyl or indazolyl;

b) or else $R_1$ and $R_2$ can also be CO-alkyl-NRaRb, CONRaCOORb or SO$_2$Ra, $R_3$ is defined as above for the general formula (V) or represents alkenyl, X and Y are defined as for the general formula (V) or Y is OH or alkyloxy or X and Y together form =NOR", Z is a —CH$_2$— or —CH= radical, R°° is H or forms a double bond with Z and n in R° equals 0, and R is Q—CH$_2$— in which Q is phenyl substituted by 1 or more halogens, or optionally substituted naphthyl, indolyl, benzothiophenyl, benzofuranyl benzyl or fluorenyl;

c) or else $R_1$ and $R_2$ can also be alkyl substituted by CO-alkyl-NRaRb or CON(Ra)alkylCONRaRb, phenyl (optionally substituted by alkyl, alkyloxy, halogen or trifluoromethyl), alkenyl (2 to 6 carbons), haloacyl, CO-alkyl-NRaRb or CON(Ra)alkylCONRaRb, or $R_1$ and $R_2$ together form an alkylene radical containing 4 or 5 carbons in which a methylene radical can be replaced by O or NRx in which Rx is H or alkyl, R°° is H, alkyl or optionally substituted phenyl as defined for R°, and n in R° is 0 to 2, and R is a group:

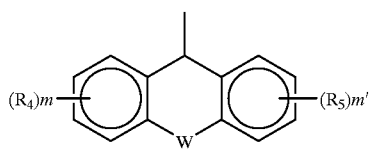

in which W is a bond, O, S, —(CH$_2$)$_2$—, —CH=CH—, or NR" and $R_4$ and $R_5$ are alkyl, alkenyl or alkynyl (2 to 6 carbons), halogen, CN, NO$_2$, CF$_3$, trimethylsilyl, ORa, SRra, SORa, SO$_2$Ra, NRaRb, NRaCORb, NRaCOORb, COORa or CONRaRb in which Ra and Rb are defined as above with the exception of being substituted phenyl and m and m' ranging from 0 to 4;

d) or else $R_1$ and $R_2$ can also be alkyl substituted by CO-alkyl-NRaRb, CON(R'a)alkylORa or CON(R'a)alkylCONRaRb, phenyl (optionally substituted by alkyl, alkyloxy, halogen or trifluoromethyl), alkenyl (2 to 6 carbons), alkynyl (2 to 6 carbons), SO$_2$Ra, haloacyl, CO-alkyl-NRaRb or CON(Ra)alkylCONRaRb, or $R_1$ and $R_2$ together form an alkylene radical containing 4 or 5 carbons in which a methylene radical can be replaced by O or NRx in which Rx is H or alkyl and Ra and Rb are defined as above for the general formula (V) or together form a chain as defined for $R_1$ and $R_2$ and R'a is defined as Ra for the general formula (V), $R_3$ is defined as above for the general formula (V) or represents alkenyl, R°° is H and n in R° is 0 to 2, and R is —CR$_6$R$_7$R$_8$ or —CH$_2$—CR$_6$R$_7$R$_8$ in which $R_6$ is H or OH and $R_7$ and $R_8$ are substituted benzyl or phenyl, or cycloalkyl or cycloalkylmethyl (5 to 7 carbons);

e) or else $R_1$ and $R_2$ can also be defined as above in c) with the exception of simultaneously representing H, X and Y are defined as for the general formula (V) or can also be alkyl or alkenyl (2 to 6 carbons), Z is defined as for the general formula (V) with the exception of being NR", R°° and n in R° are defined as above in c) and R is optionally substituted heteroaryl, naphthyl or phenyl; or else 2) Products of General Formula

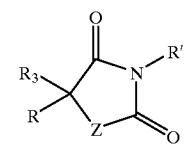

(V')

in which Z is O, S or NR" or CR$_4$R$_5$ in which R", $R_4$ and $R_5$ are H, alkyl or optionally substituted phenyl or phenylalkyl (in which the alkyl part contains 1 to 4 carbons), or else R" is —COR$_6$, —COOR$_6$ or —CONR$_4$R$_5$ and $R_6$ is alkyl or optionally substituted phenyl or phenylalkyl (in which the alkyl part contains 1 to 4 carbons), R' is defined as for the formula (V), $R_3$ and R is defined as for the general formula (V) in b), and R°° is H and n in R° is 0 to 3;

it being understood that, except when especially mentioned, the alkyl portions contain 1 to 6 carbons.

By way of example, antagonists of NK1 receptors of the dialkylenepiperidino derivatives class can be products of general formula:

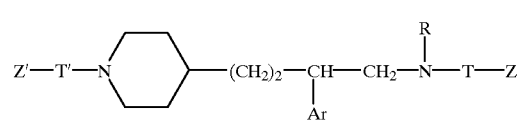

(VI)

in which:

Ar is optionally mono- or polysubstituted (by halogen, alkyl or alkyloxy (1 to 3 carbon atoms), OH or trifluoromethyl) phenyl, or thienyl, pyridyl or naphthyl which can be substituted by halogen, or benzothienyl or indolyl, and R is a hydrogen atom or an alkyl radical (1 to 6 carbon atoms), or an aminoalkyl radical of structure —(CH$_2$)$_n$—NH$_2$ in which n is equal to 2 to 6, T is a —CO—, —CO—O—, —CO—NH— or —CS—NH— group, and T' is a bond except if Z' is a hydrogen atom, or represents a —CH$_2$—, —CO—, —CH$_2$—O— or —CO—O— radical, Z and Z', which are identical or different, are H, straight or branched alkyl (1 to 6 carbon atoms), phenylalkyl, in which the alkyl part contains 1 to 3 carbon atoms, optionally mono- or polysubstituted on the phenyl by halogen, OH, alkyl or alkyloxy (1 to 4 carbon atoms), pyridylalkyl or naphthylalkyl or pyridylthioalkyl or 1-methyl-2-imidazolylthioalkyl, in which the alkyl part contains 1 to 3 carbon atoms, styryl, 1-oxo-3-phenyl-2-indanyl, or an unsubstituted, mono- or polysubstituted heteroaromatic or aromatic group or an α-hydroxybenzyl group or an α-alkylbenzyl group in which the alkyl part contains 1 to 3 carbon atoms.

Products of the substituted piperidine quaternary salts class can be especially products of general formula:

(VII)

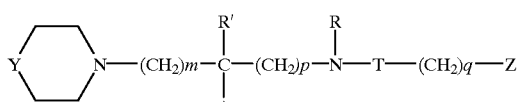

in which:

Y is Y'—CXX'—CX" or Y'—(CH$_2$)$_x$—CX° in which Y' is phenyl, which can be substituted (by 1 or more H, halogen, OH, alkyloxy, alkyl or CF$_3$), cycloalkyl, pyridyl or thienyl, X is H if X' forms a bond with X", or else X and X' form oxo and X" is H, x is 0 and X° is H or else x is 0 or 1 and X° is OH, alkyloxy, acyloxy, carboxyl, carbalkoxy, CN, —NH—CO-alkyl, mercapto or alkylthio, or else X° forms a bond with the carbon atom of the piperidine, Q is alkyl or benzyl, R' is H and R is H or alkyl, or else Y is Y'—CX° in which Y' is defined as above, X° forms an ethylenyl radical with Q and R' and R form, together with the atoms to which they are attached, a piperidino radical, A$^-$ is a Cl$^-$, Br$^-$, I$^-$, acetate, methanesulphonate or p-toluenesulphonate anion, Ar is defined as for the general formula (VI) with the exception of substituted naphthyl or pyridyl, or represents N-alkylindolyl, T is C=O, CO—O, —(C=O)—NH— or —(C=S)—NH—, and Z is defined as for the general formula (VI) or represents α-hydroxyalkylbenzyl or phenyl substituted by CF$_3$, naphthyl substituted by substituents as listed for phenyl or an optionally substituted mono-, di- or tricyclic heteroaromatic or aromatic group and m is 2 or 3;

and, among these quaternary salts, especially the product of formula:

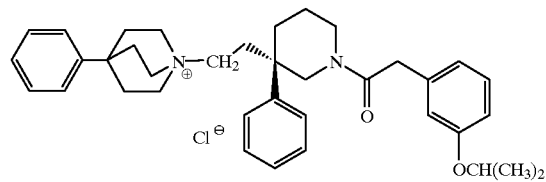

As non-limiting examples, antagonists of NK2 receptors can be especially derivatives of the arylalkylamine class, the α-substituted polypeptide class or of the class of piperidine derivatives, and the like.

By way of example, antagonists of NK2 receptors of the arylalkylamine class can be products of general formula:

(VIII)

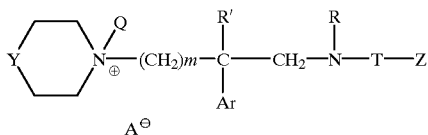

in which:

1) Y is a group >N—CXX'—Ar', >CH—CXX'—Ar' or >C=CX—Ar' in which X is H and X' is H or OH or X and X' together form an oxo radical or a dialkylaminoalkyloxy-imino radical in which the alkyl parts contain 1 to 4 carbon atoms and the alkyloxy part contains 2 or 3 carbon atoms, Ar and Ar' are independently thienyl or phenyl, optionally mono- or polysubstituted (by halogen, alkyl or alkyloxy (1 to 3 carbon atoms), trifluoromethyl, hydroxyl or methylenedioxy) or imidazolyl, or else Ar can be benzothienyl or naphthyl optionally substituted by halogen, biphenyl or indolyl, which can carry a benzyl group on the nitrogen atom, R' is a hydrogen atom, an alkyl radical (1 to 4 carbon atoms), or an alkyl radical (2 or 3 carbon atoms) substituted (by piperidino, 4-benzylpiperidino or dialkylamino in which the alkyl parts contain 1 to 4 carbon atoms, R and T are defined as for the general formula (VI) and Z is H, straight or branched alkyl (1 to 6 carbon atoms), phenylalkyl in which the alkyl part contains 1 to 3 carbon atoms, optionally mono- or polysubstituted on the phenyl by halogen, OH, alkyl or alkyloxy (1 to 4 carbon atoms), pyridylalkyl or naphthylalkyl or pyridylthioalkyl or 1-methyl-2-imidazolylthioalkyl in which the alkyl part contains 1 to 3 carbon atoms, styryl, 1-oxo-3-phenyl-2-indanyl or an unsubstituted, mono- or polysubstituted heteroaromatic or aromatic group, and m is an integer from 1 to 3, p is equal to 1 and q is equal to 0, or else 2) Y is a group >N—Ar' in which Ar' is a phenyl radical which can be substituted 1 or more times (by halogen, OH, alkyloxy or alkyl (1 to 4 carbon atoms) or trifluoromethyl), pyrimidinyl or pyridyl, a >N-cycloalkyl group (3 to 7 carbon atoms), or else a >CX—(CH$_2$)$_x$—Ar' group in which Ar' is defined as above with the exception of representing pyrimidinyl, or represents thienyl, X is OH, alkyloxy (1 to 4 carbon atoms), hydroxyalkyl or acyloxy in which the alkyl part contains 1 to 3 carbon atoms, phenacyloxy, carboxyl, carbalkoxy (1 to 4 carbon atoms), cyano, aminoalkylene (1 to 3 carbon atoms), amino, alkylamino or dialkylamino in which the alkyl parts contain 1 to 4 carbon atoms, acylamino (2 to 7 carbon atoms), acylaminoalkyl in which the alkyl parts contain 1 to 3 carbon atoms, acyl, —SH or alkylthio in which the alkyl part contains 1 to 4 carbon atoms and x is 0 or 1, or else a =C—(CH$_2$)$_x$—Ar' group in which Ar' is defined as above, T is defined as in 1), and Z is defined as in 1) with the exception of representing 1-methyl-2-imidazolylthioalkyl or 1-oxo-3-phenyl-2-indanyl, or represents phenylalkyl substituted by trifluoromethyl or naphthylalkyl in which the alkyl part contains 1 to 3 carbon atoms and optionally substituted on the naphthyl ring by a halogen atom or by a trifluoromethyl, OH, alkyl or alkyloxy (1 to 4 carbon atoms) radical, Ar is thienyl or phenyl, optionally mono- or polysubstituted (by halogen, alkyl or alkyloxy (1 to 4 carbon atoms), or trifluoromethyl) or benzothienyl, naphthyl or indolyl, which can carry an alkyl group (1 to 3 carbon atoms) on the nitrogen atom, R' is a hydrogen atom, R is a hydrogen atom or an alkyl radical (1 to 6 carbon atoms), and m is an integer equal to 2 or 3, p is equal to 1 and q is equal to 0, or else 3) Y is a >N—Ar' or >N—CH$_2$—Ar' group in which Ar' is defined as above in 2), or else a >CX—(CH$_2$)$_x$—Ar' group as defined above, X being OH, alkyloxy, acyloxy or carbalkoxy (1 to 4 carbon atoms), carboxyl, cyano, optionally mono- or disubstituted (by alkyl, hydroxyalkyl or acyl (1 to 4 carbon atoms)) amino, pyrrolidino, piperidino, or morpholino, —SH or alkylthio in which the alkyl part contains 1 to 4 carbon atoms and x is 0 or 1, or else a =C—(CH$_2$)$_x$—Ar' group in which Ar' is defined as above, Ar is defined as above in 2) with the exception of representing a substituted indolyl radical, R and R' together form a

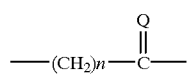

chain in which Q is an oxygen atom or 2 hydrogen atoms,

T is —CO— or —CH$_2$— and

Z is phenyl or naphthyl optionally mono- or polysubstituted by halogen, trifluoromethyl, OH or alkyl (1 to 4 carbon atoms), or by alkyloxy (1 to 4 carbons) when Z is phenyl, pyridyl, thienyl, indolyl, quinolyl, benzothienyl or imidazolyl, or an unsubstituted, mono- or polysubstituted heteroaromatic or aromatic group, or, when T is CO, —(CH$_2$)q-Z can be benzyl in which the methyl radical is substituted by OH, alkyl or alkyloxy (1 to 4 carbons) or substituted on the ring by halogen, trifluoromethyl, OH, alkyl or alkyloxy (1 to 4 carbons), and m is an integer equal to 2 or 3, p is equal to 1 or 2, n is equal to 0 to 3 and q is equal to 0 to 3, it being understood that if p=2:n=1 and Q represents 2H; or else 4) Y is a group Ar'—X— in which Ar' represents thienyl or phenyl, optionally mono- or polysubstituted (by halogen, alkyl or alkyloxy (1 to 3 carbons), trifluoromethyl, hydroxyl or methylenedioxy), pyridyl or imidazolyl, optionally substituted by an alkyl radical, and X is an oxygen or sulphur atom or a sulphonyl, sulphinyl, —NH—, >N—CO—Alk, >N—Alk or >N—Alk—NX$_1$X$_2$ radical in which Alk is alkyl or alkylene (1 to 3 carbons) and X$_1$ and X$_2$ are H or alkyl (1 to 3 carbons) or form, with the nitrogen atom, a piperidine, pyrrolidine or morpholine ring, R' is a hydrogen atom, an alkyl radical (1 to 4 carbons) or an aminoalkyl radical in which the straight-chain alkyl part contains 2 or 3 carbon atoms and the amino group can be dialkylamino in which the alkyl parts contain 1 to 4 carbon atoms, piperidino or 4-benzylpiperidino, Ar, R and T are defined as in 1), Z is defined as above 1) or represents α-hydroxy-benzyl or α-alkylbenzyl in which the alkyl part contains 1 to 3 carbon atoms, and m, p and q are defined as above in 2), or else 5) Y is a group >CX—(CH$_2$)$_x$—Ar' in which Ar' is thienyl or phenyl, optionally mono- or polysubstituted (by halogen, alkyl or alkyloxy (1 to 4 carbons), trifluoromethyl or hydroxyl) or pyridyl, x is 0 or 1, and X is —NH—CO-alkyl in which the alkyl part contains 1 to 6 carbons, m is 2 or 3, p is 1 and q is equal to 0, Ar, T and Z are defined as in 2), R' is H and R is H or alkyl;

and, among these products, the product of Example 2 mentioned below, which is a specific antagonist of NK2 receptors, is described more particularly by X. Emonds-Alt et al., Life Science, 50, PL 100 to PL 106 (1992).

By way of example, antagonists of NK2 receptors of the α-substituted polypeptide class can be products of general formula:

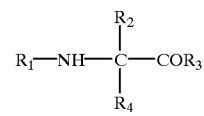

(IX)

in which

R$_1$ is a hydrogen atom or an N-terminal group consisting of 0 to 4 amino acids, R$_2$ is an amino acid side chain, apart from glycine, R$_3$ is a C-terminal group consisting of 0 to 4 amino acids or an OH or OR radical in which R is a straight or branched alkyl or cycloalkyl radical containing 1 to 6 carbon atoms, R$_4$ is an amino acid side chain, apart from glycine, or a —CH=CH$_2$, —CH≡CH, —CH$_2$—CH=CH$_2$, —CH$_2$—CH≡CH, —CH$_2$—Ar, —CH$_2$—OR, —CH$_2$—OAr, —(CH$_2$)$_n$CO$_2$R or —CH$_2$—NR$_5$R$_6$ radical, n being an integer from 0 to 3, R being H or a lower alkyl radical and Ar being an unsubstituted or substituted, mono- or polycyclic, aromatic or hydroaromatic heterocycle or carbocycle, it being understood that R$_1$ and R$_2$ cannot comprise more than 4 amino acid residues in total.

By way of example, antagonists of NK2 receptors of the class of piperidine derivatives can be products of general formula:

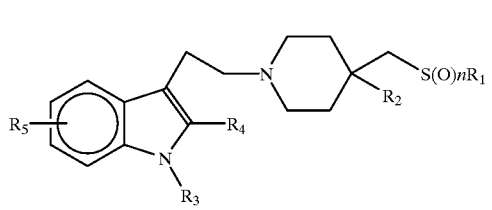

(X)

in which $R_1$ is phenyl optionally substituted by 1 or 2 alkyl, alkyloxy, $CF_3$ or halogen, $R_2$ is H, OH or alkyl, $R_3$ is H or alkyl, $R_4$ is H, alkyl or alkyloxy, and $R_5$ is H, alkyl, $CF_3$, CN or halogen and n is 0 to 2, the alkyl radicals having 1 to 4 carbons;

and, among these products, more especially 1-[2-(5-fluoro-1H-indol-3-yl)ethyl]-4-[(phenylsulphinyl)methyl]-4-piperidinol.

The products of general formulae (I) to (X) can be prepared according to the methods described in Patent Applications EP 429,366, EP 514,273, EP 514,275 WO 90/05525, WO 90/05729, WO 91/18899, WO 91/09844, WO 92/01688, WO 92/06079, WO 92/15585, WO 92/12151, WO 92/20661, WO 92/20676, WO 92/21677, WO 93/00330, WO 93/00331, WO 93/01159, WO 93/01169, WO 93/01165, WO 93/01170, WO 93/06099, WO 93/09116, WO 93/10073, WO 93/18023, WO 93/19064, WO 93/21155, WO 93/21181, WO 93/23380, EP 499,313, EP 394,989, EP 443,132, EP 482,539, EP 517,589, EP 520,555, EP 522,808, EP 528,495, EP 532,456, EP 533,280, EP 536,817, EP 545,478, EP 559,538, WO 91/18878, WO 92/17449, EP 428,434, EP 474,561, EP 512,901, EP 512,902, EP 515,240, FR 2,678,267, WO 92/19254, WO 93/14084 or WO 93/21155 or by analogy with these methods.

The thiapyranopyrrole derivative of general formula:

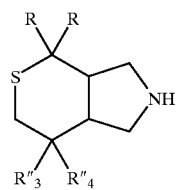

(I'e)

in which the R, $R''_3$ and $R''_4$ radicals are defined as above, used as starting material for the preparation of the products in which the A-B bicycle corresponds to the general formula (Ie), can be prepared according to the following methods:

when $R''_4$ is a fluorine atom, the product of general formula (I'e) can be prepared by fluorination of a thiapyranopyrrole derivative of general formula:

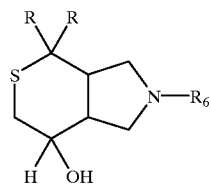

(I''e)

in which R is defined as above and $R_6$ is a protective radical, and then removal of the $R_6$ radical.

The $R_6$ protective radical can be any amino protective group which is compatible with the reaction and whose introduction and removal does not detrimentally affect the remainder of the molecule. Mention may be made, by way of example, of alkyloxycarbonyl, benzyloxycarbonyl, optionally substituted benzyl, formyl, chloroacetyl, trichloroacetyl, trifluoroacetyl, vinyloxycarbonyl, phenoxycarbonyl, 1-chloroethoxycarbonyl or chlorocarbonyl groups.

The reaction is advantageously carried out using a fluorinating agent such as a sulphur fluoride [morpholinosulphur trifluoride, sulphur tetrafluoride (J. Org. Chem., 40, 3808 (1975)), diethylaminosulphur trifluoride (Tetrahedron, 44, 2875 (1988)), phenylsulphur trifluoride (J. Am. Chem. Soc., 84, 3058 (1962)], such as selenium tetrafluoride (J. Am. Chem. Soc., 96, 925 (1974)) or such as tetrafluorophenylphosphorane (Tet. Let., 907 (1973), the reaction being carried out in an organic solvent such as a chlorinated solvent (dichloromethane or dichloroethane, for example) at a temperature between −30 and 30° C. The subsequent removal of the $R_6$ protective radical is carried out according to the usual methods. Especially according to the methods described by T. W. Greene, Protective Groups in Organic Synthesis, A. Wiley—Interscience Publication (1981), or by McOmie, Protective Groups in Organic Chemistry, Plenum Press (1973).

when $R''_3$ is a phenyl radical optionally substituted in the 2-position by an alkyl or alkyloxy radical and $R''_4$ is a hydroxyl radical, the product of general formula (I'e) can be obtained by reacting an organometallic compound of general formula:

$$R''_3-M \qquad (I'''e)$$

in which $R''_3$ is defined as above and M represents lithium, cerium or a radical MgX in which X is a halogen atom, with the corresponding thiapyranopyrrolone derivative of general formula:

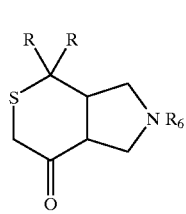

(I^{IV}e)

in which R and $R_6$ are defined as above, and then optionally removal of the $R_6$ protective radical.

The reaction is carried out in anhydrous medium, under the usual conditions for the reaction of organometallic compounds with a ketone, which do not affect the remainder of the molecule. Especially in an ether (for example, tetrahydrofuran or ethyl ether), optionally in the presence of anhydrous cerium chloride, at a temperature between −78 and 30° C.

The thiapyranopyrrole derivatives of general formula (I'e) or (I"e) in which R"$_3$ is a hydrogen atom and R"$_4$ is a hydroxyl radical can be obtained by respectively reducing the derivative of general formula (I$^{IV}$e) or the corresponding thiapyranopyrrolone derivative of general formula (I'e) for which R$_3$ and R$_4$ together form an oxo radical. The reduction is advantageously carried out using an alkali metal borohydride (sodium borohydride, lithium tri-sec-butylborohydride) in a solvent such as an alcohol (methanol or ethanol, for example) or an ether (tetrahydrofuran) in basic medium, at a temperature between −20 and 50° C.

The thiapyranopyrrolone derivative of general formula (Ie) in which R"$_3$ and R"$_4$ together form an oxo radical or the thiapyranopyrrolone derivative of general formula (I$^{IV}$e) can be prepared from the thiapyranone of general formula:

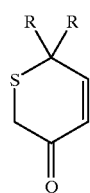

(I$^V$e)

in which R is defined as above, and then introducing the R$_6$ protective radical if it is desired to obtain a product of general formula (I$^{IV}$e).

The potentialization of the combinations of antagonists of NK1 receptors and of antagonists of NK2 receptors was revealed in the following way:

Capsaicin, administered at a low dose, causes the release of various neuropeptides, especially substance P and neurokinin A in the primary afferent fibres of various peripheral tissues.

Antagonists of substance P are known to block the effects of an agonist of NK1 receptors and antagonists of neurokinin A are known to block the effects of an agonist of NK2 receptors. However, when these agonists are replaced by capsaicin, the action usually observed with agonists becomes extremely weak or disappears completely.

It has been shown, in an identical test, that the administration of a combination of antagonist products of substance P and antagonists of neurokinin A blocks the effects of capsaicin, or, in other terms, causes the reappearance of the action usually observed with NK1 and NK2 agonists.

Methods

I) Inhibition of the Contraction of the Rat Bladder, In Vivo, Due to a Topical Administration of Capsaicin Principle The local application of capsaicin on the rat bladder, in vivo, triggers a dose-dependent contraction due mainly to release of substance P and neurokinin A acting respectively on NK1 and NK2 receptors. Pretreatment with an NK1 or NK2 antagonist, or their combination, should thus inhibit the submaximal contraction caused by capsaicin.

Technique

The animals used are female Sprague-Dawley rats weighing from 210 to 260 g which are anaesthetized by ethyl carbamate and whose rectal temperature is maintained at 380° C. Pretreatment is carried out with chlorisondamine (Ecolid®), 0.5 mg/kg i.v., in order to suppress any spontaneous or reflex vesical contraction. The intravesical pressure is continuously measured by virtue of a catheter introduced urethrally and connected to a strain gauge pressure sensor itself connected to an amplifier and to a graph recorder. This pressure is adjusted to a value of 3 mm of mercury at the beginning of the experiment by filling with 0.9% NaCl solution. A low laparotomy is carried out in order to access the bladder.

Each antagonist (NK1 or NK2) or their combination is injected into a jugular vein 40 minutes after administration of chlorisondamine.

Five minutes after treatment with the antagonist(s), a capsaicin solution (250 ng in 10 ml) is applied on the rounded surface of the bladder for 3 minutes, by virtue of its deposition on a small piece of filter paper placed beforehand on this region. The % of inhibition by the antagonist(s) of the contraction due to capsaicin is calculated by comparing the rise in the intravesical pressure observed in the treated batches with respect to the capsaicin control batch.

Results

The products studied are denoted as defined below:

Antagonist of NK1 receptors:
  Product 1: (3aR,7aR)-2-(1-imino-2-(2-methoxyphenyl) ethyl]-7,7-diphenylperhydroisoindol-4-one:

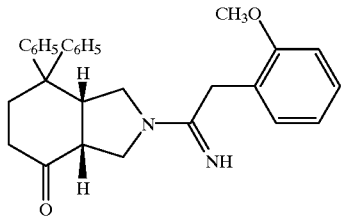

Antagonist of NK2 receptors:
  Product 2: N-methyl-[4-(4-phenyl-4-acetamidopiperidinyl)-2-(3,4-dichlorophenyl)butyl] benzamide:

TABLE I

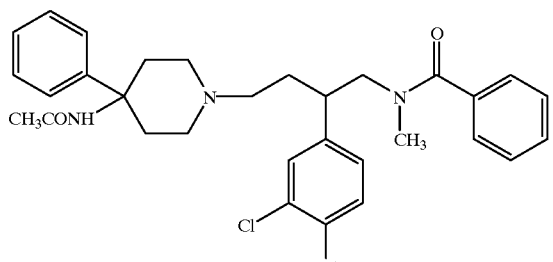

| Treatment | intravesical pressure Δ (mm of Hg) | Inhibition with respect to the control batch |
|---|---|---|
| Capsaicin controls 250 ng topically | 5.5 ± 0.9 | |
| Product 1 | 5.3 ± 1.1 (not significant) | 4% |
| Product 2 | 5.0 ± 0.6 (not significant) | 9% |
| Product 1 + Product 2 | 1.4 ± 0.2 (P < 0.001) | 74% |

Product 1 and Product 2, administered alone at a dose of 0.5 mg/kg intravenously, did not inhibit the contraction caused by capsaicin. In contrast, their combination markedly reduced (74%) the action of capsaicin in an entirely significant way (P<0.001).

II) Inhibition of Bronchospasm Caused by Capsaicin Administered Intravenously to Guinea Pigs Principle The i.v. injection of capsaicin in guinea pigs triggers a bronchospasm due mainly to release of substance P and neurokinin A acting respectively on NK1 and NK2 receptors. Pretreatment with an NK1 or NK2 antagonist, or their combination, should thus inhibit this bronchospasm.

Technique

The animals used are female Hartley guinea pigs weighing from 330 to 480 g anaesthetized with ethyl carbamate and whose rectal temperature is maintained at 370° C. After starting up artificial respiration (0.1 ml of air/100 g of body weight, 50 insufflations/min), the animals receive a curariform (pancuronium bromide, 0.8 mg/kg i.v.) to improve ventilation, and then chlorisondamine (Ecolid®), 0.5 mg/kg i.v., in order to block autonomous nervous system reflexes. The insufflation pressure is continuously measured in a side tube placed on the trachial cannula, by virtue of a strain gauge pressure sensor connected to an amplifier and to a graph recorder.

Capsaicin (2.5 µg/kg i.v. bolus) is injected 25 minutes before, and then 5 minutes after, i.v. treatment with the antagonist (NK1 or NK2) or their combination. All these injections are carried out in a jugular vein.

The % of inhibition by the antagonist(s) of bronchospasm due to capsaicin is calculated by comparing the increase in the maximum intrachial insufflation pressure observed at the second capsaicin injection with respect to the first.

Results

The products studied are denoted as defined below:

Antagonists of NK1 receptors:
Product 3: (3aS,4S,7aS)-7,7-diphenyl-4-(2-methoxyphenyl)-2-[(S)-2-(2-methoxyphenyl)propionyl]perhydroisoindol-4-ol

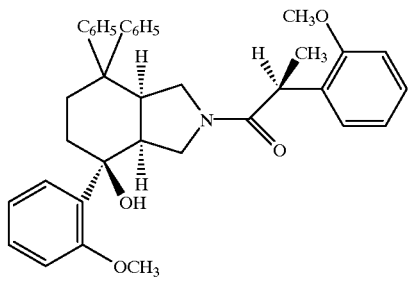

Product 4: 3-[(2-methoxyphenyl)methylamino]-2-phenylpiperidine

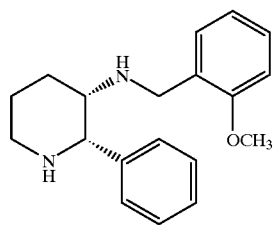

Antagonist of NK2 receptors:
Product 2: N-methyl-[4-(4-phenyl-4-acetamidopiperidinyl)-2-(3,4-dichlorophenyl)butyl]benzamide.

TABLE II

| Treatment | Insufflation pressure Δ due to capsaicin (mm of Hg) | | Variation in % of the response to capsaicin |
|---|---|---|---|
| | Before treatment | After treatment | before/after treatment |
| Capsaicin controls 250 ng intravenously | 26 ± 5 | 27 ± 4 (not significant) | +4% |
| Product 3 | 26 ± 3 | 25 ± 2 (not significant) | −4% |
| Product 2 | 27 ± 3 | 26 ± 5 (not significant) | −4% |
| Products 2 + 3 | 34 ± 3 | 11 ± 2 (P < 0.001) | −68% |
| Product 4 | 25 ± 5 | 28 ± 7 (not significant) | +13% |
| Product 2 | 27 ± 3 | 26 ± 5 (not significant) | −4% |
| Products 2 + 4 | 23 ± 6 | 0.5 ± 0.2 (P < 0.001) | −98% |

Products 3 and 4, administered alone at a dose of 1 mg/kg intravenously, did not inhibit bronchospasm caused by capsaicin. It is likewise the case for Product 2 (NK2 antagonist) at the same dose. In contrast, the combination of Products 2 and 3 reduced bronchospasm by 68% and the combination of Products 2 and 4 reduced bronchospasm by 98%.

Thus, as shown in Tables I and II, none of the antagonists administered alone is capable of inhibiting the effects of capsaicin. On the other hand, the combination of antagonists of NK1 and NK2 receptors powerfully antagonizes the spasmogenic effects of capsaicin on the bladder and bronchial tubes.

The following example illustrates the preparation of products which can be used in the combination.

Preparation of Product 1

0.025 g of 1-hydroxybenzotriazole, 0.38 g of (S)-2-(2-methoxyphenyl)propionic acid and 0.32 cm³ of diisopropylethylamine are added to a suspension of 0.8 g of (3aS,4S,7aS)-7,7-diphenyl-4-(2-methoxyphenyl)perhydroisoindol-4-ol hydrochloride in 60 cm³ of dry dichloromethane, this solution is then cooled to +5° C. and a suspension of 0.43 g of 1-[3-(dimethylamino)propyl]-3-ethylcarbodiimide in 10 cm³ of dry dichloromethane is rapidly added. The reaction mixture is stirred for 2 hours at +5° C. and for 2 hours at room temperature, washed with 20 cm³ of water, then washed with 20 cm³ of a saturated aqueous sodium chloride solution (twice), dried over magnesium sulphate and concentrated to dryness under reduced pressure (2.7 kPa). The residue is chromatographed on a column of Merck silica gel (particle size 0.04–0.06 mm, diameter 2.8 cm, height 20 cm), eluting under a pressure of 0.5 bar of nitrogen with a mixture of cyclohexane and ethyl acetate (80/20 by volume) and collecting 25 cm³ fractions. Fractions 9 to 15 are combined and then concentrated to dryness under reduced pressure (2.7 kPa). The residue is crystallized from a mixture of acetonitrile and diisopropyl ether. There is obtained 0.17 g of (3aS,4S,7aS)-7,7-diphenyl-4-(2 -methoxyphenyl)-2-[(S)-2-(2-methoxyphenyl)propionyl]perhydroisoindol-4-ol in the form of white crystals melting at 244° C.

(3aS,4S,7aS)-7,7-Diphenyl-4-(2-methoxyphenyl) perhydroisoindol-4-ol hydrochloride can be prepared in the following way:

A solution of 100 cm³ of a 5.2N solution of hydrochloric acid in dioxane is added at room temperature to a solution of 7.63 g of (3aS,4S,7aS)-7,7-diphenyl-4-(2-methoxyphenyl)-2-(tert-butoxycarbonyl)perhydroisoindol-4-ol in 66 cm³ of dioxane. The reaction mixture is stirred for 1 hour at this temperature and then concentrated to dryness under reduced pressure (2.7 kPa). The residue is washed with acetonitrile, filtered off and then dried. There are obtained 4.88 g of (3aS,4S,7aS)-7,7-diphenyl-4-(2-methoxyphenyl)perhydroisoindol-4-ol hydrochloride in the form of white crystals melting at 271° C. (Maquenne block).

(3aS,4S,7aS)-7,7-Diphenyl-4-(2-methoxyphenyl)-2-(tert-butoxycarbonyl)perhydroisoindol-4-ol can be prepared in the following way:

A suspension of 2-methoxyphenylmagnesium bromide (prepared from 75.3 g of 2-bromoanisole and 9.8 g of magnesium) in 100 cm³ of dry tetrahydrofuran is added dropwise at room temperature with stirring to a suspension of 20 g of (3aS,7aS)-7,7-diphenyl-2-(tert-butoxycarbonyl)perhydroisoindol-4-one and 31.6 g of anhydrous cerium chloride in 250 cm³ of dry tetrahydrofuran. The reaction mixture is stirred at room temperature for 24 hours, treated with 400 cm³ of a saturated aqueous ammonium chloride solution, diluted with 200 cm³ of ethyl acetate, washed with 300 cm³ of water (twice) and then with 300 cm³ of a saturated aqueous sodium chloride solution, dried over magnesium sulphate, filtered and concentrated to dryness under reduced pressure (2.7 kPa). The residue is chromatographed on a column of Merck silica gel (particle size 0.04–0.06 mm, diameter of 5.8 cm, height 26.5 cm), eluting under a pressure of 0.5 bar of nitrogen with a mixture of cyclohexane and ethyl acetate (80/20 by volume) and collecting 100 cm³ fractions. Fractions 9 to 29 are combined and concentrated to dryness under reduced pressure (2.7 kPa). There are obtained 17.82 g of (3aS,4S,7aS)-7,7-diphenyl-4-(2-methoxyphenyl)-2-(tert-butoxycarbonyl)perhydroisoindol-4-ol in the form of a white foam.

Proton NMR spectrum (d₆-DMSO): 1.36 (s, 9H, —C(CH₃)₃), 1.54 (dmt, J=14, 1H, equatorial H of the —CH₂— in the 5-position), 2.3 (dmt, J=14, 1H, equatorial H of the —CH₂— in the 6-position), 2.34 (td, J=14 and 2.5, 1H, axial H of the —CH₂— in the 5-position), 3.07 (td, J=14 and 2.5, axial H of the —CH₂— in the 6-position), 3.49 (s, 3H, —OCH₃), 2.6 to 3.6 (mt, other —CH₂— and —CH), 6.85 to 7.7 (mt, 14H, aromatic protons).

(3aS,7aS)-7,7-Diphenyl-2-(tert-butoxycarbonyl)perhydroisoindol-4-one can be obtained in the following way:

34.3 cm³ of triethylamine, 58.6 g of di-tert-butyl dicarbonate and then 2.98 g of 4-dimethylaminopyridine are added at room temperature with stirring to a suspension of 80 g of (3aS,7aS)-7,7-diphenylperhydroisoindol-4-one hydrochloride in 400 cm³ of dry dichloromethane. The reaction mixture is stirred at room temperature for 24 hours, washed with 100 cm³ of an aqueous citric acid solution, then with 100 cm³ of an aqueous sodium hydrogencarbonate solution, then with 100 cm³ of a saturated aqueous sodium chloride solution, dried over magnesium sulphate and concentrated to dryness under reduced pressure (2.7 kPa). There are obtained 106.5 g of (3aS,7aS)-7,7-diphenyl-2-(tert-butoxycarbonyl)perhydroisoindol-4-one in the form of an orange foam.

Proton NMR spectrum (d₆-DMSO): 1.4 (s, 9H, —C(CH₃)₃), 2.11 (td, J=15 and 7.5, 1H, axial H of the —CH₂— in the 5-position), 2.3 (dt, J=15 and 3.5, 1H, equatorial H of the —CH₂— in the 5-position), 2.75 to 2.9 (mt, 4H, —CH₂— in the 6-position and —CH₂— in the 1-position), 3.26 (dd, J=7.5 and 7, 1H —CH in the 3a-position), 3.35 (dd, J=11 and 7, 1H, 1H of the —CH₂— in the 3-position), 3.97 (mt, 1H, —CH in the 7a-position), 4.1 (d, J=11, 1H, the other H of the —CH₂— in the 3-position), 7.1 to 7.7 (mt, 10H, aromatic protons).

(3aS,7aS)-7,7-Diphenylperhydroisoindol-4-one hydrochloride can be obtained in the following way:

50 cm³ of 4N aqueous sodium hydroxide are added slowly, with stirring, to a suspension of 20 g of (3aRS,7aRS)-7,7-diphenylperhydroisoindol-4-one hydrochloride in 250 cm³ of ethyl acetate; stirring is continued until the starting material has disappeared. The organic solution is washed with 100 cm³ of distilled water and with 100 cm³ of a saturated sodium chloride solution, dried over magnesium sulphate and filtered. A solution of 9.3 g of D-(−)-mandelic acid in 50 cm³ of ethyl acetate is added with stirring to the solution thus obtained. The crystals formed are filtered filtered off, washed with 50 cm³ of ethyl acetate (twice) and dried. The crystals are taken up in a solution of 220 cm³ of acetonitrile and 60 cm³ of distilled water and the mixture is brought to reflux with stirring for 15 minutes; the crystals formed are filtered and again crystallized from a mixture of 100 cm³ of acetonitrile and 35 cm³ of distilled water. There are obtained 6.4 g of (3aS,7aS)-7,7-diphenylperhydroisoindol-4-one D-mandelate.

50 cm³ of 1N aqueous sodium hydroxide are added to 6.4 g of (3aS,7aS)-7,7-diphenylperhydroisoindol-4-one D-mandelate in solution in 100 cm³ of ethyl acetate; the reaction mixture is stirred at room temperature until the starting material has disappeared; the organic solution is washed with 50 cm³ of distilled water, with 50 cm³ of a saturated aqueous sodium chloride solution, dried over magnesium sulphate and filtered; it is acidified with stirring by addition of 2 cm³ of a 9N solution of hydrochloric acid in ethanol; the crystals obtained are filtered off, washed with ethyl acetate and then with isopropyl ether and dried. There are obtained 4.24 g of (3aS,7aS)-7,7-diphenylperhydroisoindol-4-one hydrochloride in the form of white crystals melting at 270° C. with decomposition.

(S)-2-(2-Methoxyphenyl)propionic acid can be prepared, by analogy with the methods described by D. A. Evans e t al., Tetrahedron, 44, 5525, (1988), according to the following procedure:

1.52 g of lithium hydroxide are added to a solution, cooled to +5° C., of 4.1 g of (4S,5S)-4-methyl-5-phenyl-3-[(S)-2-(2-methoxyphenyl)propionyl]oxazolidin-2-one in 60 cm³ of tetrahydrofuran and 30 cm³ of water. The reaction mixture is stirred for 3 hours at this temperature and then, after returning to room temperature, ethyl acetate is added, separation is carried out by settling, the aqueous phase is acidified with a 1N aqueous hydrochloric acid solution, extracted with ethyl acetate, the organic phase is dried over magnesium sulphate and concentrated to dryness under reduced pressure (2.7 kPa). The solid obtained is recrystallized from hexane, filtered off and dried. There is obtained 0.4 g of (S)-2-(2-methoxyphenyl)propionic acid in the form of white crystals melting at 102° C. $[\alpha]_D^{20}$=+84.6° (c=1, CHCl₃).

(4S,5S)-4-Methyl-5-phenyl-3-[(S)-2-(2-methoxyphenyl)propionyl]oxazolidin-2-one can be obtained in the following way:

19.1 g of sodium 1,1,1,3,3,3-hexamethyldisilazanate are added to a solution, cooled to −50° C., of 10 g of (4S,5S)-4-methyl-5-phenyl-3-[(2-methoxyphenyl)acetyl]oxazolidin-2-one in 150 cm³ of tetrahydrofuran, the mixture is stirred for 45 minutes at this temperature and then 7.72 cm³ of methyl iodide are added. The reaction mixture is then stirred for 15 hours at room temperature, then diluted with ethyl acetate, washed with 50 cm³ of water and then with 50 cm³ of a saturated aqueous sodium chloride solution, dried over magnesium sulphate and concentrated to dryness under reduced pressure (2.7 kPa). The residue obtained is crystallized from isopropyl ether, filtered off and dried. There are obtained 4.2 g of (4S,5S)-4-methyl-5-phenyl-3-[(S)-2-(2-methoxyphenyl)propionyl]oxazolidin-2-one in the form of a white solid.

(4S,5S)-4-Methyl-5-phenyl-3-(2-methoxyphenylacetyl) oxazolidin-2-one can be obtained in the following way:

9.38 g of 2-methoxyphenylacetic acid are added at room temperature to a suspension of 1.89 g of sodium hydride (80% dispersion in petroleum jelly) in 200 cm³ of dry tetrahydrofuran. This suspension is cooled to –30° C., 7.77 cm³ of pivaloyl chloride are added and then a solution, cooled to –78° C., obtained by adding a solution of 35.27 cm³ of 1.6M butyllithium in hexane to a solution, cooled to –78° C., of 10 g of (4S,5S)-4-methyl-5-phenyloxazolidin-2-one in 200 cm³ of dry tetrahydrofuran is finally added. The reaction mixture is stirred for 45 minutes at –30° C. and then, after returning to room temperature, 200 cm³ of a saturated aqueous ammonium chloride solution and then 500 cm³ of ethyl acetate are added; after separating by settling, the organic phase is washed twice with 100 cm³ of water and then twice with 100 cm³ of a saturated aqueous sodium chloride solution, dried over magnesium sulphate and concentrated to dryness under reduced pressure (2.7 kPa). The residue is chromatographed on a column of silica gel (particle size 0.04–0.06 mm, diameter 4.8 cm, height 36 cm), eluting under a pressure of 0.6 bar of nitrogen with a mixture of cyclohexane and ethyl acetate (85/15 and then 80/20 by volume) and collecting 50 cm³ fractions. Fractions 14 to 31 are combined and concentrated to dryness under reduced pressure (2.7 kPa). There are obtained 13.6 g of (4S,5S)-4-methyl-5-phenyl-3-(2-methoxyphenylacetyl) oxazolidin-2-one in the form of a yellow oil.

The combinations according to the invention are particularly advantageous in the fields where Substance P, neurokinin A and NK1 and NK2 receptors are involved. The present invention also relates to the pharmaceutical compositions comprising the synergistic combination consisting of at least one antagonist of NK1 receptors and of at least one antagonist of NK2 receptors in the pure state or in the form of a combination with one or more compatible and pharmaceutically acceptable adjuvants and/or diluents and/or optionally in combination with any other physiologically active, pharmaceutically compatible product.

The compositions according to the invention can be used parenterally, orally, rectally or topically.

The sterile compositions for parenteral administration, which can be especially used in the form of perfusions, are preferably emulsions, suspensions or aqueous or non-aqueous solutions. Water, propylene glycol, a polyethylene glycol, vegetable oils, in particular olive oil, injectable organic esters, for example ethyl oleate, or other suitable organic solvents can be used as solvent or vehicle. These compositions can also contain adjuvants, in particular wetting, isotonizing, emulsifying, dispersing and stabilizing agents. Sterilization can be carried out in several ways, for example by aseptic filtration, by incorporating sterilizing agents in the composition, by irradiation or by heating. They can also be prepared in the form of sterile solid compositions which can be dissolved at the time of use in a sterile injectable medium.

The compositions for rectal administration are suppositories or rectal capsules which contain, beside the active product, excipients such as cocoa butter, semi-synthetic glycerides or poly(ethylene glycol)s.

Gelatin capsules, tablets, pills, powders or granules can be used as solid compositions for oral administration. In these compositions, the active product according to the invention (optionally in combination with another pharmaceutically compatible product) is mixed with one or a number of inert adjuvants or diluents, such as sucrose, lactose or starch. These compositions can also comprise substances other than the diluents, for example a lubricant such as magnesium stearate.

Solutions, suspensions, syrups, elixirs and pharmaceutically acceptable emulsions containing inert diluents such as water or liquid paraffin can be used as liquid compositions for oral administration. These compositions can also comprise substances other than the diluents, for example wetting, sweetening or flavouring products.

The compositions for topical administration can be, for example, creams, ointments or lotions.

In human therapeutics, the combinations according to the invention can be particularly useful in the treatment of pain of traumatic, post-surgical, menstrual or cranial origin, in treatments of anxiety, of psychoses, Parkinson's disease, schizophrenia or of Alzheimer's disease, in muscle-relaxing treatments, in treatments of spasmodic, painful and inflammatory manifestations of the digestive tract (ulcerative colites, irritable bowel syndrome, Crohn's disease), of the urinary tract (cystites) and of the respiratory tract (chronic bronchitis, asthma, rhinites or in gynaecology and in treatments of migraines. The new combinations are also useful in the treatment of rheumatoid arthritis and in disorders due to disturbance of the immune system, in treatments of dermatological inflammations such as psoriasis, herpes, urticarias, eczemas, photodermatoses and in ocular or dental inflammatory disorders.

The combinations according to the invention can also find an application in treatments of cardiovascular disorders such as hypotension, or in the treatment of disorders related to poor growth regulation (dwarfism, secondary hypotrophias of chronic infantile diseases, osteoporosis, graft development).

The doses depend on the desired effect and on the duration of treatment. For an adult, they are generally between 0.25 and 1500 mg of the combination daily taken in stages.

Generally, the doctor will determine the dosage which he considers the most appropriate depending on the age, weight and all the other factors specific to the subject to be treated.

The following example, given as non-limiting, illustrates a composition according to the invention.

EXAMPLE

Tablets containing active product are prepared, according to the usual technique, which have the following composition:

| | |
|---|---|
| (3aS,4S,7aS)-7,7-diphenyl-4-(2-methoxyphenyl)-2-[(S)-2-(2-methoxyphenyl)propionyl]perhydroisoindol-4-ol | 12.5 mg |
| N-methyl-[4-(4-phenyl-4-acetamidopiperidinyl)-2-(3,4-dichlorophenyl)butyl]benzamide | 12.5 mg |
| starch | 83 mg |

| | |
|---|---|
| silica | 30 mg |
| magnesium stearate | 3 mg |

What is claimed is:

1. A synergistic combination comprising at least one product endowed with an antagonist activity towards NK1 receptors and at least one product of non-peptide nature endowed with an antagonist activity towards NK2 receptors.

2. A method for preparing a synergistic combination according to claim 1, which comprises combining a product endowed with an antagonist activity towards NK1 receptors with a product of non-peptide nature endowed with an antagonist activity towards NK2 receptors to form said synergistic combination.

3. A pharmaceutical composition comprising a synergistic combination according to claim 1, wherein said synergistic combination is in the pure state or is in the presence of any compatible and pharmaceutically acceptable adjuvant or diluent.

4. A combination according to claim 1, comprising at least one antagonist of NK1 receptors selected from derivatives of the perhydroisoindole class, derivatives of the 2-substituted-3-aminoquinuclidine class, derivatives of the aminoazabicycloalkane class, derivatives of the 2-substituted-3-aminopiperidine class, derivatives of the 1-azabicyclo[3.2.2]nonan-3-amine class, derivatives of the N-alkylquinuclidinium salt class, derivatives of the pseudopeptide class, derivatives of the diacylpiperazine class, substituted aromatic derivatives, dialkylenepiperidino derivatives and substituted piperidine quaternary salts.

5. A combination according to claim 1, comprising at least one antagonist of NK2 receptors selected from the products of the arylalkylamine family, from the α-substituted polypeptide class and from the piperidine derivative class.

6. The synergistic combination according to claim 1, wherein said at least one product endowed with antagonist activity towards NK1 receptors is chosen from compounds of formulae (I) and (II) below, and salts thereof, wherein said compounds of formula (I) are chosen from perhydroisoindole compounds and salts thereof of formula (I):

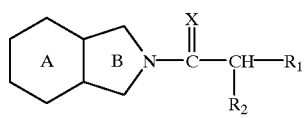

(I)

in which:

R₁ represents a phenyl radical which may be unsubstituted or substituted by at least one substitutent chosen from:

halogen atoms, hydroxyl radicals, alkyl radicals which can be unsubstituted or substituted by at least one group chosen from: halogen atoms, amino radicals, alkylamino radicals, and dialkylamino radicals; alkyloxy and alkylthio radicals which can be unsubstituted or substituted by a group chosen from: phenyl, hydroxyl and amino radicals; and dialkylamino radicals, alkylamino radicals, amino radicals, hydroxyl radicals, and dialkylamino radicals in which the alkyl parts form, with the nitrogen atom to which they are attached, 5- to 6-membered heterocycle rings which can contain an additional heteroatom chosen from oxygen, sulphur and nitrogen atoms, said heterocycle rings being unsubstituted or substituted by at least one group chosen from: alkyl radicals, hydroxyl radicals and hydroxyalkyl radicals;

alkyloxy radicals and alkylthiol radicals which can be unsubstituted or substituted by at least one group chosen from: amino radicals, alkylamino radicals, and dialkylamino radicals in which the alkyl parts can form, with the nitrogen atom to which they are attached, 5- to 6-membered heterocycle rings which can contain an additional heteroatom chosen from oxygen, sulphur, and nitrogen atoms, said heterocycle rings being unsubstituted or substituted by at least one group chosen from: alkyl radicals, hydroxyl radicals, and hydroxyalkyl radicals; or R₁ represents a cyclohexadienyl radical, a naphthyl radical, a saturated or unsaturated, mono- or polycyclic heterocyclyl radical having from 5 to 9 carbon atoms and at least one heteroatom chosen from oxygen, nitrogen and sulphur atoms, wherein said at least one heteroatom is unsubstituted or substituted by at least one group chosen from: halogen atoms, alkyl radicals, and alkyloxy radicals;

R₂ is chosen from a hydrogen atom, halogen atoms, a hydroxyl radical, alkyl radicals, aminoalkyl radicals, alkylaminoalkyl radicals, dialkylaminoalkyl radicals, alkyloxy radicals, alkylthio radicals, acyloxy radicals, carboxyl radicals, alkyloxycarbonyl radicals, dialkylaminoalkyloxycarbonyl radicals, benzyloxycarbonyl radicals, amino radicals and acylamino radicals;

the bicycle:

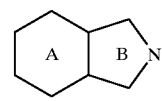

represents a perhydroisoindole or thiapyranopyrrole ring of formula:

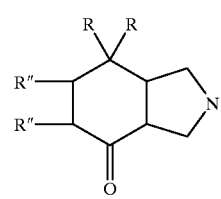

(Ia)

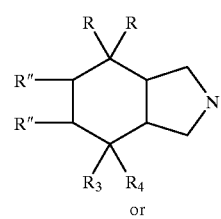

(Ib)

or

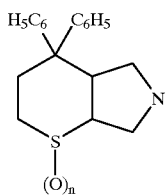

(Ic)

and X is chosen from: oxygen and sulphur atoms; $NR_6$ radicals in which $R_6$ is chosen from: a hydrogen atom; alkyl radicals containing from 1 to 12 carbon atoms which may be unsubstituted or substituted by at least one radical chosen from: carboxyl radicals, dialkylamino radicals, acylamino radicals, alkyloxycarbonyl radicals, alkyloxycarbonylamino radicals, carbamoyl radicals, alkylcarbamoyl radicals and dialkylcarbamoyl radicals, the alkyl portions of these substituents being unsubstituted or substituted by at least one radical chosen from dialkylamino radicals and phenyl radicals; a phenyl radical which may be unsubstituted or substituted by at least one group chosen from: halogen atoms, alkyl radicals, alkyloxy radicals and dialkylamino radicals; or $R_6$ is chosen from a naphthyl radical, a thienyl radical, a furyl radical, a pyridyl radical, an imidazolyl radical; and a dialkylamino radical;

wherein if the bicycle is of formula (Ib) or (Ic), X is chosen from an oxygen atom, and an NH radical; or the bicycle,

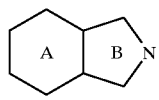

represents a perhydroisoindole or thiapyranopyrrole ring of formula:

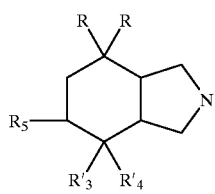

(Id)

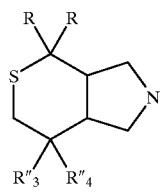

(Ie)

and X is an oxygen atom;

wherein in the formulae (Ia), (Ib), (Ic), (Id), and (Ie):
the R symbols are identical and represent phenyl radicals which can be unsubstituted or substituted by at least one halogen atom or by at least one methyl radical in the 2- or 3-position;
the R" symbols are identical and are hydrogen atoms or together form a bond;
$R_3$ is chosen from halogen atoms and a hydroxyl radical; and $R_4$ is a hydrogen atom or, simultaneously with $R_3$, $R_4$ is a halogen atom;

$R'_3$ is a phenyl radical which can be unsubstituted or substituted in the 2-position by at least one radical chosen from alkyl radicals and alkyloxy radicals having from 1 or 2 carbon atoms; $R'_4$ is chosen from a fluorine atom and a hydroxyl radical; and $R_5$ is a hydrogen atom; or $R'_4$ and $R_5$ are both hydroxyl radicals; or $R'_4$ forms a bond with $R_5$;

$R''_3$ is a hydrogen atom and $R''_4$ is chosen from a fluorine atom and a hydroxyl radical; or $R''_3$ is a phenyl radical which can be unsubstituted or substituted in the 2-position by at least one radical chosen from alkyl radicals and alkyloxy radicals having from 1 or 2 carbon atoms and $R''_4$ is a hydroxyl radical; or $R''_3$ and $R''_4$ together form an oxo radical; and n is an integer ranging from 0 to 2;

wherein said compounds of formulae (Ia), (Ib), (Ic), and (Id) may be in their respective stereoisomeric forms;

wherein said compounds of formula (Ie) may be in the (3aS,7R,7aR), (3aR,7S,7aS) or (3aRS,7SR,7aSR) form, if $R_4$ is a hydroxyl radical and $R_3$ is a phenyl radical; or may be in the (3aR,7S,7aS), (3aS,7R,7aR) or (3aRS,7SR,7aSR) form or mixtures thereof, if $R_3$ is a hydrogen atom and $R_4$ is a hydroxyl radical; or may be in the (3aR,7R,7aS), (3aS,7S,7aR) or (3aRS,7RS,7aSR) form or mixtures thereof, if $R_3$ is a hydrogen atom and $R_4$ is a fluorine atom; or may be in the (3aS,7aR), (3aR,7aS) or (3aRS,7aSR) form or mixtures thereof, if $R_3$ forms an oxo radical with $R_4$;

wherein said compounds of formula (II) are chosen from compounds of formula (II),

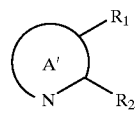

(II)

salts thereof, and stereoisometric forms thereof, in which the ring:

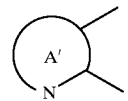

represents a monocyclic nitrogeneous hetercycle compound of formula (IIa):

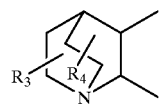

(IIa)

in which:
IIa (1)
($a_1$) $R_1$ is chosen from =N—$CH_2$—R radicals and —N=CH—R radicals, in which:
R is chosen from: cycloalkyl radicals having from 5 to 7 carbon atoms, a norbornyl radical, a pyrrolyl radical, a thienyl radical, a pyridyl radical, an indolyl radical, a biphenyl radical and a phenyl radical, which radicals can be unsubstituted or substituted by 1 or 2 substituents chosen from:
a fluorine atom, a chlorine atom, a bromine atom, a trifluoromethyl radical, an alkyl or an alkyloxy radical having from 1 to 3 carbon atoms, a carboxyl radical, an alkyloxycarbonyl radical in which the alkyl part contains from 1 to 3 carbon atoms, and a benzyloxycarbonyl radical;

$R_2$ is chosen from Ar—CHR'— radicals, in which:

R' is chosen from: branched alkyl radicals having 3 or 4 carbon atoms, branched alkylene radicals having 5 or 6 carbon atoms, cycloalkyl radicals having from 3 to 7 carbon atoms, a furyl radical, a thienyl radical, a pyridyl radical, an indolyl radical, a biphenyl radical, and a phenyl radical, which radicals can be unsubstituted or substituted by 1 or 2 substituents chosen from:
a fluorine atom, a chlorine atom, a bromine atom, a trifluoromethyl radical, an alkyl radical or an alkyloxy radical having from 1 to 3 carbon atoms, a carboxyl radical, an alkyloxycarbonyl radical in which the alkyl part contains from 1 to 3 carbon atoms, and a benzyloxycarbonyl radical; and Ar is a phenyl radical;

$R_3$ is a hydrogen atom; and $R_4$ is a hydrogen atom;

($a_{2.1}$) $R_1$ is chosen from —NH—CH$_2$—R radicals, in which:

R is chosen from: cycloalkyl radicals having from 5 to 7 carbon atoms, a norbornyl radical, a pyrrolyl radical, a thienyl radical, a pyridyl radical, an indolyl radical, a biphenyl radical and a phenyl radical, which radicals can be unsubstituted or substituted by 1 or 2 substituents chosen from:
a fluorine atom, a chlorine atom, a bromine atom, a trifluoromethyl radical, an alkyl radical or an alkyloxy radical having from 1 to 3 carbon atoms, a carboxyl radical, an alkyloxycarbonyl radical in which the alkyl part contains from 1 to 3 carbon atoms, and a benzyloxycarbonyl radical;

$R_2$ is chosen from Ar—CHR'— radicals, in which:

R' is chosen from: branched alkyl radicals having 3 or 4 carbon atoms, branched alkylene radicals having 5 or 6 carbon atoms, cycloalkyl radicals having from 3 to 7 carbon atoms, a furyl radical, a thienyl radical, a pyridyl radical, an indolyl radical, a biphenyl radical, and a phenyl radical, which radicals can be unsubstituted or substituted by 1 or 2 substituents chosen from:
a fluorine atom, a chlorine atom, a bromine atom, a trifluoromethyl radical, an alkyl radical or an alkyloxy radical having from 1 to 3 carbon atoms, a carboxyl radical, an alkyloxycarbonyl radical in which the alkyl part contains from 1 to 3 carbon atoms, and a benzyloxycarbonyl radical; and Ar is a phenyl radical;

$R_3$ is a hydrogen atom; and $R_4$ is a hydrogen atom;

($a_{2.2}$) $R_1$ is chosen from —NH—CH$_2$—R radicals, in which:

R is a phenyl radical disubstituted by a methoxy radical and a branched butyl radical;

$R_2$ is a benzhydryl radical;

$R_3$ is a hydrogen atom; and $R_4$ is a hydrogen atom;

($a_{2.3}$) $R_1$ is chosen from —NH—CH$_2$—R radicals, in which:

R is chosen from: a phenyl radical trisubstituted by radicals $X_1$, $X_2$ and $X_3$, in which: $X_1$ is chosen from a hydrogen atom, alkyl and alkyloxy radicals having from 1 to 10 carbon atoms which can be unsubstituted or substituted by from 1 to 3 fluorine atoms; and $X_2$ and $X_3$ are chosen from a hydrogen atom, halogen atoms, a NO$_2$ radical, alkyl and alkyloxy radicals having from 1 to 10 carbon atoms, which can be unsubstituted or substituted by from 1 to 3 substituents chosen from: a fluorine atom, an OH radical, a CN radical, a phenyl radical, an NH$_2$ radical, an alkylamino radical, a dialkylamino radical, an alkylcarbamoyl radical, an alkylcarbamoylalkyl radical and an acylamino radical in which the alkyl and acyl parts contain from 1 to 6 carbons; and an alkyloxyalkyl radical in which the alkyl parts contain from 1 to 4 carbon atoms;

$R_2$ is chosen from: Ar—CHR'— radicals, in which:

R' is chosen from: branched alkyl radicals having 3 or 4 carbon atoms, branched alkylene radicals having 5 or 6 carbon atoms, cycloalkyl radicals having from 3 to 7 carbon atoms, a furyl radical, a thienyl radical, a pyridyl radical, an indolyl radical, a biphenyl radical, and a phenyl radical, which radicals can be unsubstituted or substituted by 1 or 2 substituents chosen from:
a fluorine atom, a chlorine atom, a bromine atom, a trifluoromethyl radical, an alkyl radical or an alkyloxy radical having from 1 to 3 carbon atoms, a carboxyl radical, an alkyloxycarbonyl radical in which the alkyl part contains from 1 to 3 carbon atoms, and a benzyloxycarbonyl radical, or R' is chosen from alkyl and alkyloxy radicals having from 1 to 10 carbon atoms which can be unsubstituted or substituted by from 1 to 3 fluorine atoms; and Ar is chosen from: a phenyl radical, a biphenyl radical, a naphthyl radical, a pyridyl radical, a thienyl radical and a furyl radical which can be mono-, di- and trisubstituted by a group chosen from halogen atoms and alkyl and alkyloxy radicals having from 1 to 10 carbon atoms which can be unsubstituted or substituted by from 1 to 3 fluorine atoms;

$R_3$ is a hydrogen atom; and $R_4$ is a hydrogen atom;

($a_3$) $R_1$ is chosen from —NH—(C=Y)—R radicals, in which:

R is chosen from: benzopyran radicals that may contain an additional heteroatom chosen from O, S, N$^+$H, N$^+$alkyl and N$^+$aralkyl; and benzofuran radicals; wherein said benzopyran and benzofuran radicals may be unsubstituted or substituted in the position a to the oxygen by at least one methyl radical, and/or substituted by an oxo radical or thioxo radical and/or substituted on the phenyl ring of said benzopyran and benzofuran radicals by at least one group chosen from: halogen atoms, alkyl radicals, haloalkyl radicals, aralkyl radicals, alkyloxy radicals, aralkyloxy radicals, acyl radicals, acyloxy radicals, an OH radical, an NH$_2$ radical, a CN radical, an NO$_2$ radical, —NH—CO—R" radicals, S(O)$_n$—R" radicals, —NH—SO$_2$R" radicals, COOR" radicals, CONR"R'" radicals, OCONR"R'" radicals, CSNR"R'" radicals and SO$_2$NR"R'" radicals, in which R" and R'" are independently chosen from: a hydrogen atom, an alkyl radical, a phenyl radical and an aralkyl radical, n is 0, 1, or 2, and Y is chosen from O, S and 2H;

$R_2$ is chosen from —CHR$_5$R$_6$ radicals, in which:

$R_5$ is chosen from a thienyl radical and a phenyl radical, and $R_6$ is chosen from: an alkyl radical, an alkenyl radical, a cycloalkyl radical, a furyl radical, a thienyl radical, a pyridyl radical, an indolyl radical, a biphenyl radical and a phenyl radical;

$R_3$ is chosen from H and an alkyl radical; and $R_4$ is a hydrogen atom;
($b_2$) $R_1$ is chosen from —NH—CH$_2$—R radicals, in which:
R is chosen from: a phenyl radical trisubstituted by radicals $X_1$, $X_2$ and $X_3$, in which: $X_1$ is chosen from: a hydrogen atom, alkyl and alkyloxy radicals having from 1 to 10 carbon atoms which can be unsubstituted or substituted by from 1 to 3 fluorine atoms; and $X_2$ and $X_3$ are chosen from: a hydrogen atom, halogen atoms, a NO$_2$ radical, alkyl and alkyloxy radicals having from 1 to 10 carbon atoms, which can be unsubstituted or substituted by from 1 to 3 substituents chosen from: a fluorine atom, an OH radical, a CN radical, a phenyl radical, an NH$_2$ radical, an alkylamino radical, a dialkylamino radical, an alkylcarbamoyl radical, an alkylcarbamoylalkyl radical and an acylamino radical in which the alkyl and acyl parts contain from 1 to 6 carbons; and an alkyloxyalkyl radical in which the alkyl parts contain from 1 to 4 carbon atoms;
$R_2$ is chosen from: a phenyl radical, a biphenyl radical, a naphthyl radical, a pyridyl radical, a thienyl radical and a furyl radical, which radicals can be mono-, di- or tri-substituted by a group chosen from: halogen atoms and alkyl and alkyloxy radicals having from 1 to 10 carbon atoms which can be unsubstituted or substituted by from 1 to 3 fluorine atoms;
$R_3$ is an alkyl radical having from 1 to 6 carbon atoms; and
$R_4$ is a hydrogen atom;
(c) $R_1$ is chosen from —NH—CH$_2$—R radicals, in which:
R is chosen from: a phenyl radical, a thienyl radical, a pyridyl radical and a furyl radical, which radicals can be unsubstituted or substituted by from 1 to 3 substituents chosen from: a fluorine atom, a chlorine atom, a bromine atom, an iodine atom, a trifluoromethyl radical, alkyl radicals and alkyloxy radicals having from 1 to 4 carbon atoms;
$R_2$ is chosen from: a phenyl radical, a naphthyl radical, a thienyl radical, a pyridyl radical and a furyl radical, which radicals can be unsubstituted or substituted by from 1 to 3 substituents chosen from: a fluorine atom, a chlorine atom, a bromine atom, an iodine atom, a trifluoromethyl radical, alkyl radicals and alkyloxy radicals having from 1 to 4 carbon atoms;
$R_3$ is chosen from: a hydrogen atom and alkyl radicals having from 1 to 6 carbon atoms situated in the 5- or 6-position of said ring of formula (IIa); and
$R_4$ is a hydrogen atom;
(d) $R_1$ is chosen from —NH—CH$_2$—R radicals, in which:
R is chosen from: a phenyl radical, a naphthyl radical, a pyridyl radical, a quinolyl radical, a thienyl radical, a furyl radical, a phenoxyphenyl radical, an oxazolyl radical, a tetrazolyl radical, a thiazolyl radical, an imidazolyl radical and a pyrazolyl radical, which radicals can be unsubstituted or substituted by at least one substituent chosen from:
alkyl and alkyloxy radicals, which radicals may be unsubstituted or substituted from 1 to 3 halogen atoms, alkylthio radicals, alkylsulphinyl radicals, alkylsulphonyl radicals, alkylsulphonylamino radicals, and dialkylamino radicals, in which the alkyl parts can be unsubstituted or substituted by at least one substituent chosen from alkylsulphinyl radicals and alkylsulphonyl radicals in which the alkyl parts contain from 1 to 6 carbon atoms; sulphonamido radicals and alkenyl radicals having from 2 to 6 carbon atoms; or R is chosen from: phenyl radicals substituted by at least one substituent chosen from: halogen atoms, alkynyl radicals, alkylamino radicals, N-alkyl-N-(alkylsulphonyl)amino radicals and N-alkyl-N-alkanoylamino radicals, which radicals can be unsubstituted or substituted by a halogen atom on the alkylsulphonyl or alkanoyl part; alkylsulphonylamino radicals and alkanoylamino radicals, in which the alkyl parts can be unsubstituted or substituted by at least one halogen atom;
$R_2$ is chosen from Ar—CH(Ar')— radicals, in which:
Ar and Ar' are cyclic radicals chosen from: a phenyl radical, a naphthyl radical, a pyridyl radical, a quinolyl radical, a thienyl radical, a furyl radical, a phenoxyphenyl radical, an oxazolyl radical, a tetrazolyl radical, a thiazolyl radical, an imidazolyl radical and a pyrazolyl radical, which radicals can be unsubstituted or substituted by at least one substituent chosen from:
alkyl and alkyloxy radicals, which radicals may be unsubstituted or substituted from 1 to 3 halogen atoms, alkylthio radicals, alkylsulphinyl radicals, alkylsulphonyl radicals, alkylsulphonylamino radicals, and dialkylamino radicals, in which the alkyl parts can be unsubstituted or substituted by at least one substituent chosen from alkylsulphinyl radicals and alkylsulphonyl radicals in which the alkyl parts contain from 1 to 6 carbon atoms; sulphonamido radicals and alkenyl radicals having from 2 to 6 carbon atoms; or
said cyclic radicals are chosen from: phenyl radicals substituted by at least one substitutent chosen from: halogen atoms, alkynyl radicals, alkylamino radicals, N-alkyl-N-(alkylsulphonyl)amino radicals and N-alkyl-N-alkanoylamino radicals, which radicals can be unsubstituted or substituted by a halogen atom on the alkylsulphonyl or alkanoyl part; alkylsulphonylamino radicals and alkanoylamino radicals, in which the alkyl parts can be unsubstituted or substituted by at least one halogen atom;
wherein said cyclic radicals can be unsubstituted or substituted by at least one substituent chosen from:
alkyl radicals, alkyloxy radicals, alkylthio radicals, alkylsulphinyl radicals, and alkylamino radicals in which the alkyl parts contain from 1 to 4 carbon atoms, or by trifluoromethyl or trifluoromethoxy radicals;
$R_3$ is chosen from alkyl radicals having from 1 to 6 carbon atoms, alkenyl radicals having from 2 to 6 carbon atoms, and cycloalkyl radicals having from 3 to 8 carbon atoms, wherein said alkyl radicals, alkenyl radicals, and cycloalkyl radicals may be unsubstituted or substituted with an alkyloxy radical, a carbamoyl radical, a —CONR$_a$R$_b$ radical, a —COOH radical, a —COOR$_a$ radical, a —CHR$_a$OR$_b$ radical, a —CHR$_a$NR$_b$R$_c$ radical, a —COR$_a$ radical, a —CONR$_a$OR$_b$ radical, or an aryl radical;
$R_3$ is also chosen from alkyloxy radicals, a carbamoyl radical, —CONR$_a$R$_b$ radicals, a —COOH radical, —COOR$_a$ radicals, —CHR$_a$OR$_b$ radicals, —CHR$_a$NR$_b$R$_c$ radicals, —COR$_a$ radicals, —CONR$_a$OR$_b$ radicals, and aryl radicals; or
wherein R$_a$, R$_b$, and R$_c$, each independent of the other, are chosen from aryl radicals, cycloalkyl radicals, alkyloxy radicals, alkyl radicals, and a hydrogen atom;
$R_3$ is also chosen from Y—(CH$_2$)$_m$—CHR$_d$—(CH$_2$)$_n$—NR'$_d$—CO— radicals, in which:

$R_d$ is chosen from a hydrogen atom, alkyl radicals, a benzyl radical, and —(CH$_2$)$_p$—Y radicals;

$R'_d$ is chosen from a hydrogen atom; alkyl radicals which may be unsubstituted or substituted by an —OH radical, a —NH$_2$ radical, a —SCH$_3$ radical, or a —SH radical; a benzyl radical; —(CH$_2$)$_p$—Y radicals; a 4-hydroxybenzyl radical; and a 3-indolylmethyl radical;

Y is chosen from —CN, —CH$_2$Z, and —COZ, in which Z is chosen from an —OH radical, an —NH$_2$ radical, —Oalkyl radicals, —NHalkyl radicals, and —N(alkyl)$_2$ radicals; and m, n, and p, each independently of the other, have a value of 0, 1, 2 or 3;

wherein, in the definition of $R_3$, $R_a$, $R_b$, and $R_c$, said aryl radicals are chosen from a phenyl radical, a naphthyl radical, a pyridyl radical, a quinolyl radical, a thienyl radical, a furyl radical, a phenoxyphenyl radical, an oxazolyl radical, a tetrazolyl radical, a thiazolyl radical, an imidazoyl radical, and a pyrazolyl radical;

wherein, in the definition of $R_3$, $R_a$, $R_b$, and $R_c$, said aryl radicals may be unsubstituted or substituted by an alkyl radical which is unsubstituted or substituted with from 1 to 3 halogen atoms or an alkyloxy radical which is unsubstituted or substituted with from 1 to 3 halogen atoms;

wherein, in the definition of $R_3$, $R_a$, $R_b$, and $R_c$, said aryl radicals may be unsubstituted or substituted by an alkylthio radical, an alkylsulphinyl radical, an alkylsulphonyl radical, an alkylsulphonylamino radical, or a dialkylamino radical, wherein the alkyl part of said alkylthio, alkylsulphinyl, alkylsulphonyl, alkylsulphonylamino, or dialkylamino radicals may be unsubstituted or substituted by an alkylsulphinyl radical having from 1 to 6 carbon atoms, an alkylsulphonyl radical having from 1 to 6 carbon atoms, a sulphonamido radical having from 2 to 6 carbon atoms, or an alkenyl radical having from 2 to 6 carbon atoms;

wherein, in the definition of $R_3$, $R_a$, $R_b$, and $R_c$, when said aryl radical is a phenyl radical, said phenyl radical may be unsubstituted or substituted by a halogen atom, an alkynyl radical, an alkylamino radical, an N-alkyl-N-(alkylsulphonyl)amino radical, or an N-alkyl-N-alkanoylamino radial, wherein said alkynyl, alkylamino, N-alkyl-N-(alkylsulphonyl)amino, or N-alkyl-N-alkanoylamino radials may be unsubstituted or substituted with a halogen atom on the alkylsulphonyl part or alkanoyl part; an alkylsulphonylamino radical or an alkanoylamino radical, wherein said alkylsulphonylamino or alkanoylamino radicals may be unsubstituted or substituted by a halogen atom; and $R_4$ is a hydrogen atom; or (2) $R_1$ is chosen from —NH—CH$_2$—R radicals, in which:

R is chosen from: a phenyl radical trisubstituted by radicals $X_1$, $X_2$ and $X_3$, in which: $X_1$ is chosen from: a hydrogen atom, alkyl and alkyloxy radicals having from 1 to 10 carbon atoms which can be unsubstituted or substituted by from 1 to 3 fluorine atoms; and $X_2$ and $X_3$ are chosen from: a hydrogen atom, halogen atoms, a NO$_2$ radical, alkyl and alkyloxy radicals having from 1 to 10 carbon atoms, which can be unsubstituted or substituted by from 1 to 3 substituents chosen from: a fluorine atom, an OH radical, a CN radical, a phenyl radical, an NH$_2$ radical, alkylamino radicals, a dialkylamino radical, an alkylcarbamoyl radical, an alkylcarbamoylalkyl radical and an acylamino radical in which the alkyl and acyl parts contain from 1 to 6 carbons; and an alkyloxyalkyl radical in which the alkyl parts contain from 1 to 4 carbon atoms;

or R is chosen from: a cycloalkyl radical having from 5 to 7 carbon atoms, a pyrrolyl radical, a thienyl radical, a pyridyl or a phenyl radical which can be unsubstituted or substituted by from 1 to 3 substituents chosen from: a fluorine atom, a chlorine atom, a bromine atom, a trifluoromethyl radical, an alkyl or alkyloxy radical having from 1 to 3 carbon atoms, a carboxyl radical, an alkyloxycarbonyl radical, in which the alkyl part contains from 1 to 3 carbon atoms, and benzyloxycarbonyl radicals;

$R_2$ is chosen from —CHR'R" radicals, in which:

R' is chosen from: a furyl radical, a thienyl radical, a pyridyl radical, an indolyl radical, a biphenyl and a phenyl radical, which radicals can be unsubstituted or substituted by 1 or 2 substituents chosen from:
halogen atoms, alkyl and alkyloxy radicals having from 1 to 10 carbon atoms, which radicals can be unsubstituted or substituted by from 1 to 3 substituents chosen from: a fluorine atom, a carboxyl radical, an alkyloxycarbonyl radical where the alkyl part contains from 1 to 3 carbon atoms, and a benzyloxycarbonyl radical; and R" is chosen from: a thienyl radical, a phenyl radical, a halophenyl radical and a phenyl radical substituted by a substituent chosen from: alkyl and alkyloxy radicals having from 1 to 10 carbon atoms, which can be unsubstituted or substituted by from 1 to 3 fluorine atoms;

$R_3$, in the 5-position of said ring of formula (IIa), forms with $R_4$, an alkylene chain containing from 3 to 5 carbon atoms if $R_4$ is in the 6-position, or an alkylene chain containing from 2 to 3 carbon atoms if $R_4$ is in the 7-position, or an alkylene chain containing from 2 to 4 carbon atoms if $R_4$ is in the 8-position, or, when $R_3$ is in the 5-position and $R_4$ is in the 6-position, $R_3$ and $R_4$ can form a chain:

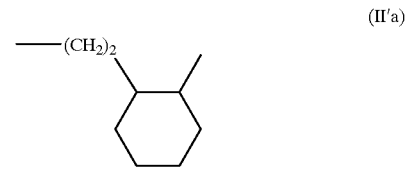

(II'a)

or, when $R_4$ is in the 8-position and $R_3$ is in the 5-position, $R_3$ and $R_4$ can form a chain —CH$_2$—X—CH$_2$—, in which X is chosen from: O, S, NH and >N(alkylamino) radicals, in which the alkyl part contains from 1 to 3 carbon atoms, or in which the ring:

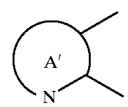

represent a monocyclic nitrogeneous hetercycle compound of formula (IIb):

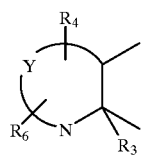
(IIb)

in which:

IIb (1) Y is chosen from $(CH_2)_n$ in which n ranges from 1 to 6 and can be a saturated or unsaturated chain, $R_1$ is chosen from —NR'—$CH_2$—R radicals, in which:

R is an aryl radical chosen from: a phenyl radical, a naphthyl radical, an indanyl radical, a thienyl radical, a pyridyl radical, a furyl radical, a thiazolyl radical, an isothiazolyl radical, an oxazolyl radical, an isoxazolyl radical, a triazolyl radical, a tetrazolyl radical and a quinolyl radical, which radicals can be unsubstituted or substituted by at least one substituent chosen from:

halo radicals, a nitro radical, an alkyl radical, an alkyloxy radical, a trifluoromethyl radical, an amino radical, a phenyl radical, alkylamino radicals, a formamido radical, an acylamido radical, an acylamidoalkyl radical, an alkylcarbamoyl radical and a cycloalkyl radical having from 3 to 7 carbon atoms, which substituents can be unsubstituted or substituted by 1 or 2 substituents as mentioned above and wherein one of the carbon atoms thereof can be replaced by a heteroatom chosen from N, O and S, and R' is chosen from a hydrogen atom and an alkyl radical; or $R_1$ is defined as in IIa (1)($a_{2-3}$);

$R_2$ is chosen from: a hydrogen atom, phenylalkyl radicals, benzhydryl radicals, straight or branched alkyl radicals, or aryl, and cycloalkyl radicals as defined above for R; or an aryl radical chosen from: a thiazolyl radical, an isothiazolyl radical, an oxazolyl radical, an isoxazolyl radical, a triazolyl radical and a tetrazolyl radical, which radicals can be unsubstituted or substituted by at least one substituent chosen from the substituents mentioned above for R; an dialkylamino, alkyloxycarbonyl, alkyloxycarbonyl, acyloxy, acrylalkyloxy, acyl or acylalkyl radicals;

$R_3$ is a hydrogen atom or when R, is defined as above in IIa (1)($a_{2-3}$), $R_3$ is a phenyl or alkyl radical containing from 1 to 6 carbon atoms, or $R_2$ and $R_3$, together with the carbon atoms to which they are attached, form 3- to 7-membered saturated carbocycles in which the carbon atoms can be replaced by a hetereoatom chosen from O, N, and S;

$R_5$ is —$(CHR'')_m$—R''' radical, in which m is an integer ranging from 0 to 6, in which the CHR'' units can form a double bond with an adjacent unit, and in which all the R'' radicals can be identical or different;

$R_4$ and $R_6$, independent of each other, are chosen from: a hydrogen atom, a hydroxyl radical, halo radicals, an amino radical, alkylamino radicals, dialkylamino radicals, alkyloxy radicals, alkyloxycarbonyl radicals, alkyloxycarbonylalkyl radicals, acyloxy radicals, acylalkyloxy radicals, acyl and acylalkyl radicals, phenylalkyl radicals, benzhydryl radicals, straight or branched alkyl radicals, or aryl and cycloalkyl radicals as defined above for R' with the proviso that $R_4$ and $R_6$ are incapable of forming a ring with $R_5$;

or, if $R_1$ is as defined in IIa (1)($a_{2-3}$), $R_4$ and $R_6$ can also be oxo, hydroxyakyl, or alkyloxyalkyl; and R'' and R''' are defined as being chosen from the same substituents as defined for $R_4$ and $R_6$, or, if $R_1$ is a radical as defined in IIa (1)($a_{2-3}$), R'' can also be =N—OH and R''' can also be a radical —NHCOR$_d$, —NHCH$_2$R$_d$, SO$_2$R$_d$ or NHSO$_2$R$_d$, and R$_d$ is hydrogen, alkyl, phenylalkyl or phenyl substituted by alkyl having from 1 to 6 carbon atoms; or (2)

—Y—N($R_5$)— is a residue of an azabicyclic compound chosen from quinuclidinyls, azabicycloheptyls and azabicyclooctyls; in which:

$R_5$ is chosen from a hydrogen atom, a benzyl radical, and (($CH_2)_m R_e$)—$R_f$ radicals wherein m is 0 to 6, in which:

$R_e$ and $R_f$ are, independent of each other, chosen from:

a phenyl radical, a naphthyl radical, a pyridyl radical, a quinolyl radical, a thienyl radical, a furyl radical, a phenoxyphenyl radical, an oxazolyl radical, a tetrazolyl radical, a thiazolyl radical, an imidazolyl radical and a pyrazolyl radical which can be unsubstituted or substituted by at least one substituent chosen from:

alkyl radicals and alkyloxy radicals, optionally carrying from 1 to 3 halogen atoms; alkylthio radicals, alkylsulphinyl radicals, alkylsulphonyl radicals, alkylsulphonylamino radicals, dialkylamino radicals, in which the alkyl parts can be unsubstituted or substituted by at least one substituent chosen from alkylsulphinyl radicals and alkylsulphonyl radicals in which the alkyl parts contain from 1 to 6 carbon atoms; sulphonamido radicals and alkenyl radicals having from 2 to 6 carbon atoms;

with the exception of representing aminoalkyl or alkylcarbomoyl, or representing alkyl or phenylalkyl or benzhydryl, which can be substituted or unsubstituted on the phenyl ring by one or more substitutents chosen from halogen, alkyl or alkyloxy having optionally 1 to 3 fluorine atoms; and (a) $R_1$ is chosen from —X—$CH_2$—R radicals, in which:

X is chosen from: an oxygen atom and a sulphur atom; and

R is chosen from phenyl radicals which can be unsubstituted or substituted by from 1 to 3 identical or different radicals chosen from:

alkyl radicals, alkenyl and alkynyl radicals having from 2 to 6 carbon atoms; halogen atoms, a cyano radical, a nitro radical, a trifluoromethyl radical, a trimethylsilyl radical, —OR' radicals, a —SCH$_3$ radical, a —SOCH$_3$ radical, a —SO$_2$CH$_3$ radical, —NR'R'' radicals, —NR'COR'' radicals, —NR'CO$_2$R'' radicals, —CO$_2$R' radicals and —CONR'R'' radicals in which R' and R'', which are identical or different, are chosen from: a hydrogen atom, alkyl radicals, a phenyl radical and trifluoromethyl radical;

$R_2$ is chosen from —$CR_aR_bR_c$ radicals, in which:

$R_a$ and $R_b$, which are identical or different, are chosen from a phenyl radical and thienyl radical which can be unsubstituted or substituted by at least one substituent chosen from: a halo radical, a trifluoromethyl radical, and cycloalkyl radicals;

$R_a$ is further chosen from a phenyl radical and a thienyl radical substituted by at least one alkyloxy radical;

$R_b$ is further chosen from a benzyl radical, which can be unsubstituted or substituted by at least one substituent chosen from: a halo radical, a trifluoromethyl radical and a cycloalkyl radical, and $R_c$ is a hydrogen or hydroxyl; and $R_3$, $R_4$ and $R_6$ are each a hydrogen atom;

(b) $R_1$ is chosen from —$CH_2$—CHX—Ar radicals and =CH—CHX—Ar radicals, in which:

Ar is chosen from a phenyl radical which can be unsubstituted or substituted by from 1 to 3 identical or different radicals chosen from:

alkyl radicals, alkenyl and alkynyl radicals having from 2 to 6 carbon atoms, halogen atoms, a cyano radical, a nitro radical, a trifluoromethyl radical, a trimethylsilyl radical, —OR' radicals, a —$SCH_3$ radical, a —$SOCH_3$ radical, a —$SO_2CH_3$ radical, —NR'R" radicals, —NR'COR" radicals, —NR'CO$_2$R" radicals, —CO$_2$R' radicals and —CONR'R" radicals in which R' and R", which are identical or different, are chosen from: a hydrogen atom, alkyl radicals, a phenyl radical, halo radicals, cyloalkyl radicals and a trifluoromethyl radical;

X is chosen from a hydrogen atom, an OH radical, an =O radical and halogen atoms;

$R_2$ is chosen from —$CR_aR_b$ radicals, in which:

$R_a$ and $R_b$, which are identical or different, are chosen from: a phenyl radical, a thienyl radical and a benzyl radical which can be unsubstituted or substituted by at least one halo or trifluromethyl radical;

$R_3$, $R_4$ and $R_6$ are each a hydrogen atom; or (c) $R_1$ is chosen from —NR"—$CH_2$—R radicals, in which: R is defined as in (IIb)(1), wherein R" is hydrogen or alkyl or $R_1$ represents alkyloxycarbonyl, fomyl, hydroxymethyl, phenoxy methyl or alkyloxymethyl;

$R_2$ is as defined in (IIb)(1);

$R_3$, $R_4$, and $R_6$ are chosen from a hydrogen atom, alkyl radicals and a phenyl radical; or (d) —Y—, substituted by $R_4$ and $R_6$ radicals, is a —$CHR_a$—$CR_b(CR_cR_d)$— chain, wherein at least one $R_a$ is chosen from a hydrogen atom, a hydroxymethyl radical, an alkyl radical, an acyloxyalkyl radical, an alkyloxymethyl radical and a benzyloxymethyl radical;

$R_b$ and $R_c$, independent of each other, are chosen from a hydrogen atom, an alkyl radical and a phenyl radical; and $R_d$ is chosen from a methyl radical and a hydroxymethyl radical; and $R_1$ and $R_2$ and $R_3$ are defined as just above in (IIb)(2)(c); or (3) Y is chosen from —$(CH_2)_n$— radicals in which n is equal to 1 to 3;

$R_1$ is chosen from —X—$CH_2$—R radicals, in which:

X is chosen from: an oxygen atom and a sulphur atom; and

R is chosen from phenyl radicals which can be unsubstituted or substituted by from 1 to 3 identical or different radicals chosen from:

alkyl radicals, alkenyl and alkynyl radicals having from 2 to 6 carbon atoms; halogen atoms, a cyano radical, a nitro radical, a trifluoromethyl radical, a trimethylsilyl radical, —OR' radicals, a —$SCH_3$ radical, a —$SOCH_3$ radical, a —$SO_2CH_3$ radical, —NR'R" radicals, —NR'COR" radicals, —NR'CO$_2$R" radicals, —CO$_2$R' radicals, —CONR'R" radicals, SR' radicals, SOR' radicals and SO$_2$R' radicals, in which R' and R", which are identical or different, are chosen from: a hydrogen atom, alkyl radicals, a phenyl radical, and trifluoromethyl radical;

$R_2$ is chosen from a phenyl radical, a naphthyl radical, an indazolyl radical, a thienyl radical, a furyl radical, a pyridyl radical, a thiazolyl radical, a tetrazolyl radical and a quinolyl radical which can be unsubstituted or substituted by at least one substituent chosen from:

alkyl radicals, alkyloxy radicals, halogen atoms, a trifluoromethyl radical, benzhydryl and benzyl radicals, which can be unsubstituted or substituted by at least one group chosen from: alkyl radicals and alkyloxy radicals containing from 1 to 6 carbon atoms, halogen atoms and a $CF_3$ radical;

$R_3$ is H;

$R_4$ and $R_6$, independent of each other, are chosen from halogen atoms, —$CH_2OR°$ radicals, alkyl radicals, an oxo radical, COOR° radicals and CONR°R° radicals in which R° is chosen from a hydrogen atom, a $CF_3$ radical, an alkyl radical and a phenyl radical; and $R_5$ is chosen from a hydrogen atom and an alkyl radical, which alkyl radical can be unsubstituted or substituted by at least one substituent chosen from: aromatic heterocycles which may be unsubstituted or substituted, COOR°° radicals, CONR°°R°° radicals, an OH radical, a CN radical, COR° radicals, —NR°°R°° radicals, C(NOH)NR°°R°° radicals, CONHphenylalkyl radicals, COCOOR°° radicals, COCONR°°R°° radicals, phenyl radicals, which can be unsubstituted or substituted by at least one substituent chosen from alkyl radicals, alkyloxy radicals, halogen atoms and a $CF_3$ radical;

R° is chosen from a hydrogen atom, a $CF_3$ radical, an alkyl radical and a phenyl radical; and wherein R°° is chosen from a hydrogen atom and alkyl radicals;

wherein, unless explicitly mentioned otherwise, said alkyl radicals and alkyl parts contain from 1 to 6 carbon atoms.

7. The synergistic combination according to claim 1, wherein said at least one product endowed with antagonist activity towards NK1 receptors is chosen from perhydroisoindole compounds and salts thereof of formula (I):

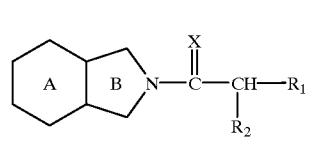

in which:

$R_1$ represents a phenyl radical which may be unsubstituted or substituted by at least one substitutent chosen from:

halogen atoms, hydroxyl radicals, alkyl radicals which can be unsubstituted or substituted by at least one group chosen from: halogen atoms, amino radicals, alkylamino radicals, and dialkylamino radicals; alkyloxy and alkylthio radicals which can be unsubstituted or substituted by a group chosen from: phenyl, hydroxyl and amino radicals; and dialkylamino radicals, alkylamino radicals, amino radicals, hydroxyl radicals, and dialkylamino radicals in which the alkyl parts form, with the nitrogen atom to which they are attached, 5- to 6-membered heterocycle rings which can contain an additional heteroatom chosen from oxygen, sulphur and nitrogen atoms, said heterocycle rings being unsubstituted or substituted by at least one group chosen from: alkyl radicals, hydroxyl radicals and hydroxyalkyl radicals;

alkyloxy radicals and alkylthiol radicals which can be unsubstituted or substituted by at least one group chosen from: amino radicals, alkylamino radicals, and dialkylamino radicals in which the alkyl parts can form, with the nitrogen atom to which they are attached, 5- to 6-membered heterocycle rings which can contain an additional heteroatom chosen from oxygen, sulphur, and nitrogen atoms, said heterocycle rings being unsubstituted or substituted by at least one group chosen from: alkyl radicals, hydroxyl radicals, and hydroxyalkyl radicals; or $R_1$ represents a cyclohexadienyl radical, a naphthyl radical, a saturated or unsaturated, mono- or polycyclic heterocyclyl radical having from 5 to 9 carbon atoms and at least one heteroatom chosen from oxygen, nitrogen and sulphur atoms, wherein said at least one heteroatom is unsubstituted or substituted by at least one group chosen from: halogen atoms, alkyl radicals, and alkyloxy radicals;

$R_2$ is chosen from a hydrogen atom, halogen atoms, a hydroxyl radical, alkyl radicals, aminoalkyl radicals, alkylaminoalkyl radicals, dialkylaminoalkyl radicals, alkyloxy radicals, alkylthio radicals, acyloxy radicals, carboxyl radicals, alkyloxycarbonyl radicals, dialkylaminoalkyloxycarbonyl radicals, benzyloxycarbonyl radicals, amino radicals and acylamino radicals;

the bicycle:

represents a perhydroisoindole or thiapyranopyrrole ring of formula:

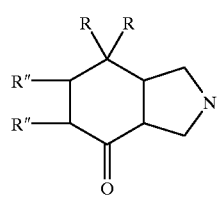
(Ia)

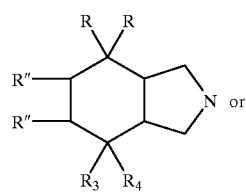
(Ia)

or

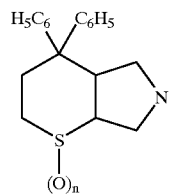
(Ic)

and X is chosen from: oxygen and sulphur atoms; $NR_6$ radicals in which $R_6$ is chosen from: a hydrogen atom; alkyl radicals containing from 1 to 12 carbon atoms which may be unsubstituted or substituted by at least one radical chosen from: carboxyl radicals, dialkylamino radicals, acylamino radicals, alkyloxycarbonyl radicals, alkyloxycarbonylamino radicals, carbamoyl radicals, alkylcarbamoyl radicals and dialkylcarbamoyl radicals, the alkyl portions of these substituents being unsubstituted or substituted by at least one radical chosen from dialkylamino radicals and phenyl radicals; a phenyl radical which may be unsubstituted or substituted by at least one group chosen from: halogen atoms, alkyl radicals, alkyloxy radicals and dialkylamino radicals; or $R_6$ is chosen from a naphthyl radical, a thienyl radical, a furyl radical, a pyridyl radical, an imidazolyl radical; and a dialkylamino radical;

wherein if the bicycle is of formula (Ib) or (Ic), X is chosen from an oxygen atom, and an NH radical; or the bicycle,

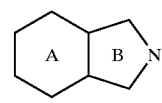

represents a perhydroisoindole or thiapyranopyrrole ring of formula:

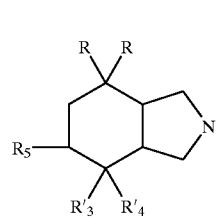
(Id)

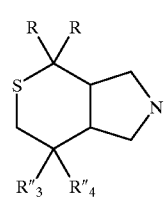
(Ie)

and X is an oxygen atom;
wherein in the formulae (Ia), (Ib), (Ic), (Id), and (Ie):
the R symbols are identical and represent phenyl radicals which can be unsubstituted or substituted by at least one halogen atom or by at least one methyl radical in the 2- or 3-position;
the R" symbols are identical and are hydrogen atoms or together form a bond;
$R_3$ is chosen from halogen atoms and a hydroxyl radical; and $R_4$ is a hydrogen atom or, simultaneously with $R_3$, $R_4$ is a halogen atom;

R'₃ is a phenyl radical which can be unsubstituted or substituted in the 2-position by at least one radical chosen from alkyl radicals and alkyloxy radicals having from 1 or 2 carbon atoms; R'₄ is chosen from a fluorine atom and a hydroxyl radical; and R₅ is a hydrogen atom; or R'₄ and R₅ are both hydroxyl radicals; or R'₄ forms a bond with R₅;

R"₃ is a hydrogen atom and R"₄ is chosen from a fluorine atom and a hydroxyl radical; or R"₃ is a phenyl radical which can be unsubstituted or substituted in the 2-position by at least one radical chosen from alkyl radicals and alkyloxy radicals having from 1 or 2 carbon atoms and R"₄ is a hydroxyl radical; or R"₃ and R"₄ together form an oxo radical; and n is an integer ranging from 0 to 2; wherein said compounds of formulae (Ia), (Ib), (Ic), and (Id) may be in their respective stereoisomeric forms; wherein said compounds of formula (Ie) may be in the (3aS,7R,7aR), (3aR,7S,7aS) or (3aRS,7SR,7aSR) form, if R₄ is a hydroxyl radical and R₃ is a phenyl radical; or may be in the (3aR,7S,7aS), (3aS,7R,7aR) or (3aRS,7SR,7aSR) form or mixtures thereof, if R₃ is a hydrogen atom and R₄ is a hydroxyl radical; or may be in the (3aR,7R,7aS), (3aS,7S,7aR) or (3aRS,7RS,7aSR) form or mixtures thereof, if R₃ is a hydrogen atom and R₄ is a fluorine atom; or may be in the (3aS,7aR), (3aR,7aS) or (3aRS,7aSR) form or mixtures thereof, if R₃ forms an oxo radical with R₄;

wherein said at least one product endowed with antagonist activity towards NK2 receptors is chosen from compounds and salts thereof having the following formula (VIII):

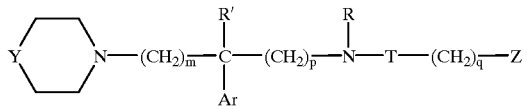

(VIII)

in which:

VIII(1) Y is chosen from >N—CXX'—Ar', >CH—CXX'—Ar' and >C=CX—Ar', in which:

X is H, and X' is H or OH, or X and X' together form an oxo radical or a dialkylaminoalkyloxyimino radical in which the alkyl parts contain from 1 to 4 carbon atoms and the alkyloxy part contains 2 or 3 carbon atoms;

Ar and Ar', independent of each other, are chosen from a thienyl radical and a phenyl radical, which can be unsubstituted or substituted by at least one substituent chosen from: halogen atoms, alkyl and alkyloxy radicals having from 1 to 3 carbon atoms, a trifluoromethyl radical, a hydroxyl radical, and a methylenedioxy radical; and an imidazolyl radical; or Ar is chosen from: a benzothienyl radical and a naphthyl radical, which can be unsubstituted or substituted by at least one substituent chosen from: halogens, a biphenyl radical and a indolyl radical, which can be unsubstituted or substituted with a benzyl group on the nitrogen atom;

R' is chosen from a hydrogen atom, alkyl radicals having from 1 to 4 carbon atoms, and alkyl radicals having 2 or 3 carbon atoms and being substituted by at least one substituent chosen from: a piperidino radical, a 4-benzylpiperidino radical, and a dialkylamino radical in which the alkyl parts contain from 1 to 4 carbon atoms;

R is chosen from a hydrogen atom, alkyl radicals having from 1 to 6 carbon atoms, and aminoalkyl radicals of structure —(CH₂)ₙ—NH₂, in which n is equal to 2 to 6;

T is a group chosen from —CO—, —CO—O—, —CO—NH— and —CS—NH—; and

Z is chosen from a hydrogen atom, straight or branched alkyl radicals having from 1 to 6 carbon atoms, phenylalkyl radicals in which the alkyl part contains from 1 to 3 carbon atoms, which can be unsubstituted or substituted on the phenyl by at least one substituent chosen from halogens, an OH radical, alkyl radicals and alkyloxy radicals having from 1 to 4 carbon atoms; pyridylalkyl radicals, naphthylalkyl radicals, pyridylthioalkyl radicals, 1-methyl-2-imidazolylthioalkyl radicals in which the alkyl part contains from 1 to 3 carbon atoms; a styryl radical, a 1-oxo-3-phenyl-2-indanyl radical and an unsubstituted, mono- or polysubstituted heteroaromatic or aromatic group; and m is an integer from 1 to 3, p is equal to 1, and q is equal to 0; or (2) Y is a group chosen from >N—Ar', in which:

Ar' is chosen from a phenyl radical which can be unsubstituted or substituted by at least one by substituent chosen from: halogen atoms, an OH radical, alkyloxy and alkyl radicals having from 1 to 4 carbon atoms and a trifluoromethyl radical; a pyrimidinyl radical, a pyridyl radical, and a >N-cycloalkyl group having from 3 to 7 carbon atoms;

or Y is group >CX—(CH₂)ₓ—Ar', in which:

Ar' is chosen from a phenyl radical which can be unsubstituted or substituted by at least one by substituent chosen from: halogen atoms, an OH radical, alkyloxy and alkyl radicals having from 1 to 4 carbon atoms and a trifluoromethyl radical; a thienyl radical, a pyridyl radical, and a >N-cycloalkyl group having from 3 to 7 carbon atoms;

X is chosen from an OH radical, alkyloxy radicals having from 1 to 4 carbon atoms, hydroxyalkyl radicals and acyloxy radicals in which the alkyl part contains from 1 to 3 carbon atoms, a phenacyloxy radical, a carboxyl radical, carbalkoxy radicals having from 1 to 4 carbon atoms, a cyano radical, aminoalkylene radicals having from 1 to 3 carbon atoms, an amino radical, alkylamino radicals and dialkylamino radicals in which the alkyl parts contain from 1 to 4 carbon atoms, acylamino radicals having from 2 to 7 carbon atoms, acylaminoalkyl radicals in which the alkyl parts contain from 1 to 3 carbon atoms, an acyl radical, a —SH radical, alkylthio radicals in which the alkyl part contains from 1 to 4 carbon atoms; and x is 0 or 1; or Y is =C—(CH₂)ₓ—Ar', in which x is 0 or 1 and Ar' is defined as above in VIII (1);

Z is chosen from a hydrogen atom, straight or branched alkyl radicals having from 1 to 6 carbon atoms, phenylalkyl radicals in which the alkyl part contains from 1 to 3 carbon atoms, which can be unsubstituted or substituted on the phenyl by at least one substituent chosen from halogens, an OH radical, alkyl radicals and alkyloxy radicals having from 1 to 4 carbon atoms; pyridylalkyl radicals, naphthylalkyl radicals, pyridylthioalkyl radicals, a styryl radical, an unsubstituted, mono- or polysubstituted heteroaromatic or aromatic group; phenylalkyl radicals substituted by trifluoromethyl or naphthylalkyl in which the alkyl part contains from 1 to 3 carbon atoms and which can be unsubstituted or substituted on the naphthyl ring by at least one substituenet chosen from halogen atoms, a trifluoromethyl radical, an OH radical, alkyl radicals and alkyloxy radicals having from 1 to 4 carbon atoms, Ar is chosen from: a thienyl radical and a phenyl radical, which can be mono- or polysubstituted by at least one substitutent chosen from halogen atoms, alkyl radicals and alkyloxy radicals having from 1 to 4 carbon atoms, and a trifluoromethyl radicals; a benzothienyl radical, a naphthyl radical and an indolyl radicals, which can carry alkyl groups having from 1 to 3 carbon atoms on the nitrogen atom;

R' is a hydrogen atom;

R is chosen from a hydrogen atom and alkyl radicals having from 1 to 6 carbon atoms, T is chosen from a —CO— group, a —CO—O— group, a —CO—NH— group and a —CS—NH— group; and m is an integer equal to 2 or 3; p is equal to 1; and q is equal to 0; or (3) Y is chosen from: >N—Ar' groups, >N—CH$_2$—Ar' groups, and >CX—(CH$_2$)$_x$—Ar' groups, in which:

Ar is defined as above in VIII(2);

X is chosen from OH radical, alkyloxy radicals, acyloxy radicals and carbalkoxy radicals having from 1 to 4 carbon atoms; carboxyl radicals, cyano radicals; amino radicals, pyrrolidino radicals, piperidino radicals, and morpholino radicals, which can be unsubstituted, mono- or disubstituted by at least one substituent chosen from alkyl radicals, hydroxyalkyl radicals and acyl radicals having from 1 to 4 carbon atoms; an —SH radical or alkylthio radical in which the alkyl part contains from 1 to 4 carbon atoms;

x is 0 or 1; or

Y is a =C—(CH$_2$)$_x$—Ar' group in which x is 0 or 1 and Ar' is defined as above in VIII(2) with the exception that Ar' cannot represent a substituted indolyl radical;

R and R' together form

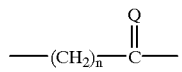

chains, in which:

Q is an oxygen atom or 2 hydrogen atoms, n is equal to 0 to 3;

T is —CO— or —CH$_2$—; and

Z is chosen from a phenyl radical and a naphthyl radical unsubstituted or substituted by at least one substituent chosen from: halogen atoms, a trifluoromethyl radical, an OH radical, alkyl radicals having from 1 to 4 carbon atoms, and alkyloxy radicals having from 1 to 4 carbon atoms;

wherein when Z is chosen from a phenyl radical, a pyridyl radical, a thienyl radical, an indolyl radical, a quinolyl radical, a benzothienyl radical and an imidazolyl radical, or an unsubstituted, mono- or polysubstituted heteroaromatic or aromatic group, or, when T is CO, —(CH$_2$)$_q$—Z can be a benzyl radical in which the methyl radical is substituted by at least one substituent chosen from: an OH radical, alkyl radicals and alkyloxy radicals having from 1 to 4 carbon atoms, or substituted on the ring by at least one substituent chosen from: halogen atoms, a trifluoromethyl radical, an OH radical, alkyl radicals and alkyloxy radicals having from 1 to 4 carbon atoms; and m is an integer equal to 2 or 3; p is equal to 1 or 2; and q is equal to 0 to 3;

wherein, if p=2, then n=1 and Q represents 2H;

(4) Y is an Ar'—X— group, in which:

Ar' is chosen from a thienyl radical and a phenyl radical, which can be unsubstituted or substituted by at least one substituent chosen from halogen atoms, alkyl and alkyloxy radicals having from 1 to 3 carbon atoms, a trifluoromethyl radical, a hydroxyl radical and a methylenedioxy radical; a pyridyl radical and an imidazolyl radical, which can be unsubstituted or substituted by at least one radical chosen from alkyl radicals;

X is chosen from an oxygen atom, a sulphur atom, a sulphonyl group, a sulphinyl group, an —NH— group, >N—CO-Alk groups, >N-Alk groups and >N-Alk-NX$_1$X$_2$ groups in which:

Alk is chosen from alkyl radicals and alkylene radicals having from 1 to 3 carbon atoms; and X$_1$ and X$_2$ are chosen from a hydrogen atom and alkyl radicals having from 1 to 3 carbon atoms; or form, with the nitrogen atom, a piperidine ring, a pyrrolidine ring or a morpholine ring;

R' is chosen from a hydrogen atom, alkyl radicals having from 1 to 4 carbon atoms, aminoalkyl radicals in which the straight-chain alkyl part contains 2 or 3 carbon atoms and the amino group can be a dialkylamino radical in which the alkyl parts contain from 1 to 4 carbon atoms, piperidino or 4-benzylpiperidino;

Ar, R, and T are defined above as in VIII(1);

Z is as defined in VIII(1) or represents an α-hydroxybenzyl radical or an α-alkylbenzyl radical in which the alkyl part contains from 1 to 3 carbon atoms; and m is an integer equal to 2 or 3; p is equal to 1; and q is equal to 0; or (5) Y is chosen from >CX—(CH$_2$)$_x$—Ar' groups, in which:

Ar' is chosen from a thienyl radical and a phenyl radical, which can be substituted by at least one substituent chosen from: halogen atoms, alkyl and alkyloxy radicals having from 1 to 4 carbon atoms, a trifluoromethyl radical and a hydroxyl radical; or a pyridyl radical;

x is 0 or 1;

X is chosen from —NH—CO-alkyl radicals in which the alkyl part contains from 1 to 6 carbon atoms;

m is 2 or 3; p is 1; and q is equal to 0;

Ar, T and Z are as defined in VIII(2); and

R' is H, and

R is H or alkyl.

8. The synergistic combination according to claim 7, wherein said at least one product endowed with antagonist activity towards NK1 receptors is a perhydroisoindol compound or a salt thereof, which contains a ring corresponding to formula (Ia) or (Id) or a salt thereof.

9. The synergistic combination according to claim 8, wherein said at least one product endowed with antagonist activity towards NK1 receptors is a perhydroisoindol compound or a salt thereof which contains a ring corresponding to formula (Id), and which compound is (3aS,4S,7aS)-7,7-diphenyl-4-(2-methoxyphenyl)-2-[(S)-2-(2-methoxyphenyl)propionyl]perhydroisoindol-4-ol.

10. The synergistic combination according to claim 8, wherein said at least one product endowed with antagonist activity towards NK1 receptors is a perhydroisoindol compound or a salt thereof which contains a ring corresponding to formula (Ia), and which compound is (3aR,7aR)-2-[1-imino-2-(2-methoxypheny)ethyl]-7,7-diphenylperhydroisoindol-4-one.

11. The synergistic combination according to claim 7, wherein said at least one product endowed with antagonist activity toward NK2 receptors is an arylalkylamine compound or a salt thereof having formula (VIII), and which compound is N-methyl-[4-(4-phenyk-4-acetamidopiperidinyl)-2-(3,4-dichlorophenyl)-butyl]benzamide.

12. The synergistic combination according to claim 1, wherein said at least one product endowed with antagonist activity towards NK1 receptors is chosen from compounds having formula (I) below, compounds having formula (IIa) below, compounds having formula (IIb) below and salts of each of said compounds,
wherein said compounds of formula (I) are chosen from perhydroisoindole compounds and salts thereof of formula (I):

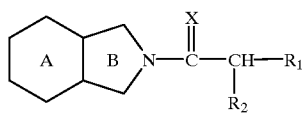
(I)

in which:
R₁ represents a phenyl radical which may be unsubstituted or substituted by at least one substitutent chosen from:
halogen atoms, hydroxyl radicals, alkyl radicals which can be unsubstituted or substituted by at least one group chosen from: halogen atoms, amino radicals, alkylamino radicals, and dialkylamino radicals; alkyloxy and alkylthio radicals which can be unsubstituted or substituted by a group chosen from: phenyl, hydroxyl and amino radicals; and dialkylamino radicals, alkylamino radicals, amino radicals, hydroxyl radicals, and dialkylamino radicals in which the alkyl parts form, with the nitrogen atom to which they are attached, 5- to 6-membered heterocycle rings which can contain an additional heteroatom chosen from oxygen, sulphur and nitrogen atoms, said heterocycle rings being unsubstituted or substituted by at least one group chosen from: alkyl radicals, hydroxyl radicals and hydroxyalkyl radicals;
alkyloxy radicals and alkylthiol radicals which can be unsubstituted or substituted by at least one group chosen from: amino radicals, alkylamino radicals, and dialkylamino radicals in which the alkyl parts can form, with the nitrogen atom to which they are attached, 5- to 6-membered heterocycle rings which can contain an additional heteroatom chosen from oxygen, sulphur, and nitrogen atoms, said heterocycle rings being unsubstituted or substituted by at least one group chosen from: alkyl radicals, hydroxyl radicals, and hydroxyalkyl radicals; or
R₁ represents a cyclohexadienyl radical, a naphthyl radical, a saturated or unsaturated, mono- or polycyclic heterocyclyl radical having from 5 to 9 carbon atoms and at least one heteroatom chosen from oxygen, nitrogen and sulphur atoms, wherein said at least one heteroatom is unsubstituted or substituted by at least one group chosen from: halogen atoms, alkyl radicals, and alkyloxy radicals;
R₂ is chosen from a hydrogen atom, halogen atoms, a hydroxyl radical, alkyl radicals, aminoalkyl radicals, alkylaminoalkyl radicals, dialkylaminoalkyl radicals, alkyloxy radicals, alkylthio radicals, acyloxy radicals, carboxyl radicals, alkyloxycarbonyl radicals, dialkylaminoalkyloxycarbonyl radicals, benzyloxycarbonyl radicals, amino radicals and acylamino radicals;

the bicycle:

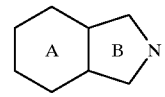

represents a perhydroisoindole or thiapyranopyrrole ring of formula:

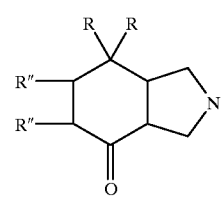
(Ia)

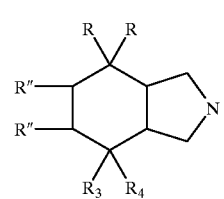
(Ib)

and X is chosen from: oxygen and sulphur atoms; NR₆ radicals in which R₆ is chosen from: a hydrogen atom; alkyl radicals containing from 1 to 12 carbon atoms which may be unsubstituted or substituted by at least one radical chosen from: carboxyl radicals, dialkylamino radicals, acylamino radicals, alkyloxycarbonyl radicals, alkyloxycarbonylamino radicals, carbamoyl radicals, alkylcarbamoyl radicals and dialkylcarbamoyl radicals, the alkyl portions of these substituents being unsubstituted or substituted by at least one radical chosen from dialkylamino radicals and phenyl radicals; a phenyl radical which may be unsubstituted or substituted by at least one group chosen from: halogen atoms, alkyl radicals, alkyloxy radicals and dialkylamino radicals; or R₆ is chosen from a naphthyl radical, a thienyl radical, a furyl radical, a pyridyl radical, an imidazolyl radical; and a dialkylamino radical;

wherein if the bicycle is of formula (Ib), X is chosen from an oxygen atom, and an NH radical; or the bicycle,

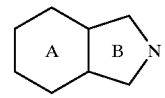

represents a perhydroisoindole or thiapyranopyrrole ring of formula:

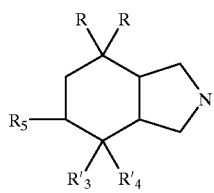

(Id)

and X is an oxygen atom;
wherein in the formulae (Ia), (Ib), and (Id):
the R symbols are identical and represent phenyl radicals which can be unsubstituted or substituted by at least one halogen atom or by at least one methyl radical in the 2- or 3-position;
the R" symbols are identical and are hydrogen atoms or together form a bond;
$R_3$ is chosen from halogen atoms and a hydroxyl radical; and $R_4$ is a hydrogen atom or, simultaneously with $R_3$, $R_4$ is a halogen atom;
$R'_3$ is a phenyl radical which can be unsubstituted or substituted in the 2-position by at least one radical chosen from alkyl radicals and alkyloxy radicals having from 1 or 2 carbon atoms; $R'_4$ is chosen from a fluorine atom and a hydroxyl radical; and $R_5$ is a hydrogen atom; or $R'_4$ and $R_5$ are both hydroxyl radicals; or $R'_4$ forms a bond with $R_5$;
$R''_3$ is a hydrogen atom and $R''_4$ is chosen from a fluorine atom and a hydroxyl radical; or $R''_3$ is a phenyl radical which can be unsubstituted or substituted in the 2-position by at least one radical chosen from alkyl radicals and alkyloxy radicals having from 1 or 2 carbon atoms and $R''_4$ is a hydroxyl radical; or $R''_3$ and $R''_4$ together form an oxo radical; and
wherein said compounds of formulae (Ia), (Ib), and (Id) may be in their respective stereoisomeric forms;
and salts thereof;
wherein said at least one product endowed with antagonist activity towards NK2 receptors is chosen from compounds and salts thereof having the following formula (VIII):

(VIII)

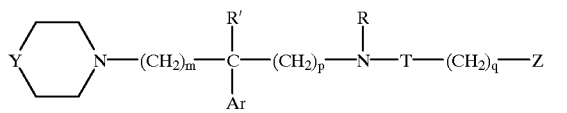

in which:
VIII(1) Y is chosen from >N—CXX'—Ar', >CH—CXX'—Ar' and >C=CX—Ar', in which:
X is H, and X' is H or OH, or X and X' together form an oxo radical or a dialkylaminoalkyloxyimino radical in which the alkyl parts contain from 1 to 4 carbon atoms and the alkyloxy part contains 2 or 3 carbon atoms;
Ar and Ar', independent of each other, are chosen from a thienyl radical and a phenyl radical, which can be unsubstituted or substituted by at least one substituent chosen from: halogen atoms, alkyl and alkyloxy radicals having from 1 to 3 carbon atoms, a trifluoromethyl radical, a hydroxyl radical, and a methylenedioxy radical; and an imidazolyl radical; or Ar is chosen from: a benzothienyl radical and a naphthyl radical, which can be unsubstituted or substituted by at least one substituent chosen from: halogens, a biphenyl radical and a indolyl radical, which can be unsubstituted or substituted with a benzyl group on the nitrogen atom;
R' is chosen from a hydrogen atom, alkyl radicals having from 1 to 4 carbon atoms, and alkyl radicals having 2 or 3 carbon atoms and being substituted by at least one substituent chosen from: a piperidino radical, a 4-benzylpiperidino radical, and a dialkylamino radical in which the alkyl parts contain from 1 to 4 carbon atoms;
R' is chosen from a hydrogen atom, alkyl radicals having from 1 to 6 carbon atoms, and aminoalkyl radicals of structure —$(CH_2)_n$—$NH_2$, in which n is equal to 2 to 6;
T is a group chosen from —CO—, —CO—O—, —CO—NH— and —CS—NH—; and
Z is chosen from a hydrogen atom, straight or branched alkyl radicals having from 1 to 6 carbon atoms, phenylalkyl radicals in which the alkyl part contains from 1 to 3 carbon atoms, which can be unsubstituted or substituted on the phenyl by at least one substituent chosen from halogens, an OH radical, alkyl radicals and alkyloxy radicals having from 1 to 4 carbon atoms; pyridylalkyl radicals, naphthylalkyl radicals, pyridylthioalkyl radicals, 1-methyl-2-imidazolylthioalkyl radicals in which the alkyl part contains from 1 to 3 carbon atoms; a styryl radical, a 1-oxo-3-phenyl-2-indanyl radical and an unsubstituted, mono- or polysubstituted heteroaromatic or aromatic group; and
m is an integer from 1 to 3, p is equal to 1, and q is equal to 0; or
(2) Y is a group chosen from >N—Ar', in which:
Ar' is chosen from a phenyl radical which can be unsubstituted or substituted by at least one by substituent chosen from: halogen atoms, an OH radical, alkyloxy and alkyl radicals having from 1 to 4 carbon atoms and a trifluoromethyl radical; a pyrimidinyl radical, a pyridyl radical, and a >N-cycloalkyl group having from 3 to 7 carbon atoms;
or Y is group >CX—$(CH_2)_x$—Ar', in which:
Ar' is chosen from a phenyl radical which can be unsubstituted or substituted by at least one by substituent chosen from: halogen atoms, an OH radical, alkyloxy and alkyl radicals having from 1 to 4 carbon atoms and a trifluoromethyl radical a thienyl radical, a pyridyl radical, and a >N-cycloalkyl group having from 3 to 7 carbon atoms;
X is chosen from an OH radical, alkyloxy radicals having from 1 to 4 carbon atoms, hydroxyalkyl radicals and acyloxy radicals in which the alkyl part contains from 1 to 3 carbon atoms, a phenacyloxy radical, a carboxyl radical, carbalkoxy radicals having from 1 to 4 carbon atoms, a cyano radical, aminoalkylene radicals having from 1 to 3 carbon atoms, an amino radical, alkylamino radicals and dialkylamino radicals in which the alkyl parts contain from 1 to 4 carbon atoms, acylamino radicals having from 2 to 7 carbon atoms, acylaminoalkyl radicals in which the alkyl parts contain from 1 to 3 carbon atoms, an acyl radical, a -SH radical, alkylthio radicals in which the alkyl part contains from 1 to 4 carbon atoms; and x is 0 or 1; or
Y is =C—$(CH_2)_x$—Ar', in which x is 0 or 1 and Ar' is defined as above in VIII (1);

Z is chosen from a hydrogen atom, straight or branched alkyl radicals having from 1 to 6 carbon atoms, phenylalkyl radicals in which the alkyl part contains from 1 to 3 carbon atoms, which can be unsubstituted or substituted on the phenyl by at least one substituent chosen from halogens, an OH radical, alkyl radicals and alkyloxy radicals having from 1 to 4 carbon atoms; pyridylalkyl radicals, naphthylalkyl radicals, pyridylthioalkyl radicals, a styryl radical, an unsubstituted, mono- or polysubstituted heteroaromatic or aromatic group; phenylalkyl radicals substituted by trifluoromethyl or naphthylalkyl in which the alkyl part contains from 1 to 3 carbon atoms and which can be unsubstituted or substituted on the naphthyl ring by at least one substituenet chosen from halogen atoms, a trifluoromethyl radical, an OH radical, alkyl radicals and alkyloxy radicals having from 1 to 4 carbon atoms, Ar is chosen from: a thienyl radical and a phenyl radical, which can be mono- or polysubstituted by at least one substitutent chosen from halogen atoms, alkyl radicals and alkyloxy radicals having from 1 to 4 carbon atoms, and a trifluoromethyl radicals; a benzothienyl radical, a naphthyl radical and an indolyl radicals, which can carry alkyl groups having from 1 to 3 carbon atoms on the nitrogen atom;

R' is a hydrogen atom;

R is chosen from a hydrogen atom and alkyl radicals having from 1 to 6 carbon atoms, T is chosen from a —CO— group, a —CO—O— group, a —CO—NH— group and a —CS—NH— group; and m is an integer equal to 2 or 3; p is equal to 1; and q is equal to 0; or (3) Y is chosen from: >N—A' groups, >N—CH$_2$—Ar' groups, and >CX—(CH$_2$)$_x$—Ar— groups, in which:

Ar is defined as above in VIII(2);

X is chosen from OH radical, alkyloxy radicals, acyloxy radicals and carbalkoxy radicals having from 1 to 4 carbon atoms; carboxyl radicals, cyano radicals; amino radicals, pyrrolidino radicals, piperidino radicals, and morpholino radicals, which can be unsubstituted, mono- or disubstituted by at least one substituent chosen from alkyl radicals, hydroxyalkyl radicals and acyl radicals having from 1 to 4 carbon atoms; an —SH radical or alkylthio radical in which the alkyl part contains from 1 to 4 carbon atoms;

x is 0 or 1; or

Y is a =C—(CH$_2$)$_x$Ar' group in which x is 0 or 1 and Ar' is defined as above in VIII(2) with the exception that Ar' cannot represent a substituted indolyl radical;

R and R' together form

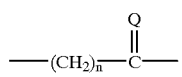

chains, in which:

Q is an oxygen atom or 2 hydrogen atoms, n is equal to 0 to 3;

T is —CO— or —CH$_2$—; and

Z is chosen from a phenyl radical and a naphthyl radical unsubstituted or substituted by at least one substituent chosen from: halogen atoms, a trifluoromethyl radical, an OH radical, alkyl radicals having from 1 to 4 carbon atoms, and alkyloxy radicals having from 1 to 4 carbon atoms;

wherein when Z is chosen from a phenyl radical, a pyridyl radical, a thienyl radical, an indolyl radical, a quinolyl radical, a benzothienyl radical and an imidazolyl radical, or an unsubstituted, mono- or polysubstituted heteroaromatic or aromatic group, or, when T is CO, —(CH$_2$)$_q$—Z can be a benzyl radical in which the methyl radical is substituted by at least one substituent chosen from: an OH radical, alkyl radicals and alkyloxy radicals having from 1 to 4 carbon atoms, or substituted on the ring by at least one substituent chosen from: halogen atoms, a trifluoromethyl radical, an OH radical, alkyl radicals and alkyloxy radicals having from 1 to 4 carbon atoms; and m is an integer equal to 2 or 3; p is equal to 1 or 2; and q is equal to 0 to 3;

wherein, if p=2, then n=1 and Q represents 2H;

(4) Y is an Ar'—X— group, in which:

Ar' is chosen from a thienyl radical and a phenyl radical, which can be unsubstituted or substituted by at least one substituent chosen from halogen atoms, alkyl and alkyloxy radicals having from 1 to 3 carbon atoms, a trifluoromethyl radical, a hydroxyl radical and a methylenedioxy radical; a pyridyl radical and an imidazolyl radical, which can be unsubstituted or substituted by at least one radical chosen from alkyl radicals;

X is chosen from an oxygen atom, a sulphur atom, a sulphonyl group, a sulphinyl group, an —NH— group, >N—CO-Alk groups, >N-Alk groups and >N-Alk-NX$_1$X$_2$ groups in which:

Alk is chosen from alkyl radicals and alkylene radicals having from 1 to 3 carbon atoms; and X$_1$ and X$_2$ are chosen from a hydrogen atom and alkyl radicals having from 1 to 3 carbon atoms; or form, with the nitrogen atom, a piperidine ring, a pyrrolidine ring or a morpholine ring;

R' is chosen from a hydrogen atom, alkyl radicals having from 1 to 4 carbon atoms, aminoalkyl radicals in which the straight-chain alkyl part contains 2 or 3 carbon atoms and the amino group can be a dialkylamino radical in which the alkyl parts contain from 1 to 4 carbon atoms, piperidino or 4-benzylpiperidino;

Ar, R, and T are defined above as in VIII(1);

Z is as defined in VIII(1) or represents an α-hydroxybenzyl radical or an α-alkylbenzyl radical in which the alkyl part contains from 1 to 3 carbon atoms; and m is an integer equal to 2 or 3; p is equal to 1; and q is equal to 0; or (5) Y is chosen from >CX—(CH$_2$)$_x$—Ar' groups, in which:

Ar' is chosen from a thienyl radical and a phenyl radical, which can be substituted by at least one substituent chosen from: halogen atoms, alkyl and alkyloxy radicals having from 1 to 4 carbon atoms, a trifluoromethyl radical and a hydroxyl radical; or a pyridyl radical;

x is 0 or 1;

X is chosen from —NH—CO-alkyl radicals in which the alkyl part contains from 1 to 6 carbon atoms;

m is 2 or 3; p is 1; and q is equal to 0;

Ar, T and Z are as defined in VIII(2); and

R' is H, and

R is H or alkyl; and salts thereof.

13. The synergistic combination according to claim 1, wherein said at least one product endowed with antagonist activity towards NK1 receptors is chosen from compounds and salts thereof having the formula (IIb):
in which the ring:

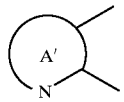

represent a monocyclic nitrogeneous hetercycle compound of formula (IIb):

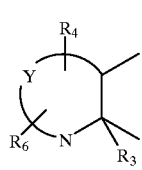

(IIb)

in which:

IIb (1) Y is chosen from $(CH_2)n$ in which n ranges from 1 to 6 and can be a saturated or unsaturated chain, $R_1$ is chosen from $—NR'—CH_2—R$ radicals, in which:
R is an aryl radical chosen from: a phenyl radical, a naphthyl radical, an indanyl radical, a thienyl radical, a pyridyl radical, a furyl radical, a thiazolyl radical, an isothiazolyl radical, an oxazolyl radical, an isoxazolyl radical, a triazolyl radical, a tetrazolyl radical and a quinolyl radical, which radicals can be unsubstituted or substituted by at least one substituent chosen from:
halo radicals, a nitro radical, an alkyl radical, an alkyloxy radical, a trifluoromethyl radical, an amino radical, a phenyl radical, alkylamino radicals, a formamido radical, an acylamido radical, an acylamidoalkyl radical, an alkylcarbamoyl radical and a cycloalkyl radical having from 3 to 7 carbon atoms, which substituents can be unsubstituted or substituted by 1 or 2 substituents as mentioned above and wherein one of the carbon atoms thereof can be replaced by a heteroatom chosen from N, O and S, and
R' is chosen from a hydrogen atom and an alkyl radical;
or $R_1$ is defined as in IIa (1)($a_{2-3}$);

$R_2$ is chosen from: a hydrogen atom, phenylalkyl radicals, benzhydryl radicals, straight or branched alkyl radicals, or aryl, and cycloalkyl radicals as defined above for R; or an aryl radical chosen from: a thiazolyl radical, an isothiazolyl radical, an oxazolyl radical, an isoxazolyl radical, a triazolyl radical and a tetrazolyl radical, which radicals can be unsubstituted or substituted by at least one substituent chosen from the substituents mentioned above for R; an dialkylamino, alkyloxycarbonyl, alkyloxycarbonyl, acyloxy, acrylalkyloxy, acyl or acylalkyl radicals;

$R_3$ is a hydrogen atom or when R, is defined as above in IIa (1)($a_{2-3}$), $R_3$ is a phenyl or alkyl radical containing from 1 to 6 carbon atoms, or $R_2$ and $R_3$ together with the carbon atoms to which they are attached, form 3- to 7-membered saturated carbocycles in which the carbon atoms can be replaced by a hetereoatom chosen from O, N, and S;

$R_5$ is $—(CHR")_m—R'''$ radical, in which m is an integer ranging from 0 to 6, in which the CHR" units can form a double bond with an adjacent unit, and in which all the R" radicals can be identical or different;

$R_4$ and $R_6$, independent of each other, are chosen from: a hydrogen atom, a hydroxyl radical, halo radicals, an amino radical, alkylamino radicals, dialkylamino radicals, alkyloxy radicals, alkyloxycarbonyl radicals, alkyloxycarbonylalkyl radicals, acyloxy radicals, acylalkyloxy radicals, acyl and acylalkyl radicals, phenylalkyl radicals, benzhydryl radicals, straight or branched alkyl radicals, or aryl and cycloalkyl radicals as defined above for R' with the proviso that $R_4$ and $R_6$ are incapable of forming a ring with $R_5$;

or, if $R_1$ is as defined in IIa (1)($a_{2-3}$), $R_4$ and $R_6$ can also be oxo, hydroxyakyl, or alkyloxyalkyl; and R" and R'" are defined as being chosen from the same substituents as defined for $R_4$ and $R_6$, or, if $R_1$ is a radical as defined in IIa (1)($a_{2-3}$), R" can also be $=N—OH$ and R'" can also be a radical $—NHCOR_d$, $—NHCH_2Rd$, $SO_2R_d$ or $NHSO_2R_d$, and $R_d$ is hydrogen, alkyl, phenylalkyl or phenyl substituted by alkyl having from 1 to 6 carbon atoms; or (2)
$—Y—N(R_5)—$ is a residue of an azabicyclic compound chosen from quinuclidinyls, azabicycloheptyls and azabicyclooctyls; in which:

$R_5$ is chosen from a hydrogen atom, a benzyl radical, and $((CH_2)_mR_e)—R_f$ radicals wherein m is 0 to 6, in which:
$R_e$ and $R_f$ are, independent of each other, chosen from:
a phenyl radical, a naphthyl radical, a pyridyl radical, a quinolyl radical, a thienyl radical, a furyl radical, a phenoxyphenyl radical, an oxazolyl radical, a tetrazolyl radical, a thiazolyl radical, an imidazolyl radical and a pyrazolyl radical which can be unsubstituted or substituted by at least one substituent chosen from:
alkyl radicals and alkyloxy radicals, optionally carrying from 1 to 3 halogen atoms; alkylthio radicals, alkylsulphinyl radicals, alkylsulphonyl radicals, alkylsulphonylamino radicals, dialkylamino radicals, in which the alkyl parts can be unsubstituted or substituted by at least one substituent chosen from alkylsulphinyl radicals and alkylsulphonyl radicals in which the alkyl parts contain from 1 to 6 carbon atoms; sulphonamido radicals and alkenyl radicals having from 2 to 6 carbon atoms;
with the exception of representing aminoalkyl or alkylcarbomoyl, or representing alkyl or phenylalkyl or benzhydryl, which can be substituted or unsubstituted on the phenyl ring by one or more substitutents chosen from halogen, alkyl or alkyloxy having optionally 1 to 3 fluorine atoms; and (a) $R_1$ is chosen from $—X—CH_2—R$ radicals, in which:
X is chosen from: an oxygen atom and a sulphur atom; and
R is chosen from phenyl radicals which can be unsubstituted or substituted by from 1 to 3 identical or different radicals chosen from:
alkyl radicals, alkenyl and alkynyl radicals having from 2 to 6 carbon atoms; halogen atoms, a cyano radical, a nitro radical, a trifluoromethyl radical, a trimethylsilyl radical, $—OR'$ radicals, a $—SCH_3$ radical, a $—SOCH_3$ radical, a $—SO_2CH_3$ radical, $—NR'R"$ radicals, $—NR'COR"$ radicals, $—NR'CO_2R"$ radicals, $—CO_2R'$ radicals and $—CONR'R"$ radicals in which R' and R", which are identical or different, are chosen from: a hydrogen atom, alkyl radicals, a phenyl radical and trifluoromethyl radical;

$R_2$ is chosen from —$CR_aR_bR_c$ radicals, in which:

$R_a$ and $R_b$, which are identical or different, are chosen from a phenyl radical and thienyl radical which can be unsubstituted or substituted by at least one substituent chosen from: a halo radical, a trifluoromethyl radical, and cycloalkyl radicals;

$R_a$ is further chosen from a phenyl radical and a thienyl radical substituted by at least one alkyloxy radical;

$R_b$ is further chosen from a benzyl radical, which can be unsubstituted or substituted by at least one substituent chosen from: a halo radical, a trifluoromethyl radical and a cycloalkyl radical, and $R_c$ is a hydrogen or hydroxyl; and $R_3$, $R_4$ and $R_6$ are each a hydrogen atom;

(b) $R_1$ is chosen from —$CH_2$—CHX—Ar radicals and =CH—CHX—Ar radicals, in which:

Ar is chosen from a phenyl radical which can be unsubstituted or substituted by from 1 to 3 identical or different radicals chosen from:

alkyl radicals, alkenyl and alkynyl radicals having from 2 to 6 carbon atoms, halogen atoms, a cyano radical, a nitro radical, a trifluoromethyl radical, a trimethylsilyl radical, —OR' radicals, a —$SCH_3$ radical, a —$SOCH_3$ radical, a —$SO_2CH_3$ radical, —NR'R" radicals, —NR'COR" radicals, —NR'CO$_2$R" radicals, —CO$_2$R' radicals and —CONR'R" radicals in which R' and R", which are identical or different, are chosen from: a hydrogen atom, alkyl radicals, a phenyl radical, halo radicals, cyloalkyl radicals and a trifluoromethyl radical;

X is chosen from a hydrogen atom, an OH radical, an =O radical and halogen atoms;

$R_2$ is chosen from —$CR_aR_b$ radicals, in which:

$R_a$ and $R_b$, which are identical or different, are chosen from: a phenyl radical, a thienyl radical and a benzyl radical which can be unsubstituted or substituted by at least one halo or trifluromethyl radical;

$R_3$, $R_4$ and $R_6$ are each a hydrogen atom; or (c) $R_1$ is chosen from —NR"—$CH_2$—R radicals, in which: R is defined as in (IIb)(1), wherein R" is hydrogen or alkyl or $R_1$ represents alkyloxycarbonyl, formyl, hydroxymethyl, phenoxy methyl or alkyloxymethyl;

$R_2$ is as defined in (IIb)(1);

$R_3$, $R_4$, and $R_6$ are chosen from a hydrogen atom, alkyl radicals and a phenyl radical; or (d) —Y—, substituted by $R_4$ and $R_6$ radicals, is a —CHR$_a$—CR$_b$(CR$_c$R$_d$)— chain, wherein at least one $R_a$ is chosen from a hydrogen atom, a hydroxymethyl radical, an alkyl radical, an acyloxyalkyl radical, an alkyloxymethyl radical and a benzyloxymethyl radical;

$R_b$ and $R_c$, independent of each other, are chosen from a hydrogen atom, an alkyl radical and a phenyl radical; and $R_d$ is chosen from a methyl radical and a hydroxymethyl radical; and $R_1$ and $R_2$ and $R_3$ are defined as just above in (IIb)(2)(c); or (3) Y is chosen from —$(CH_2)_n$— radicals in which n is equal to 1 to 3;

$R_1$ is chosen from —X—$CH_2$—R radicals, in which:

X is chosen from: an oxygen atom and a sulphur atom; and

R is chosen from phenyl radicals which can be unsubstituted or substituted by from 1 to 3 identical or different radicals chosen from:

alkyl radicals, alkenyl and alkynyl radicals having from 2 to 6 carbon atoms; halogen atoms, a cyano radical, a nitro radical, a trifluoromethyl radical, a trimethylsilyl radical, —OR' radicals, a —$SCH_3$ radical, a —$SOCH_3$ radical, a —$SO_2CH_3$ radical, —NR'R" radicals, —NR'COR" radicals, —NR'CO$_2$R" radicals, —CO$_2$R' radicals, —CONR'R" radicals, SR' radicals, SOR' radicals and $SO_2$R' radicals, in which R' and R", which are identical or different, are chosen from: a hydrogen atom, alkyl radicals, a phenyl radical, and trifluoromethyl radical;

$R_2$ is chosen from a phenyl radical, a naphthyl radical, an indazolyl radical, a thienyl radical, a furyl radical, a pyridyl radical, a thiazolyl radical, a tetrazolyl radical and a quinolyl radical which can be unsubstituted or substituted by at least one substituent chosen from:

alkyl radicals, alkyloxy radicals, halogen atoms, a trifluoromethyl radical, benzhydryl and benzyl radicals, which can be unsubstituted or substituted by at least one group chosen from: alkyl radicals and alkyloxy radicals containing from 1 to 6 carbon atoms, halogen atoms and a $CF_3$ radical;

$R_3$ is H;

$R_4$ and $R_6$, independent of each other, are chosen from halogen atoms, —$CH_2OR°$ radicals, alkyl radicals, an oxo radical, COOR° radicals and CONR°R° radicals in which R° is chosen from a hydrogen atom, a $CF_3$ radical, an alkyl radical and a phenyl radical; and $R_5$ is chosen from a hydrogen atom and an alkyl radical, which alkyl radical can be unsubstituted or substituted by at least one substituent chosen from: aromatic heterocycles which may be unsubstituted or substituted, COOR°° radicals, CONR°°R°° radicals, an OH radical, a CN radical, COR° radicals, —NR°°R°° radicals, C(NOH)NR°°R°° radicals, CONHphenylalkyl radicals, COCOOR°° radicals, COCONR°°R°° radicals, phenyl radicals, which can be unsubstituted or substituted by at least one substituent chosen from alkyl radicals, alkyloxy radicals, halogen atoms R° is chosen from a hydrogen atom, a $CF_3$ radical, an alkyl radical and a phenyl radical; and wherein R°° is chosen from a hydrogen atom and alkyl radicals;

wherein, unless explicitly mentioned otherwise, said alkyl radicals and alkyl parts contain from 1 to 6 carbon atoms;

wherein said at least one product endowed with antagonist activity towards NK2 receptors is chosen from compounds and salts thereof having the following formula (VIII):

(VIII)

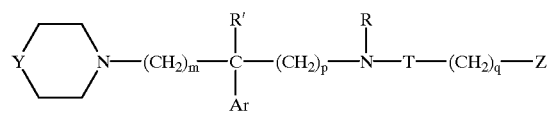

in which:

VIII(1) Y is chosen from >N—CXX'—Ar', >CH—CXX'—Ar' and >C=CX—Ar', in which:

X is H, and X' is H or OH, or X and X' together form an oxo radical or a dialkylaminoalkyloxyimino radical in which the alkyl parts contain from 1 to 4 carbon atoms and the alkyloxy part contains 2 or 3 carbon atoms, Ar and Ar', independent of each other, are chosen from a thienyl radical and a phenyl radical, which can be unsubstituted or substituted by at least one substituent chosen from: halogen atoms, alkyl and alkyloxy radicals having from 1 to 3 carbon atoms, a trifluoromethyl radical, a hydroxyl radical, and a methylenedioxy radical; and an imidazolyl radical; or Ar is chosen from: a benzothienyl radical and a naphthyl radical, which can be unsubstituted or substituted by at least one substituent chosen from: halogens, a biphenyl radical and a indolyl radical, which can be unsubstituted or substituted with a benzyl group on the nitrogen atom;

R' is chosen from a hydrogen atom, alkyl radicals having from 1 to 4 carbon atoms, and alkyl radicals having 2 or 3 carbon atoms and being substituted by at least one substituent chosen from: a piperidino radical, a 4-benzylpiperidino radical, and a dialkylamino radical in which the alkyl parts contain from 1 to 4 carbon atoms;

R is chosen from a hydrogen atom, alkyl radicals having from 1 to 6 carbon atoms, and aminoalkyl radicals of structure $—(CH_2)_n—NH_2$, in which n is equal to 2 to 6;

T is a group chosen from —CO—, —CO—O—, —CO—NH— and —CS—NH—; and

Z is chosen from a hydrogen atom, straight or branched alkyl radicals having from 1 to 6 carbon atoms, phenylalkyl radicals in which the alkyl part contains from 1 to 3 carbon atoms, which can be unsubstituted or substituted on the phenyl by at least one substituent chosen from halogens, an OH radical, alkyl radicals and alkyloxy radicals having from 1 to 4 carbon atoms; pyridylalkyl radicals, naphthylalkyl radicals, pyridylthioalkyl radicals, 1-methyl-2-imidazolylthioalkyl radicals in which the alkyl part contains from 1 to 3 carbon atoms; a styryl radical, a 1-oxo-3-phenyl-2-indanyl radical and an unsubstituted, mono- or polysubstituted heteroaromatic or aromatic group; and m is an integer from 1 to 3, p is equal to 1, and q is equal to 0; or (2) Y is a group chosen from >N—Ar', in which:

Ar' is chosen from a phenyl radical which can be unsubstituted or substituted by at least one by substituent chosen from: halogen atoms, an OH radical, alkyloxy and alkyl radicals having from 1 to 4 carbon atoms and a trifluoromethyl radical; a pyrimidinyl radical, a pyridyl radical, and a >N-cycloalkyl group having from 3 to 7 carbon atoms;

or Y is group $>CX—(CH_2)_x—Ar'$, in which:

Ar' is chosen from a phenyl radical which can be unsubstituted or substituted by at least one by substituent chosen from: halogen atoms, an OH radical, alkyloxy and alkyl radicals having from 1 to 4 carbon atoms and a trifluoromethyl radical a thienyl radical, a pyridyl radical, and a >N-cycloalkyl group having from 3 to 7 carbon atoms;

X is chosen from an OH radical, alkyloxy radicals having from 1 to 4 carbon atoms, hydroxyalkyl radicals and acyloxy radicals in which the alkyl part contains from 1 to 3 carbon atoms, a phenacyloxy radical, a carboxyl radical, carbalkoxy radicals having from 1 to 4 carbon atoms, a cyano radical, aminoalkylene radicals having from 1 to 3 carbon atoms, an amino radical, alkylamino radicals and dialkylamino radicals in which the alkyl parts contain from 1 to 4 carbon atoms, acylamino radicals having from 2 to 7 carbon atoms, acylaminoalkyl radicals in which the alkyl parts contain from 1 to 3 carbon atoms, an acyl radical, a —SH radical, alkylthio radicals in which the alkyl part contains from 1 to 4 carbon atoms; and x is 0 or 1; or Y is $=C—(CH_2)_x—Ar'$, in which x is 0 or 1 and Ar' is defined as above in VIII (1);

Z is chosen from a hydrogen atom, straight or branched alkyl radicals having from 1 to 6 carbon atoms, phenylalkyl radicals in which the alkyl part contains from 1 to 3 carbon atoms, which can be unsubstituted or substituted on the phenyl by at least one substituent chosen from halogens, an OH radical, alkyl radicals and alkyloxy radicals having from 1 to 4 carbon atoms; pyridylalkyl radicals, naphthylalkyl radicals, pyridylthioalkyl radicals, a styryl radical, an unsubstituted, mono- or polysubstituted heteroaromatic or aromatic group; phenylalkyl radicals substituted by trifluoromethyl or naphthylalkyl in which the alkyl part contains from 1 to 3 carbon atoms and which can be unsubstituted or substituted on the naphthyl ring by at least one substituenet chosen from halogen atoms, a trifluoromethyl radical, an OH radical, alkyl radicals and alkyloxy radicals having from 1 to 4 carbon atoms, Ar is chosen from: a thienyl radical and a phenyl radical, which can be mono- or polysubstituted by at least one substitutent chosen from halogen atoms, alkyl radicals and alkyloxy radicals having from 1 to 4 carbon atoms, and a trifluoromethyl radicals; a benzothienyl radical, a naphthyl radical and an indolyl radicals, which can carry alkyl groups having from 1 to 3 carbon atoms on the nitrogen atom;

R' is a hydrogen atom;

R is chosen from a hydrogen atom and alkyl radicals having from 1 to 6 carbon atoms, T is chosen from a —CO— group, a —CO—O— group, a —CO—NH— group and a —CS—NH— group; and m is an integer equal to 2 or 3; p is equal to 1; and q is equal to 0; or (3) Y is chosen from: >N—Ar' groups, >N—CH$_2$—Ar' groups, and $>CX—(CH_2)_x—Ar'$ groups, in which:

Ar is defined as above in VIII(2);

X is chosen from OH radical, alkyloxy radicals, acyloxy radicals and carbalkoxy radicals having from 1 to 4 carbon atoms; carboxyl radicals, cyano radicals; amino radicals, pyrrolidino radicals, piperidino radicals, and morpholino radicals, which can be unsubstituted, mono- or disubstituted by at least one substituent chosen from alkyl radicals, hydroxyalkyl radicals and acyl radicals having from 1 to 4 carbon atoms; an —SH radical or alkylthio radical in which the alkyl part contains from 1 to 4 carbon atoms; and x is 0 or 1; or Y is a $=C—(CH_2)_x—Ar'$ group in which x is 0 or 1 and Ar' is defined as above in VIII(2) with the exception that Ar' cannot represent a substituted indolyl radical;

R and R' together form

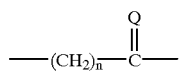

chains, in which:

Q is an oxygen atom or 2 hydrogen atoms, n is equal to 0 to 3;

T is —CO— or —CH$_2$—; and

Z is chosen from a phenyl radical and a naphthyl radical unsubstituted or substituted by at least one substituent chosen from: halogen atoms, a trifluoromethyl radical, an OH radical, alkyl radicals having from 1 to 4 carbon atoms, and alkyloxy radicals having from 1 to 4 carbon atoms;

wherein when Z is chosen from a phenyl radical, a pyridyl radical, a thienyl radical, an indolyl radical, a quinolyl radical, a benzothienyl radical and an imidazolyl radical, or an unsubstituted, mono- or polysubstituted heteroaromatic or aromatic group, or, when T is CO, —(CH$_2$)$_q$—Z can be a benzyl radical in which the methyl radical is substituted by at least one substituent chosen from: an OH radical, alkyl radicals and alkyloxy radicals having from 1 to 4 carbon atoms, or substituted on the ring by at least one substituent chosen from: halogen atoms, a trifluoromethyl radical, an OH radical, alkyl radicals and alkyloxy radicals having from 1 to 4 carbon atoms; and m is an integer equal to 2 or 3; p is equal to 1 or 2; and q is equal to 0 to 3;

wherein, if p=2, then n=1 and Q represents 2H;

(4) Y is an Ar' —X— group, in which:

Ar' is chosen from a thienyl radical and a phenyl radical, which can be unsubstituted or substituted by at least one substituent chosen from halogen atoms, alkyl and alkyloxy radicals having from 1 to 3 carbon atoms, a trifluoromethyl radical, a hydroxyl radical and a methylenedioxy radical; a pyridyl radical and an imidazolyl radical, which can be unsubstituted or substituted by at least one radical chosen from alkyl radicals;

X is chosen from an oxygen atom, a sulphur atom, a sulphonyl group, a sulphinyl group, an —NH— group, >N—CO-Alk groups, >N-Alk groups and >N-Alk-NX$_1$X$_2$ groups in which:

Alk is chosen from alkyl radicals and alkylene radicals having from 1 to 3 carbon atoms; and X$_1$ and X$_2$ are chosen from a hydrogen atom and alkyl radicals having from 1 to 3 carbon atoms; or form, with the nitrogen atom, a piperidine ring, a pyrrolidine ring or a morpholine ring;

R' is chosen from a hydrogen atom, alkyl radicals having from 1 to 4 carbon atoms, aminoalkyl radicals in which the straight-chain alkyl part contains 2 or 3 carbon atoms and the amino group can be a dialkylamino radical in which the alkyl parts contain from 1 to 4 carbon atoms, piperidino or 4-benzylpiperidino;

Ar, R, and T are defined above as in VIII(1);

Z is as defined in VIII(I) or represents an α-hydroxybenzyl radical or an α-alkylbenzyl radical in which the alkyl part contains from 1 to 3 carbon atoms; and m is an integer equal to 2 or 3; p is equal to 1; and q is equal to 0; or (5) Y is chosen from >CX—(CH$_2$)$_x$—Ar' groups, in which:

Ar' is chosen from a thienyl radical and a phenyl radical, which can be substituted by at least one substituent chosen from: halogen atoms, alkyl and alkyloxy radicals having from 1 to 4 carbon atoms, a trifluoromethyl radical and a hydroxyl radical; or a pyridyl radical;

x is 0 or 1;

X is chosen from —NH—CO-alkyl radicals in which the alkyl part contains from 1 to 6 carbon atoms;

m is 2 or 3; p is 1; and q is equal to 0;

Ar, T and Z are as defined in VIII(2); and

R' is H, and

R is H or alkyl.

14. The synergistic combination according to claim 13, wherein said at least one product endowed with antagonist activity toward NK1 receptors is a compound or a salt thereof having formula (IIb), and which is 3-[2-methoxyphenyl)methylamino]-2-phenylpiperidine.

15. The synergistic combination according to claim 1, wherein said at least one product endowed with antagonist activity towards NK1 receptors is a compound or a salt thereof having formula (IIa):

wherein said compounds of formula (II) are chosen from compounds of formula (II),

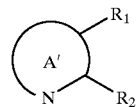

(II)

salts thereof, and stereoisometric forms thereof, in which the ring:

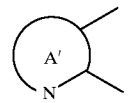

represents a monocyclic nitrogeneous hetercycle compound of formula (IIa):

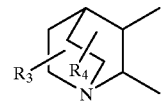

(II a)

in which:

IIa (1)

(a$_1$) R$_1$ is chosen from =N—CH$_2$—R radicals and —N=CH—R radicals, in which:

R is chosen from: cycloalkyl radicals having from 5 to 7 carbon atoms, a norbornyl radical, a pyrrolyl radical, a thienyl radical, a pyridyl radical, an indolyl radical, a biphenyl radical and a phenyl radical, which radicals can be unsubstituted or substituted by 1 or 2 substituents chosen from:

a fluorine atom, a chlorine atom, a bromine atom, a trifluoromethyl radical, an alkyl or an alkyloxy radical having from 1 to 3 carbon atoms, a carboxyl radical, an alkyloxycarbonyl radical in which the alkyl part contains from 1 to 3 carbon atoms, and a benzyloxycarbonyl radical;

R₂ is chosen from Ar—CHR'— radicals, in which:
R' is chosen from: branched alkyl radicals having 3 or 4 carbon atoms, branched alkylene radicals having 5 or 6 carbon atoms, cycloalkyl radicals having from 3 to 7 carbon atoms, a furyl radical, a thienyl radical, a pyridyl radical, an indolyl radical, a biphenyl radical, and a phenyl radical, which radicals can be unsubstituted or substituted by 1 or 2 substituents chosen from:
a fluorine atom, a chlorine atom, a bromine atom, a trifluoromethyl radical, an alkyl radical or an alkyloxy radical having from 1 to 3 carbon atoms, a carboxyl radical, an alkyloxycarbonyl radical in which the alkyl part contains from 1 to 3 carbon atoms, and a benzyloxycarbonyl radical; and
Ar is a phenyl radical;
R₃ is a hydrogen atom; and
R₄ is a hydrogen atom;
(a₂.₁) R₁ is chosen from —NH—CH₂—R radicals, in which:
R is chosen from: cycloalkyl radicals having from 5 to 7 carbon atoms, a norbornyl radical, a pyrrolyl radical, a thienyl radical, a pyridyl radical, an indolyl radical, a biphenyl radical and a phenyl radical, which radicals can be unsubstituted or substituted by 1 or 2 substituents chosen from:
a fluorine atom, a chlorine atom, a bromine atom, a trifluoromethyl radical, an alkyl radical or an alkyloxy radical having from 1 to 3 carbon atoms, a carboxyl radical, an alkyloxycarbonyl radical in which the alkyl part contains from 1 to 3 carbon atoms, and a benzyloxycarbonyl radical;
R₂ is chosen from Ar—CHR'— radicals, in which:
R' is chosen from: branched alkyl radicals having 3 or 4 carbon atoms, branched alkylene radicals having 5 or 6 carbon atoms, cycloalkyl radicals having from 3 to 7 carbon atoms, a furyl radical, a thienyl radical, a pyridyl radical, an indolyl radical, a biphenyl radical, and a phenyl radical, which radicals can be unsubstituted or substituted by 1 or 2 substituents chosen from:
a fluorine atom, a chlorine atom, a bromine atom, a trifluoromethyl radical, an alkyl radical or an alkyloxy radical having from 1 to 3 carbon atoms, a carboxyl radical, an alkyloxycarbonyl radical in which the alkyl part contains from 1 to 3 carbon atoms, and a benzyloxycarbonyl radical; and
Ar is a phenyl radical;
R₃ is a hydrogen atom; and
R₄ is a hydrogen atom;
(a₂.₂) R₁ is chosen from —NH—CH₂—R radicals, in which:
R is a phenyl radical disubstituted by a methoxy radical and a branched butyl radical;
R₂ is a benzhydryl radical;
R₃ is a hydrogen atom; and
R₄ is a hydrogen atom;
(a₂.₃) R₁ is chosen from —NH—CH₂—R radicals, in which:
R is chosen from: a phenyl radical trisubstituted by radicals X₁, X₂ and X₃, in which: X₁ is chosen from a hydrogen atom, alkyl and alkyloxy radicals having from 1 to 10 carbon atoms which can be unsubstituted or substituted by from 1 to 3 fluorine atoms; and X₂ and X₃ are chosen from a hydrogen atom, halogen atoms, a NO₂ radical, alkyl and alkyloxy radicals having from 1 to 10 carbon atoms, which can be unsubstituted or substituted by from 1 to 3 substituents chosen from: a fluorine atom, an OH radical, a CN radical, a phenyl radical, an NH₂ radical, an alkylamino radical, a dialkylamino radical, an alkylcarbamoyl radical, an alkylcarbamoylalkyl radical and an acylamino radical in which the alkyl and acyl parts contain from 1 to 6 carbons; and an alkyloxyalkyl radical in which the alkyl parts contain from 1 to 4 carbon atoms;
R₂ is chosen from: Ar—CHR'— radicals, in which:
R' is chosen from: branched alkyl radicals having 3 or 4 carbon atoms, branched alkylene radicals having 5 or 6 carbon atoms, cycloalkyl radicals having from 3 to 7 carbon atoms, a furyl radical, a thienyl radical, a pyridyl radical, an indolyl radical, a biphenyl radical, and a phenyl radical, which radicals can be unsubstituted or substituted by 1 or 2 substituents chosen from:
a fluorine atom, a chlorine atom, a bromine atom, a trifluoromethyl radical, an alkyl radical or an alkyloxy radical having from 1 to 3 carbon atoms, a carboxyl radical, an alkyloxycarbonyl radical in which the alkyl part contains from 1 to 3 carbon atoms, and a benzyloxycarbonyl radical, or
R' is chosen from alkyl and alkyloxy radicals having from 1 to 10 carbon atoms which can be unsubstituted or substituted by from 1 to 3 fluorine atoms; and
Ar is chosen from: a phenyl radical, a biphenyl radical, a naphthyl radical, a pyridyl radical, a thienyl radical and a furyl radical which can be mono-, di- and tri-substituted by a group chosen from halogen atoms and alkyl and alkyloxy radicals having from 1 to 10 carbon atoms which can be unsubstituted or substituted by from 1 to 3 fluorine atoms;
R₃ is a hydrogen atom; and
R₄ is a hydrogen atom;
(a₃) R₁ is chosen from —NH—(C=Y)—R radicals, in which:
R is chosen from: benzopyran radicals that may contain an additional heteroatom chosen from O, S, N⁺H, N⁺alkyl and N⁺aralkyl; and benzofuran radicals; wherein said benzopyran and benzofuran radicals may be unsubstituted or substituted in the position a to the oxygen by at least one methyl radical, and/or substituted by an oxo radical or thioxo radical and/or substituted on the phenyl ring of said benzopyran and benzofuran radicals by at least one group chosen from: halogen atoms, alkyl radicals, haloalkyl radicals, aralkyl radicals, alkyloxy radicals, aralkyloxy radicals, acyl radicals, acyloxy radicals, an OH radical, an NH₂ radical, a CN radical, an NO₂ radical, —NH—CO—R" radicals, S(O)ₙ—R" radicals, —NH—SO₂R" radicals, COOR" radicals, CONR"R'" radicals, OCONR"R'" radicals, CSNR"R'" radicals and SO₂NR"R'" radicals, in which R" and R'" are independently chosen from: a hydrogen atom, an alkyl radical, a phenyl radical and an aralkyl radical, n is 0, 1, or 2, and Y is chosen from O, S and 2H;
R₂ is chosen from —CHR₅R₆ radicals, in which:
R₅ is chosen from a thienyl radical and a phenyl radical, and R₆ is chosen from: an alkyl radical, an alkenyl radical, a cycloalkyl radical, a furyl radical, a thienyl radical, a pyridyl radical, an indolyl radical, a biphenyl radical and a phenyl radical;
R₃ is chosen from H and an alkyl radical; and
R₄ is a hydrogen atom;
(b₂) R₁ is chosen from —NH—CH₂—R radicals, in which:
R is chosen from: a phenyl radical trisubstituted by radicals X₁, X₂ and X₃, in which: X₁ is chosen from: a hydrogen atom, alkyl and alkyloxy radicals having from 1 to 10 carbon atoms which can be unsubstituted or substituted by from 1 to 3 fluorine atoms; and $X_2$ and $X_3$ are chosen from: a hydrogen atom, halogen atoms, a $NO_2$ radical, alkyl and alkyloxy radicals having from 1 to 10 carbon atoms, which can be unsubstituted or substituted by from 1 to 3 substituent chosen from: a fluorine atom, an OH radical, a CN radical, a phenyl radical, an $NH_2$ radical, an alkylamino radical, a dialkylamino radical, an alkylcarbamoyl radical, an alkylcarbamoylalkyl radical and an acylamino radical in which the alkyl and acyl parts contain from 1 to 6 carbons; and an alkyloxyalkyl radical in which the alkyl parts contain from 1 to 4 carbon atoms;

$R_2$ is chosen from: a phenyl radical, a biphenyl radical, a naphthyl radical, a pyridyl radical, a thienyl radical and a furyl radical, which radicals can be mono-, di- or tri-substituted by a group chosen from: halogen atoms and alkyl and alkyloxy radicals having from 1 to 10 carbon atoms which can be unsubstituted or substituted by from 1 to 3 fluorine atoms;

$R_3$ is an alkyl radical having from 1 to 6 carbon atoms; and $R_4$ is a hydrogen atom;

(c) $R_1$ is chosen from —NH—$CH_2$—R radicals, in which:
R is chosen from: a phenyl radical, a thienyl radical, a pyridyl radical and a furyl radical, which radicals can be unsubstituted or substituted by from 1 to 3 substituents chosen from: a fluorine atom, a chlorine atom, a bromine atom, an iodine atom, a trifluoromethyl radical, alkyl radicals and alkyloxy radicals having from 1 to 4 carbon atoms;

$R_2$ is chosen from: a phenyl radical, a naphthyl radical, a thienyl radical, a pyridyl radical and a furyl radical, which radicals can be unsubstituted or substituted by from 1 to 3 substituents chosen from: a fluorine atom, a chlorine atom, a bromine atom, an iodine atom, a trifluoromethyl radical, alkyl radicals and alkyloxy radicals having from 1 to 4 carbon atoms;

$R_3$ is chosen from: a hydrogen atom and alkyl radicals having from 1 to 6 carbon atoms situated in the 5- or 6-position of said ring of formula (IIa); and $R_4$ is a hydrogen atom;

(d) $R_1$ is chosen from —NH—$CH_2$—R radicals, in which:
R is chosen from: a phenyl radical, a naphthyl radical, a pyridyl radical, a quinolyl radical, a thienyl radical, a furyl radical, a phenoxyphenyl radical, an oxazolyl radical, a tetrazolyl radical, a thiazolyl radical, an imidazolyl radical and a pyrazolyl radical, which radicals can be unsubstituted or substituted by at least one substituent chosen from:
alkyl and alkyloxy radicals, which radicals may be unsubstituted or substituted from 1 to 3 halogen atoms, alkylthio radicals, alkylsulphinyl radicals, alkylsulphonyl radicals, alkylsulphonylamino radicals, and dialkylamino radicals, in which the alkyl parts can be unsubstituted or substituted by at least one substituent chosen from alkylsulphinyl radicals and alkylsulphonyl radicals in which the alkyl parts contain from 1 to 6 carbon atoms; sulphonamido radicals and alkenyl radicals having from 2 to 6 carbon atoms; or R is chosen from: phenyl radicals substituted by at least one substituent chosen from: halogen atoms, alkynyl radicals, alkylamino radicals, N-alkyl-N-(alkylsulphonyl)amino radicals and N-alkyl-N-alkanoylamino radicals, which radicals can be unsubstituted or substituted by a halogen atom on the alkylsulphonyl or alkanoyl part; alkylsulphonylamino radicals and alkanoylamino radicals, in which the alkyl parts can be unsubstituted or substituted by at least one halogen atom;

$R_2$ is chosen from Ar—CH(Ar')— radicals, in which:
Ar and Ar' are cyclic radicals chosen from: a phenyl radical, a naphthyl radical, a pyridyl radical, a quinolyl radical, a thienyl radical, a furyl radical, a phenoxyphenyl radical, an oxazolyl radical, a tetrazolyl radical, a thiazolyl radical, an imidazolyl radical and a pyrazolyl radical, which radicals can be unsubstituted or substituted by at least one substituent chosen from:
alkyl and alkyloxy radicals, which radicals may be unsubstituted or substituted from 1 to 3 halogen atoms, alkylthio radicals, alkylsulphinyl radicals, alkylsulphonyl radicals, alkylsulphonylamino radicals, and dialkylamino radicals, in which the alkyl parts can be unsubstituted or substituted by at least one substituent chosen from alkylsulphinyl radicals and alkylsulphonyl radicals in which the alkyl parts contain from 1 to 6 carbon atoms; sulphonamido radicals and alkenyl radicals having from 2 to 6 carbon atoms; or said cyclic radicals are chosen from: phenyl radicals substituted by at least one substitutent chosen from: halogen atoms, alkynyl radicals, alkylamino radicals, N-alkyl-N-(alkylsulphonyl)amino radicals and N-alkyl-N-alkanoylamino radicals, which radicals can be unsubstituted or substituted by a halogen atom on the alkylsulphonyl or alkanoyl part; alkylsulphonylamino radicals and alkanoylamino radicals, in which the alkyl parts can be unsubstituted or substituted by at least one halogen atom;

wherein said cyclic radicals can be unsubstituted or substituted by at least one substituent chosen from:
alkyl radicals, alkyloxy radicals, alkylthio radicals, alkylsulphinyl radicals, and alkylamino radicals in which the alkyl parts contain from 1 to 4 carbon atoms, or by trifluoromethyl or trifluoromethoxy radicals;

$R_3$ is chosen from alkyl radicals having from 1 to 6 carbon atoms, alkenyl radicals having from 2 to 6 carbon atoms, and cycloalkyl radicals having from 3 to 8 carbon atoms, wherein said alkyl radicals, alkenyl radicals, and cycloalkyl radicals may be unsubstituted or substituted with an alkyloxy radical, a carbamoyl radical, a —$CONR_aR_b$ radical, a —COOH radical, a —$COOR_a$ radical, a —$CHR_aOR_b$ radical, a —$CHR_aNR_bR_c$ radical, a —$COR_a$ radical, a —$CONR_aOR_b$ radical, or an aryl radical:

$R_3$ is also chosen from alkyloxy radicals, a carbamoyl radical, —$CONR_aR_b$ radicals, a —COOH radical, —$COOR_a$ radicals, —$CHR_aOR_b$ radicals, —$CHR_aNR_bR_c$ radicals, —$COR_a$ radicals, —$CONR_aOR_b$ radicals, and aryl radicals: or
wherein $R_a$ and $R_b$ each independent of the other, are chosen from aryl radicals, cycloalkyl radicals, alkyloxy radicals, alkyl radicals, and a hydrogen atom;

$R_3$ is also chosen from Y—$(CH_2)_m$—$CHR_d$—$(CH_2)_n$—$NR'_d$—CO— radicals, in which:
Rd is chosen from a hydrogen atom, alkyl radicals, a benzyl radical, and —$(CH_2)_p$—Y radicals;
$R'_d$ is chosen from a hydrogen atom; alkyl radicals which may be unsubstituted or substituted by an —OH radical, a —NH$_2$ radical, a —SCH$_3$ radical, or a —SH radical; a benzyl radical; —(CH$_2$)$_p$—Y radicals; a 4-hydroxybenzyl radical; and a 3-indolylmethyl radical;

Y is chosen from —CN, —CH$_2$Z, and —COZ, in which Z is chosen from an —OH radical, an —NH$_2$ radical, —Oalkyl radicals, —NHalkyl radicals, and —N(alkyl)$_2$ radicals; and m, n, and p, each independently of the other, have a value of 0, 1, 2, or 3;

wherein, in the definition of R$_3$, R$_a$, R$_b$, and R$_c$, said aryl radicals are chosen from a phenyl radical, a naphthyl radical, a pyridyl radical, a quinolyl radical, a thienyl radical, a furyl radical, a phenoxyphenyl radical, an oxazolyl radical, a tetrazolyl radical a thiazolyl radical, an imidazoyl radical, and a pyrazolyl radical, wherein, in the definition of R$_3$, R$_a$, R$_b$, and R$_c$, said aryl radicals may be unsubstituted or substituted by an alkyl radical which is unsubstituted or substituted with from 1 to 3 halogen atoms or an alkyloxy radical which is unsubstituted or substituted with from 1 to 3 halogen atoms;

wherein, in the definition of R$_3$, R$_a$, R$_b$, and R$_c$, said aryl radicals may be unsubstituted or substituted by an alkylthio radical, an alkylsulphinyl radical, an alkylsulphonyl radical, an alkylsulphonylamino radical, or a dialkylamino radical, wherein the alkyl part of said alkylthio, alkylsulphinyl, alkylsulphonyl, alkylsulphonylamino, or dialkylamino radicals may be unsubstituted or substituted by an alkylsulphinyl radical having from 1 to 6 carbon atoms, an alkylsulphonyl radical having from 1 to 6 carbon atoms, a sulphonamido radical having from 2 to 6 carbon atoms, or an alkenyl radical having from 2 to 6 carbon atoms;

wherein, in the definition of R$_3$, R$_a$, R$_b$, and R$_c$, when said aryl radical is a phenyl radical, said phenyl radical may be unsubstituted or substituted by a halogen atom, an alkynyl radical, an alkylamino radical, an N-alkyl-N-(alkylsulphonyl)amino radical, or an N-alkyl-N-alkanoylamino radial, wherein said alkynyl, alkylamino, N-alkyl-N-(alkylsulphonyl)amino, or N-alkyl-N-alkanoylamino radials may be unsubstituted or substituted with a halogen atom on the alkylsulphonyl part or alkanoyl part; an alkylsulphonylamino radical or an alkanoylamino radical, wherein said alkylsulphonylamino or alkanoylamino radicals may be unsubstituted or substituted by a halogen atom; and R$_4$ is a hydrogen atom; or (2) R$_1$ is chosen from —NH—CH$_2$—R radicals, in which:

R is chosen from: a phenyl radical trisubstituted by radicals X$_1$, X$_2$ and X$_3$, in which: X$_1$ is chosen from: a hydrogen atom, alkyl and alkyloxy radicals having from 1 to 10 carbon atoms which can be unsubstituted or substituted by from 1 to 3 fluorine atoms; and X$_2$ and X$_3$ are chosen from: a hydrogen atom, halogen atoms, a NO$_2$ radical, alkyl and alkyloxy radicals having from 1 to 10 carbon atoms, which can be unsubstituted or substituted by from 1 to 3 substituent chosen from: a fluorine atom, an OH radical, a CN radical, a phenyl radical, an NH$_2$ radical, alkylamino radicals, a dialkylamino radical, an alkylcarbamoyl radical, an alkylcarbamoylalkyl radical and an acylamino radical in which the alkyl and acyl parts contain from 1 to 6 carbons; and an alkyloxyalkyl radical in which the alkyl parts contain from 1 to 4 carbon atoms;

or R is chosen from: a cycloalkyl radical having from 5 to 7 carbon atoms, a pyrrolyl radical, a thienyl radical, a pyridyl or a phenyl radical which can be unsubstituted or substituted by from 1 to 3 substituents chosen from: a fluorine atom, a chlorine atom, a bromine atom, a trifluoromethyl radical, an alkyl or alkyloxy radical having from 1 to 3 carbon atoms, a carboxyl radical, an alkyloxycarbonyl radical, in which the alkyl part contains from 1 to 3 carbon atoms, and benzyloxycarbonyl radicals;

R$_2$ is chosen from —CHR'R" radicals, in which:

R' is chosen from: a furyl radical, a thienyl radical, a pyridyl radical, an indolyl radical, a biphenyl and a phenyl radical, which radicals can be unsubstituted or substituted by 1 or 2 substituents chosen from:

halogen atoms, alkyl and alkyloxy radicals having from 1 to 10 carbon atoms, which radicals can be unsubstituted or substituted by from 1 to 3 substituents chosen from: a fluorine atom, a carboxyl radical, an alkyloxycarbonyl radical where the alkyl part contains from 1 to 3 carbon atoms, and a benzyloxycarbonyl radical; and R" is chosen from: a thienyl radical, a phenyl radical, a halophenyl radical and a phenyl radical substituted by a substituent chosen from: alkyl and alkyloxy radicals having from 1 to 10 carbon atoms, which can be unsubstituted or substituted by from 1 to 3 fluorine atoms;

R$_3$, in the 5-position of said ring of formula (Ia), forms with R$_4$, an alkylene chain containing from 3 to 5 carbon atoms if R$_4$ is in the 6-position, or an alkylene chain containing from 2 to 3 carbon atoms if R$_4$ is in the 7-position, or an alkylene chain containing from 2 to 4 carbon atoms if R$_4$ is in the 8-position, or, when R$_3$ is in the 5-position and R$_4$ is in the 6-position, R$_3$ and R$_4$ can form a chain:

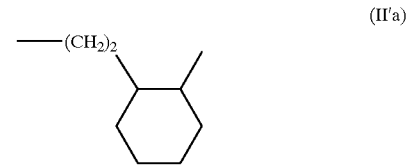

(II'a)

or, when R$_4$ is in the 8-position and R$_3$ is in the 5-position, R$_3$ and R$_4$ can form a chain —CH$_2$—X—CH$_2$—, in which X is chosen from: O, S, NH and >N(alkylamino) radicals, in which the alkyl part contains from 1 to 3 carbon atoms.

16. The synergistic combination according to claim 1, wherein said at least one product endowed with antagonist activity towards NK2 receptors is chosen from piperidine compounds and salts thereof having formula (X):

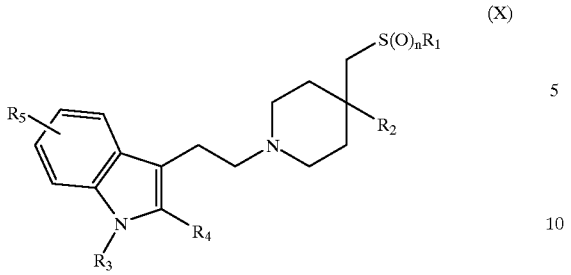

in which:
- R₁ is a phenyl radical which can be unsubstituted or substituted by at least one substituent chosen from: a CF₃ radical, halogen atoms, and 1 or 2 alkyl or alkoxy radicals having from 1 to 4 carbon atoms;
- R₂ is chosen from a hydrogen atom, an OH radical and alkyl radicals having from 1 to 4 carbon atoms;
- R₃ is chosen from a hydrogen atom and alkyl radicals having from 1 to 4 carbon atoms;
- R₄ is chosen from a hydrogen atom, alkyl radicals and alkyloxy radicals having from 1 to 4 carbon atoms;
- R₅ is chosen from a hydrogen atom, alkyl radicals having from 1 to 4 carbon atoms, a CF₃ radical, a CN radical, and halogen atoms; and
- n is 0 to 2.

17. The synergistic combination according to claim 1, wherein said at least one product endowed with antagonist activity towards NK1 receptors is chosen from compounds of formula (I) below, and salts thereof, wherein said compounds of formula (I) are chosen from perhydroisoindole compounds and salts thereof of formula (I):

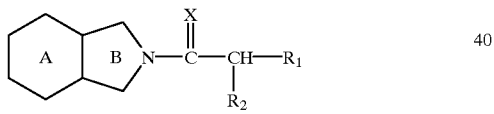

in which:
R₁ represents a phenyl radical which may be unsubstituted or substituted by at least one substitutent chosen from:
  halogen atoms, hydroxyl radicals, alkyl radicals which can be unsubstituted or substituted by at least one group chosen from: halogen atoms, amino radicals, alkylamino radicals, and dialkylamino radicals; alkyloxy and alkylthio radicals which can be unsubstituted or substituted by a group chosen from: phenyl, hydroxyl and amino radicals; and dialkylamino radicals, alkylamino radicals, amino radicals, hydroxyl radicals, and dialkylamino radicals in which the alkyl parts form, with the nitrogen atom to which they are attached, 5- to 6-membered heterocycle rings which can contain an additional heteroatom chosen from oxygen, sulphur and nitrogen atoms, said heterocycle rings being unsubstituted or substituted by at least one group chosen from: alkyl radicals, hydroxyl radicals and hydroxyalkyl radicals;
  alkyloxy radicals and alkylthiol radicals which can be unsubstituted or substituted by at least one group chosen from: amino radicals, alkylamino radicals, and dialkylamino radicals in which the alkyl parts can form, with the nitrogen atom to which they are attached, 5- to 6-membered heterocycle rings which can contain an additional heteroatom chosen from oxygen, sulphur, and nitrogen atoms, said heterocycle rings being unsubstituted or substituted by at least one group chosen from: alkyl radicals, hydroxyl radicals, and hydroxyalkyl radicals; or R₁ represents a cyclohexadienyl radical, a naphthyl radical, a saturated or unsaturated, mono- or polycyclic heterocyclyl radical having from 5 to 9 carbon atoms and at least one heteroatom chosen from oxygen, nitrogen and sulphur atoms, wherein said at least one heteroatom is unsubstituted or substituted by at least one group chosen from: halogen atoms, alkyl radicals, and alkyloxy radicals;

R₂ is chosen from a hydrogen atom, halogen atoms, a hydroxyl radical, alkyl radicals, aminoalkyl radicals, alkylaminoalkyl radicals, dialkylaminoalkyl radicals, alkyloxy radicals, alkylthio radicals, acyloxy radicals, carboxyl radicals, alkyloxycarbonyl radicals, dialkylaminoalkyloxycarbonyl radicals, benzyloxycarbonyl radicals, amino radicals and acylamino radicals;

the bicycle:

represents a perhydroisoindole or thiapyranopyrrole ring of formula:

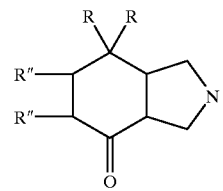

(Ia)

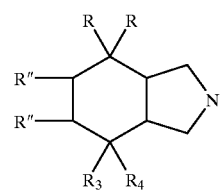

(Ib)

and X is chosen from: oxygen and sulphur atoms; NR₆ radicals in which R₆ is chosen from: a hydrogen atom; alkyl radicals containing from 1 to 12 carbon atoms which may be unsubstituted or substituted by at least one radical chosen from: carboxyl radicals, dialkylamino radicals, acylamino radicals, alkyloxycarbonyl radicals, alkyloxycarbonylamino radicals, carbamoyl radicals, alkylcarbamoyl radicals and dialkylcarbamoyl radicals, the alkyl portions of these substituents being unsubstituted or substituted by at least one radical chosen from dialkylamino radicals and phenyl radicals; a phenyl radical which may be unsubstituted or substituted by at least one group chosen from: halogen atoms, alkyl radicals, alkyloxy radicals and dialkylamino radicals; or R₆ is chosen from a naphthyl radical, a thienyl radical, a furyl radical, a pyridyl radical, an imidazolyl radical; and a dialkylamino radical;

wherein if the bicycle is of formula (Ib), X is chosen from an oxygen atom, and an NH radical; or the bicycle,

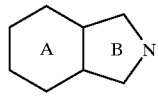

represents a perhydroisoindole or thiapyranopyrrole ring of formula:

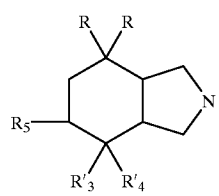

(Id)

and X is an oxygen atom;

wherein in the formulae (Ia), (Ib), and (Id):

the R symbols are identical and represent phenyl radicals which can be unsubstituted or substituted by at least one halogen atom or by at least one methyl radical in the 2- or 3-position;

the R" symbols are identical and are hydrogen atoms or together form a bond;

$R_3$ is chosen from halogen atoms and a hydroxyl radical; and $R_4$ is a hydrogen atom or, simultaneously with $R_3$, $R_4$ is a halogen atom;

$R'_3$ is a phenyl radical which can be unsubstituted or substituted in the 2-position by at least one radical chosen from alkyl radicals and alkyloxy radicals having from 1 or 2 carbon atoms; $R'_4$ is chosen from a fluorine atom and a hydroxyl radical; and $R_5$ is a hydrogen atom; or $R'_4$ and $R_5$ are both hydroxyl radicals; or $R'_4$ forms a bond with $R_5$;

$R''_3$ is a hydrogen atom and $R''_4$ is chosen from a fluorine atom and a hydroxyl radical; or $R''_3$ is a phenyl radical which can be unsubstituted or substituted in the 2-position by at least one radical chosen from alkyl radicals and alkyloxy radicals having from 1 or 2 carbon atoms and $R''_4$ is a hydroxyl radical; or $R''_3$ and $R''_4$ together form an oxo radical; and wherein said compounds of formulae (Ia), (Ib), and (Id) may be in their respective stereoisomeric forms;

wherein said at least one product endowed with antagonist activity towards NK2 receptors is chosen from piperidine compounds and salts thereof having formula (X):

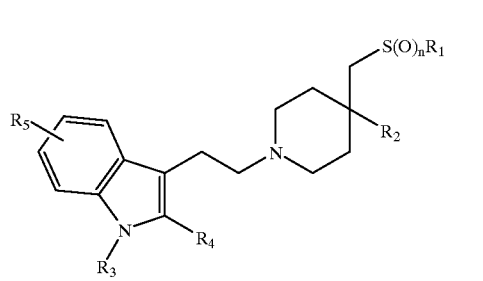

(X)

in which:

$R_1$ is a phenyl radical which can be unsubstituted or substituted by at least one substituent chosen from: a $CF_3$ radical, halogen atoms, and 1 or 2 alkyl or alkoxy radicals having from 1 to 4 carbon atoms;

$R_2$ is chosen from a hydrogen atom, an OH radical and alkyl radicals having from 1 to 4 carbon atoms;

$R_3$ is chosen from a hydrogen atom and alkyl radicals having from 1 to 4 carbon atoms;

$R_4$ is chosen from a hydrogen atom, alkyl radicals and alkyloxy radicals having from 1 to 4 carbon atoms;

$R_5$ is chosen from a hydrogen atom, alkyl radicals having from 1 to 4 carbon atoms, a $CF_3$ radical, a CN radical, and halogen atoms; and n is 0 to 2.

* * * * *

UNITED STATES PATENT AND TRADEMARK OFFICE
CERTIFICATE OF CORRECTION

PATENT NO.   : 6,177,450 B1
DATED        : January 23, 2001
INVENTOR(S)  : Claude Garret et al.

It is certified that error appears in the above-identified patent and that said Letters Patent is hereby corrected as shown below:

<u>Column 43,</u>
Line 31, "fomyl" should read -- formyl --.

<u>Column 51,</u>
Line 8, "phenyk" should read -- phenyl --.

<u>Column 54,</u>
Line 4, "a indolyl" should read -- an indolyl --.
Line 14, "R'" should read -- R --.

<u>Column 55,</u>
Line 34, ">N-A'" should read -- >N-Ar' --.
Line 48, "$(Ch_2)_xAr$" should read -- $(Ch_2)_x$-Ar --.

<u>Column 57,</u>
Line 12, "hetercycle" should read -- heterocycle --.
Line 25, "$(CH_2)n$" should read -- $(CH_2)_n$ --.
Line 61, "$R_2$and $R_3$" should read -- $R_2$ and $R_3$ --.

<u>Column 58,</u>
Line 47, "alkylcarbomoyl" should read -- alkylcarbamoyl --.
Lines 49-50, "sustitutents" shoud read -- substituents --.

<u>Column 59,</u>
Line 37, "trifluromethyl" should read -- trifluoromethyl --.

<u>Column 60,</u>
Line 67, "atoms," should read -- atoms; --.

<u>Column 61,</u>
Line 11, "a indolyl" should read -- an indolyl --.
Lines 45 and 54, delete "by" (second occurrences).
Line 57, after "trifluoromethyl radical", insert -- ; --.

UNITED STATES PATENT AND TRADEMARK OFFICE
CERTIFICATE OF CORRECTION

PATENT NO. : 6,177,450 B1
DATED : January 23, 2001
INVENTOR(S) : Claude Garret et al.

It is certified that error appears in the above-identified patent and that said Letters Patent is hereby corrected as shown below:

Column 62,
Lines 26 and 32, "substituenet" should read -- substituent --.
Line 32, "substitutent" should read -- substituent --.
Line 34, "radicals;" should read -- radical; --.

Column 66,
Line 40, "position a" should read -- position α --.

Column 67,
Line 7, "substituent" shoud read -- substituents --.

Column 68,
Line 27, "substitutent" should read -- substituent --.
Line 58, "radicals:" should read -- radicals; --.
Line 64, "Rd" should read -- $R_d$ --.

Column 69,
Line 15, after "tetrazolyl radical", insert -- , --.
Line 16, "pyrazolyl radical," should read -- pyrazolyl radical; --.
Line 41, "radial" should read -- radical --.
Line 44, "radials" should read -- radicals --.

Column 70,
Line 36, "(Ia)" should read -- (IIa) --.
Line 42, "$R_4$is" should read -- $R_4$ is --.
Line 53, "$R_3$is" should read -- $R_3$ is --.

UNITED STATES PATENT AND TRADEMARK OFFICE
CERTIFICATE OF CORRECTION

PATENT NO.    : 6,177,450 B1
DATED         : January 23, 2001
INVENTOR(S)   : Claude Garret et al.

It is certified that error appears in the above-identified patent and that said Letters Patent is hereby corrected as shown below:

Column 71,
Line 47, "substitutent" should read -- substituent --.

Signed and Sealed this

Eighth Day of April, 2003

JAMES E. ROGAN
*Director of the United States Patent and Trademark Office*